United States Patent
Lurvey et al.

(10) Patent No.: US 8,431,086 B2
(45) Date of Patent: Apr. 30, 2013

(54) MEDICAL FLUID ACCESS DEVICE WITH ANTISEPTIC INDICATOR

(75) Inventors: Kent L. Lurvey, Grayslake, IL (US); Shmuel Sternberg, Palatine, IL (US); Vadim V. Krongauz, Bartlett, IL (US); Rosa H. Yeh, Libertyville, IL (US); Robin G. Pauley, Lake Villa, IL (US); Dustin C. Cawthon, Crystal Lake, IL (US); Ton That Hai, Round Lake, IL (US); Lecon L. Woo, Libertyville, IL (US); Ashok K. Khanna, Lake Zurich, IL (US); Birendra K. Lal, Lake Zurich, IL (US); Michael Tung-Kiung Ling, Vernon Hills, IL (US); William S. Hoerle, Cary, IL (US); Craig L. Sandford, Buffalo Grove, IL (US); Mark A. Nordhaus, Antioch, IL (US); Alexander Savitski, Libertyville, IL (US); Nicklaus J. Kirichkow, Fox Lake, IL (US); Kenneth Glen Suh, Grayslake, IL (US); Sivaramakrishnan Krishnamoorthy, Lake Zurich, IL (US); Hsinjin E. Yang, Long Grove, IL (US); Robert A. Clarke, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/154,848

(22) Filed: Jun. 7, 2011

(65) Prior Publication Data

US 2011/0236258 A1 Sep. 29, 2011

Related U.S. Application Data

(60) Division of application No. 11/780,917, filed on Jul. 20, 2007, now Pat. No. 7,981,381, which is a continuation-in-part of application No. 11/550,643, filed on Oct. 18, 2006, now abandoned, which is a continuation-in-part of application No. 11/458,816, filed on Jul. 20, 2006.

(30) Foreign Application Priority Data

Jul. 20, 2007 (WO) ............... PCT/US2007/074003

(51) Int. Cl.
 *G01N 21/75* (2006.01)
(52) U.S. Cl.
 USPC ............. 422/400; 422/50; 422/500; 116/200
(58) Field of Classification Search ................. 422/400, 422/500, 405, 50; 116/200
 See application file for complete search history.

(56) References Cited

U.S. PATENT DOCUMENTS

| 4,045,400 A | 8/1977 | Korshak et al. |
| 4,169,811 A | 10/1979 | Yoshilawa et al. |

(Continued)

FOREIGN PATENT DOCUMENTS

| CA | 1075605 | 4/1980 |
| DE | 2742875 | 4/1979 |

(Continued)

OTHER PUBLICATIONS

Saari, Kinda A, et al., "pH Sensor based on immobolized fluoresceinamine," 1982, Analytical Chemistry, vol. 54, p. 821-823.

(Continued)

*Primary Examiner* — Jyoti Nagpaul
(74) *Attorney, Agent, or Firm* — K&L Gates LLP

(57) ABSTRACT

A medical device, such as a vascular access device, is disclosed for providing access to a medical fluid flow path for the introduction or withdrawal of medical fluids to and from the flow path. The access device includes an indicator for providing a visual indication when the access device has been exposed to an antiseptic agent.

11 Claims, 16 Drawing Sheets

U.S. PATENT DOCUMENTS

| | | | |
|---|---|---|---|
| 4,247,498 A | 1/1981 | Castro | |
| 4,349,509 A | 9/1982 | Yoshikawa et al. | |
| 4,432,766 A | 2/1984 | Bellotti et al. | |
| 4,526,752 A | 7/1985 | Perlman et al. | |
| 4,539,256 A | 9/1985 | Shipman | |
| 4,618,533 A | 10/1986 | Steuck | |
| 4,677,076 A * | 6/1987 | Langhals | 436/40 |
| 4,739,881 A | 4/1988 | Bruso | |
| 4,828,797 A | 5/1989 | Zwarun et al. | |
| 4,834,977 A | 5/1989 | Kohama et al. | |
| 4,839,291 A | 6/1989 | Welsh et al. | |
| 4,867,881 A | 9/1989 | Kinzer | |
| 5,057,303 A | 10/1991 | Casey | |
| 5,096,813 A | 3/1992 | Krumhar et al. | |
| 5,135,489 A | 8/1992 | Jepson et al. | |
| 5,242,432 A | 9/1993 | DeFrank | |
| 5,260,023 A | 11/1993 | Evans, II | |
| 5,358,876 A | 10/1994 | Inoue et al. | |
| 5,360,413 A | 11/1994 | Leason et al. | |
| 5,443,987 A | 8/1995 | DeCicco et al. | |
| 5,690,612 A * | 11/1997 | Lopez et al. | 604/95.05 |
| 5,730,418 A | 3/1998 | Feith et al. | |
| 5,780,098 A | 7/1998 | Battles | |
| 5,782,816 A | 7/1998 | Werschmidt et al. | |
| 5,895,627 A | 4/1999 | Khachatoorian | |
| 5,900,067 A | 5/1999 | Jones | |
| 6,039,302 A | 3/2000 | Cote, Sr. et al. | |
| 6,045,539 A | 4/2000 | Menyhay | |
| 6,063,631 A | 5/2000 | Ignacio | |
| 6,093,572 A | 7/2000 | Stenholm et al. | |
| 6,126,826 A | 10/2000 | Pacheco et al. | |
| 6,150,430 A | 11/2000 | Walters et al. | |
| 6,238,623 B1 | 5/2001 | Amhof et al. | |
| 6,246,824 B1 | 6/2001 | Vandeberg et al. | |
| 6,265,476 B1 | 7/2001 | Krongauz et al. | |
| 6,287,518 B1 | 9/2001 | Ignacio et al. | |
| 6,319,243 B1 | 11/2001 | Becker et al. | |
| 6,346,417 B1 | 2/2002 | Ignacio et al. | |
| D456,524 S | 4/2002 | Hehenberger | |
| 6,395,551 B1 | 5/2002 | Kipke et al. | |
| 6,399,387 B1 | 6/2002 | Stenholm et al. | |
| 6,440,744 B1 | 8/2002 | Ignacio et al. | |
| 6,472,451 B2 | 10/2002 | Ha et al. | |
| 6,501,002 B1 | 12/2002 | Roe et al. | |
| 6,506,814 B2 | 1/2003 | Krongauz et al. | |
| 6,528,277 B1 | 3/2003 | Hendricks et al. | |
| 6,551,555 B2 | 4/2003 | Antonoplos et al. | |
| 6,561,008 B1 | 5/2003 | Mulholland et al. | |
| 6,623,955 B2 | 9/2003 | Matner et al. | |
| 6,627,443 B1 | 9/2003 | Stenholm et al. | |
| 6,669,681 B2 | 12/2003 | Jepson et al. | |
| 6,676,901 B1 | 1/2004 | Hatakeyama et al. | |
| 6,682,509 B2 | 1/2004 | Lopez | |
| 6,706,537 B2 | 3/2004 | Ignacio et al. | |
| 6,716,891 B1 | 4/2004 | Meisenburg et al. | |
| 6,749,807 B1 | 6/2004 | Schindly et al. | |
| 6,767,509 B1 | 7/2004 | Griesbach et al. | |
| 6,773,898 B1 | 8/2004 | Nyberg et al. | |
| 6,852,771 B2 | 2/2005 | Balch et al. | |
| 6,927,058 B1 | 8/2005 | Dupont | |
| 7,045,343 B2 | 5/2006 | Witcher et al. | |
| 2001/0006818 A1 | 7/2001 | Amhof et al. | |
| 2002/0051733 A1 | 5/2002 | Antonoplos et al. | |
| 2003/0012688 A1 | 1/2003 | Keppenhan, Jr. | |
| 2003/0082823 A1 | 5/2003 | Sumitani et al. | |
| 2003/0138345 A1 | 7/2003 | Schwabe | |
| 2003/0138347 A1 | 7/2003 | Lin | |
| 2003/0141477 A1 | 7/2003 | Miller | |
| 2003/0190253 A1 | 10/2003 | Kohler et al. | |
| 2003/0208165 A1 | 11/2003 | Christensen et al. | |
| 2003/0211618 A1 | 11/2003 | Patel | |
| 2003/0231990 A1 | 12/2003 | Faries, Jr. et al. | |
| 2004/0001783 A1 | 1/2004 | Bowen | |
| 2004/0052679 A1 | 3/2004 | Root et al. | |
| 2004/0243052 A1 | 12/2004 | Root et al. | |
| 2004/0258562 A1 | 12/2004 | Mills et al. | |
| 2004/0265170 A1 | 12/2004 | Read | |
| 2005/0049157 A1 | 3/2005 | MacDonald et al. | |
| 2005/0058821 A1 | 3/2005 | Smith et al. | |
| 2005/0085577 A1 | 4/2005 | Ching et al. | |
| 2005/0118056 A1 | 6/2005 | Swanson et al. | |
| 2005/0163654 A1 | 7/2005 | Stecklein et al. | |
| 2005/0169796 A1 | 8/2005 | Krakers et al. | |
| 2006/0054526 A1 | 3/2006 | Dean et al. | |
| 2006/0062687 A1 | 3/2006 | Morales | |
| 2006/0104856 A1 | 5/2006 | Farrell et al. | |
| 2007/0048503 A1 | 3/2007 | MacDonald et al. | |
| 2007/0293818 A1 | 12/2007 | Stout et al. | |

FOREIGN PATENT DOCUMENTS

| | | |
|---|---|---|
| EP | 0183396 | 6/1986 |
| EP | 0 101 185 | 5/1990 |
| EP | 0 735 368 | 10/1996 |
| EP | 0 524 021 | 9/1997 |
| EP | 0 922 219 | 6/1999 |
| EP | 1 312 918 | 5/2003 |
| EP | 1 621 178 | 2/2006 |
| GB | 1 516 738 | 7/1978 |
| JP | 56065072 | 6/1981 |
| JP | 56132560 | 10/1981 |
| JP | 2006-090773 | 4/2006 |
| WO | 9737628 | 10/1997 |
| WO | 03 021252 | 3/2003 |
| WO | 2004080595 | 9/2004 |
| WO | 2006-135344 | 12/2006 |
| WO | 2007-018301 | 2/2007 |
| WO | 2007-059900 | 5/2007 |

OTHER PUBLICATIONS

Vecchio, C., et al., Preparation of indobufen pellets by using centrifugal rotary fluidized bed equipment starting seeds, 1994, Drug Develpment and Industrial Pharmacy, vol. 20 (12), pp. 1943-1956.

Product Monograph; Primene 10% (Amino Acid) Injection; Baxter Corproation—Clintec Nutrition Division, Canada; revision Nov. 1997.

Christian Decker, Recent Developments in Radiation Curing Chemistry, Processes in PhotoReactive Polymers, 1995, pp. 35-55, Chapman & Hall, New York, NY.

Vadim V. Krongauz et al., Oxygen and Radical Photopolymerization in Films, Photoinitiated Polymerization, 2003, pp. 165-175, ACS Symposium Series 847, American Chemical Society, Washington.

International Search Report for PCT/US2007/074003.

Non-Final Office Action dated Sep. 23, 2009; U.S. Appl. No. 11/458,816, filed Jul. 20, 2006.

* cited by examiner

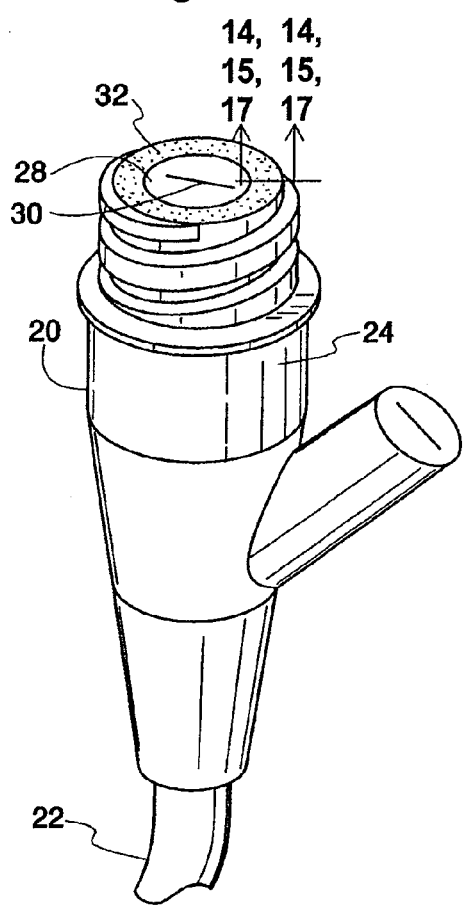
Fig. 13
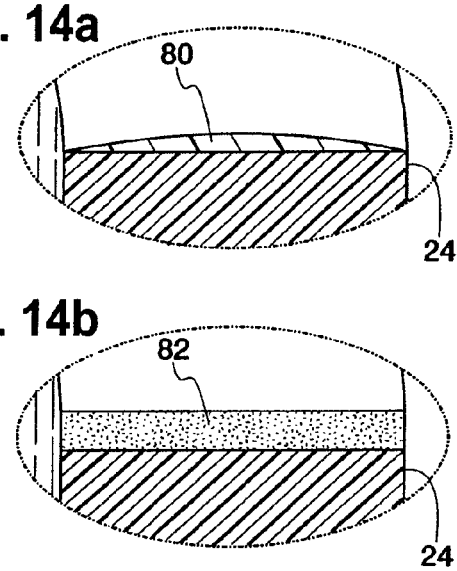
Fig. 14a
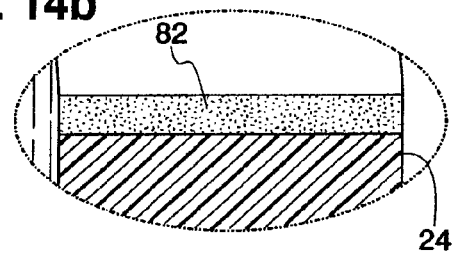
Fig. 14b
Fig. 14c
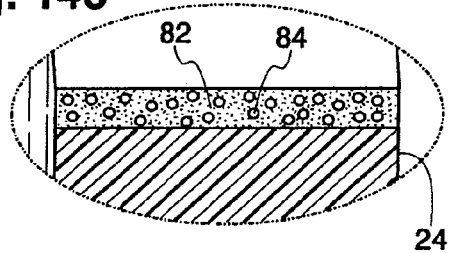
Fig. 14d
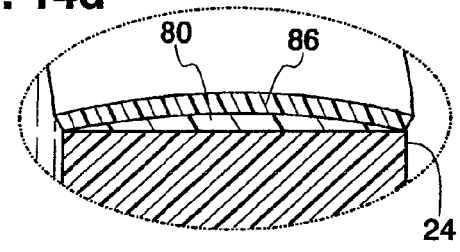
Fig. 14f
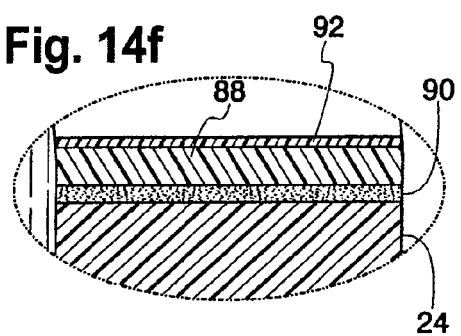
Fig. 14e
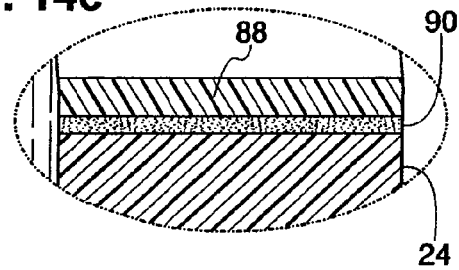

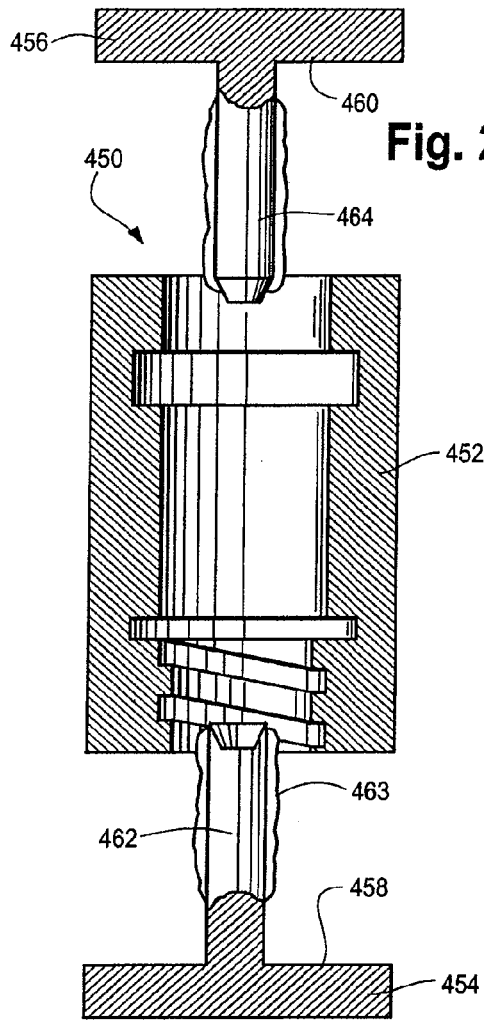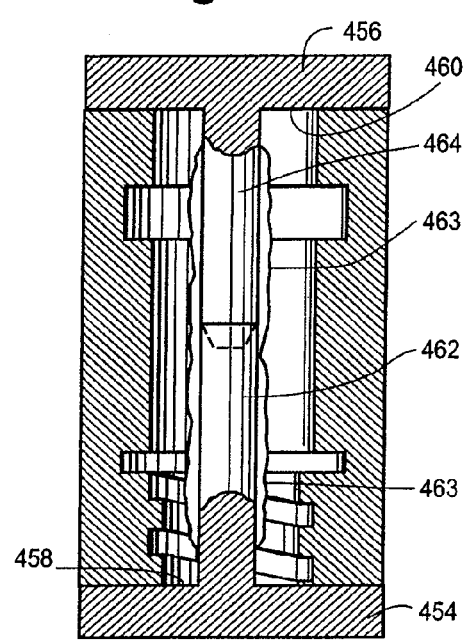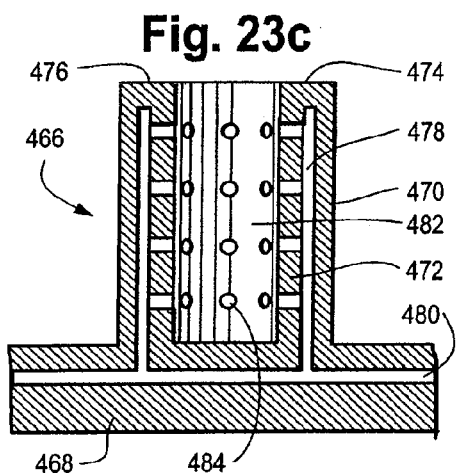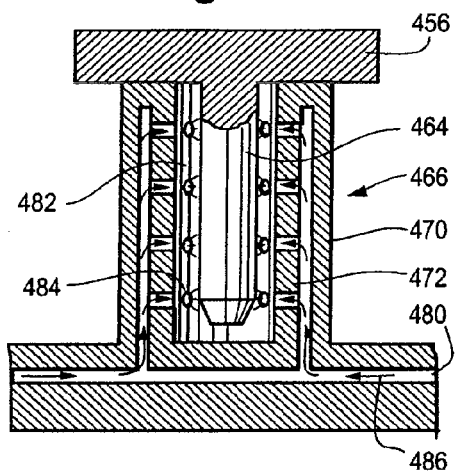

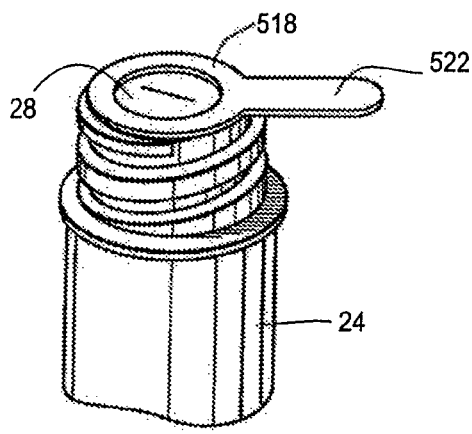
Fig. 25a
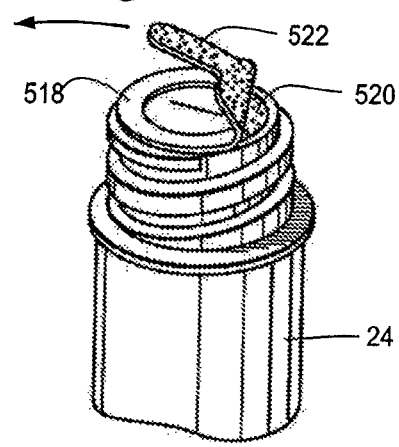
Fig. 25b
Fig. 25c
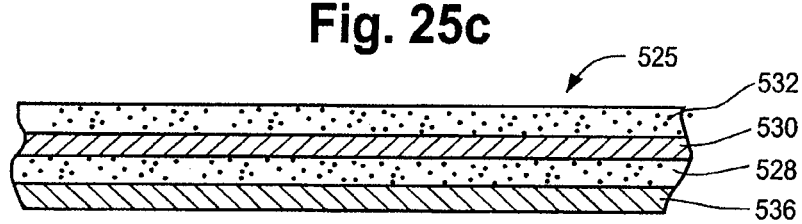
Fig. 25d
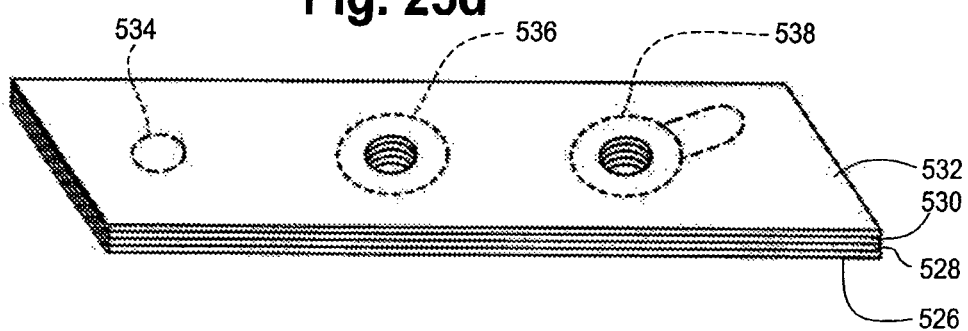
Fig. 25e
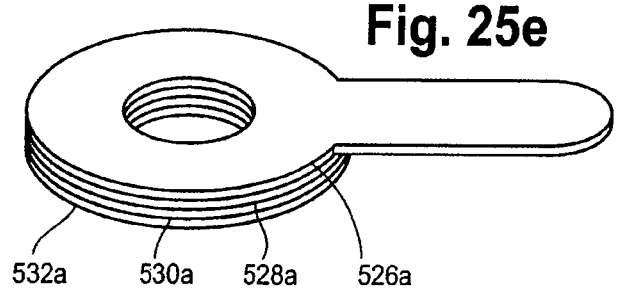

MEDICAL FLUID ACCESS DEVICE WITH ANTISEPTIC INDICATOR

CROSS-REFERENCE TO RELATED APPLICATIONS

This application is a divisional of prior application Ser. No. 11/780,917, now U.S. Pat. No. 7,981,381 filed Jul. 20, 2007, which is a continuation-in-part of prior application Ser. No. 11/550,643, now abandoned filed Oct. 18, 2006, which is a continuation-in-part of prior application Ser. No. 11/458,816, filed Jul. 20, 2006, the entire contents of which are hereby incorporated herein by reference. This application is related to U.S. patent application Ser. No. 11/780,876, filed Jul. 20, 2007, and assigned to the assignee of the present application, the entire content of which is hereby incorporated by reference.

BACKGROUND

The present disclosure relates generally to medical fluid access devices for the addition or withdrawal of fluid to or from medical fluid flow systems. More particularly, the present disclosure generally relates to medical fluid access devices including an indicator which indicates proper aseptic technique and methods of making and using the same.

Medical access devices are commonly used in association with medical fluid and vial containers and medical fluid flow systems that are connected to patients or other subjects undergoing diagnostic, therapeutic or other medical procedures. The access devices simplify the addition of fluids to or withdrawal of fluids from the container or the fluid flow system.

Within the medical field there are a wide variety of medical fluid flow systems, serving a variety of functions. One of the more common fluid flow systems is used for infusion therapy or the intravenous administration of fluids contained in a syringe or container, such as saline, antibiotics, or any number of other medically-related fluids, to a patient. These flow systems commonly include intravenous or "IV" fluid administration sets and catheters, and use polymeric tubing to fluidly connect a phlebotomized subject to one or more medical fluid sources, such as intravenous solution or medicament containers. Infusion therapy may also include vials which are accessed for withdrawal of pharmaceutical substances and subsequent administration to the subject.

Typically, such intravenous administration sets include one or more access devices providing access to the fluid flow path to allow fluid to be added to or withdrawn from the IV tubing. For example, an access device may allow for the introduction of medication, antibiotics, chemotherapeutic agents, or a myriad of other fluids to a previously established IV fluid flow system. Such administration sets are connected to a indwelling catheter through use of an access device which may or may not be similar in design to the access devices on the set. The access device may be used for withdrawing fluid from the subject for testing or other purposes, for example drawing the fluid from the patient via the catheter. Retaining an indwelling catheter in a patient eliminates the need for phlebotomizing the subject repeatedly and allows for immediate administration of medication or other fluids directly into the subject.

Several different types of access devices are well known in the medical field. Although varying in the details of their construction, these devices usually include an access site for introduction or withdrawal of medical fluids through the access device. For instance, such devices can include a housing that defines an access opening for the introduction or withdrawal of medical fluids through the housing, and a resilient valve member or gland that normally closes the access site. Beyond those common features, the design of access sites varies considerably. For example, the valve member may be a solid rubber or latex septum or be made of other elastomeric material that is pierceable by a needle, so that fluid can be injected into or withdrawn from the access device. Alternatively, the valve member may comprise a septum or the like with a preformed but normally closed aperture or slit that is adapted to receive a specially designed blunt cannula therethrough. Other types of access devices are designed for use with connecting apparatus employing standard male luers. Such an access device is commonly referred to as a "luer access device" or "luer-activated device," or "LAD." LADS of various forms or designs are illustrated in U.S. Pat. Nos. 6,682,509, 6,669,681, 6,039,302, 5,782,816, 5,730,418, 5,360,413, and 5,242,432, and U.S. Patent Application Publications Nos. 2003/0208165 and 2003/0141477, all of which are hereby incorporated by reference herein.

Access devices may also be fashioned as a part of a larger device or structure. For example, stop-cocks or the like used in medical fluid flow control may include access ports normally closed by septums or other elastomeric gland structures. Access devices or access sites may also be part of containers, such as vials or bags that have an opening closed by an elastomeric stopper or septum or other valve member.

Before an access device is actually used to introduce or withdraw liquid from a container or a medical fluid flow system or other structure or system, good medical practice or proper aseptic technique dictates that in close time proximity to the access of the site, the access site and surrounding area be contacted, usually by wiping or swabbing, with a disinfectant or sterilizing agent such as isopropyl alcohol or the like to remove or kill harmful bacteria or other pathogens and reduce the potential for contaminating the fluid flow path and harming the patient. It will be appreciated that a medical fluid flow system, such as an IV administration set and associated catheter, provides a direct avenue into a patient's vascular system. Without proper aseptic techniques by the physician, nurse or other clinician, microbes, bacteria or other pathogens found on the surface of the access device could be introduced into the IV tubing and/or catheter and thus into the patient when fluid is introduced into or withdrawn through the access device. Accordingly, care is required to assure that the healthcare practitioner uses proper aseptic techniques when the access devices are utilized for the injection or withdrawal of substances during infusion therapy such as from the container, vial, catheter or set.

Detection of the occurrence of proper aseptic technique may be problematic. Generally the wiping does not leave a residue that is detectable by the health care provider. For example the more common disinfectants are clear and their presence is not typically visually discernable. It may also be problematic to determine if the proper disinfectant was used for practicing the technique. For example wiping with water is generally not believed to be sufficient to disinfect the access device.

As described more fully below, the fluid access device of the present disclosure provides an important advance in the safe and efficient administration or withdrawal of medical fluids to or from a patient.

SUMMARY

One embodiment of the present disclosure relates is a medical fluid access device provided either alone or in combination with a medical fluid flow system. The medical fluid access device includes a housing and a valve member defining an access site for introduction or withdrawal of medical fluid through the housing. The medical fluid access device also includes an indicator that provides a perceptible indication when the access site has been exposed to an antiseptic agent, such as by directly wiping or swabbing the access device pursuant to accepted aseptic practices.

In another embodiment of the present disclosure a medical fluid access device utilized in infusion therapy. The medical fluid access device defines an access site including a resealable connector for introduction or withdrawal of medical fluid. The medical fluid access device also includes an indicator disposed in proximity to the resealable connector so that exposure to an antiseptic agent by wiping or swabbing of the connector also exposes the indicator to the antiseptic agent. In a related embodiment, the indicator may be attached to a housing or the connector of the access device. Alternately the indicator may be formed as at least a surface layer of the housing or connector. The indicator is constructed to gives a perceptible indication when at least one of the connector and housing is exposed to the antiseptic agent, pursuant to accepted aseptic practices. In a further embodiment the perceptible indication may be a visual indication using visible or other light or may be a indication that is perceptible through the use of an accessory device, for example a bar code reader.

In another embodiment, the medical fluid access device includes an access site for the introduction or withdrawal of medical fluids. An antiseptic indicator that includes a microporous surface of a polymer is provided at the access site. The antiseptic indicator is configured to change from a first perceptible appearance to a distinguishable second appearance upon exposure to an antiseptic agent. Additionally, the antiseptic indicator substantially resumes the first appearance after a period of time. The fluid access device can include a housing and a connector such as a septum or valve member and the antiseptic indicator can be attached to either the housing and/or the connector. In one embodiment, the surface of the polymer can include structural features, such as microcracks or micropatterns that change perceptible appearance upon wetting the surface with an antiseptic agent. Additionally, the antiseptic indicator can include a microporous membrane or powders that change transparency upon wetting with an antiseptic agent. Furthermore, the antiseptic indicator can include a dye, such as a solvatochromic dye, that changes color upon exposure to an antiseptic agent.

Another embodiment is a medical fluid access device that includes a housing and a valve member defining a fluid access site for the introduction or withdrawal of fluids. The medical fluid access device includes a polymeric porous indicator disposed at the access site. The indicator may also include a dye that is configured to change from a first color to a second color upon exposure to an antiseptic solution. The dye is also configured to resume the first color after a period of time. In one embodiment, the dye is a solvatochromic dye, such as a merocyanine dye or Reichardt's dye. Furthermore, the polymeric porous indicator can be an alcohol permeable polymer.

Another embodiment is a medical fluid access device that includes a housing and a connector such as a septum or valve member defining a fluid access site for the introduction or withdrawal of fluids. The medical fluid access device includes an indicator including a polymeric porous membrane disposed at the access site. The indicator may be attached to one of the housing or connector. The membrane may be constructed to alternate its transparency or opacity upon exposure to an antiseptic solution. In a further embodiment the indicator may include a substrate having a perceptible difference in appearance from the housing and/or connector.

Another embodiment is an antiseptic indicator that includes a substrate and a microporous polymer having an index of refraction from about 1.25 to 1.6 disposed on the substrate. The microporous polymer is configured to change from a substantially opaque state to a transparent state upon exposure to an antiseptic solution. Additionally, the microporous layer is configured to resume the substantially opaque state after a period of time. In one embodiment, the microporous layer is a polymer membrane. The polymer membranes can have a morphology including particle-like structures and can be resistant to blood staining. In another embodiment, the microporous layer can include a plurality of microporous polymer particles.

Another embodiment is a medical device that includes a surface having an indicator atop the surface. The indicator includes an optically active surface layer that is configured to perceptibly change from a first appearance to a second appearance upon exposure to an antiseptic solution. Additionally, the indicator is configured to resume the first appearance after a period of time. For example, in one embodiment, the optically active surface layer includes a plurality of small, fine cracks that change appearance when wetted with an antiseptic agent. In another embodiment, the optically active surface layer includes a micropattern that changes appearance upon wetting with an antiseptic agent.

Another embodiment is a medical device that has a surface including antiseptic indicator disposed on thereon. The antiseptic indicator includes micropattern having a plurality of grooves and ridges that have a groove spacing from about 0.1 µm to about 0.7 µm. The antiseptic indicator is configured to perceptibly change from a first appearance to a second appearance upon exposure to an antiseptic solution. Additionally, the antiseptic indicator is configured to substantially resume the first appearance after a period of time.

Additional features and advantages are described herein, and will be apparent from, the following Detailed Description and the figures.

BRIEF DESCRIPTION OF THE FIGURES

FIG. 3 shows the access device prior to exposure to an antiseptic agent. FIG. 4 shows the access device being exposed to an antiseptic agent by swabbing the access site with an antiseptic cloth or pad. FIG. 5 shows the access device providing a visual indication, such as by a change of color or transparency, that the access site has been exposed to an antiseptic agent.

FIG. 5a shows the access device prior to exposure to an antiseptic agent. FIG. 5b shows the access device being exposed to an antiseptic agent by swabbing the access site with an antiseptic cloth or pad. FIG. 5c shows the access device providing a perceptible indication, such as by a perceptible change of color or transparency, that the access site has been exposed to an antiseptic agent.

FIG. 13 is an enlarged perspective view of the access device of FIG. 2, with cross-sections taken along line 14-14, 15-15, 16-16, and 17-17 where an exposure indicator surrounds the access site.

FIG. 14*a* is an enlarged view of the cross-section taken along line A-A generally showing an exposure indicator in the form of a layer of dye or other suitable indicator disposed on the surface of the housing of an access device.

FIG. 14*b* is an enlarged view of the cross-section taken along line A-A generally showing an alternative embodiment of an exposure indicator, such as a membrane layer impregnated with a color changing material disposed on the surface of the housing of an access device.

FIG. 14*c* is a variation of the embodiment shown in FIG. 14*b*, wherein a membrane is disposed on the surface of the housing of an access device and is impregnated with a hydrogel material containing a dye or other suitable indicator.

FIG. 14*d* is an enlarged view of the cross-section taken along line A-A, generally showing a layer of an exposure indicator material disposed on the housing of an access device, and a membrane disposed over the indicator material.

FIG. 14*e* is an enlarged view of the cross-section taken along line A-A generally showing an intermediate substrate layer disposed on the housing of an access device and an exposure indicator layer disposed on the substrate layer.

FIG. 14*f* is a variation of the embodiment shown in FIG. 14*e*, wherein a permeable membrane layer is disposed on the exposure indicator layer.

FIGS. 23*a* and 23*b* are illustrations of yet another embodiment of an injection molding process that can be used to attach an exposure indicator and an antimicrobial agent to a fluid access device;

FIG. 23*c* is a cross-sectional view of a sprayer head that can be used to selectively apply a coating to a surface of a mold for making a fluid access device.

FIG. 23*d* is a cross sectional view of FIG. 23*c* shown with a core pin inserted into a cavity of the sprayer head.

FIGS. 25a and 25b are perspective views of a fluid access device having a protective member.

FIG. 25c is a cross-sectional view of a an exposure indicator material disposed on a release liner.

FIG. 25d is a perspective view of the exposure indicator and release liner of FIG. 25c.

FIG. 25e is a perspective view of one embodiment of an exposure indicator.

DETAILED DESCRIPTION

Figure 1:
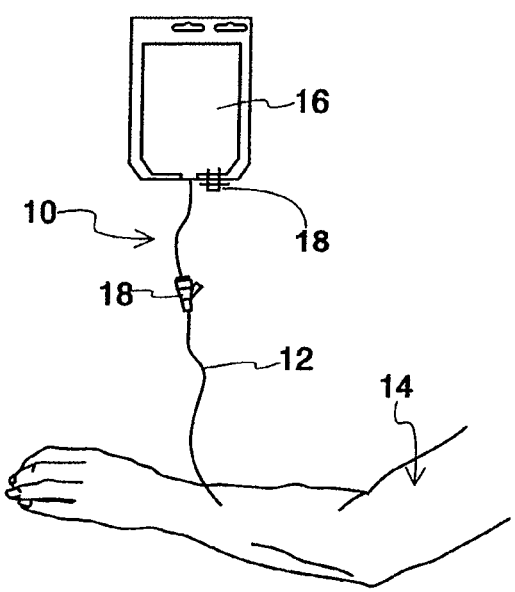
FIG. 1 is a perspective view of a medical fluid flow system in flow communication with a phlebotomized human subject, that includes a fluid access device in accordance with the present disclosure for adding fluid to or withdrawing fluid from the medical fluid flow system.

FIG. 1 generally illustrates a medical fluid flow system, generally at 10. The fluid flow system 10 is illustrated for exemplary purposes only as is an intravenous (IV) administration set. The present invention is not limited to IV flow systems and may be used in association with any apparatus, or container or flow system where fluid access is useful, such as but not limited to administering fluid to or withdrawing fluid from a subject (e.g. patient) or container (e.g. vial or bag).

As illustrated in FIG. 1, the set comprises a length of flexible plastic tubing 12, one end of which is connected via a needle or other access means to a phlebotomized patient (i.e., subject) 14, and the other end is connected to a container 16 of medical fluid, such as intravenous solution or any other medically-related liquid. The tubing 12 of the IV administration set provides a fluid passageway allowing fluid communication between the donor 14 and the container medical fluid source 16.

For introducing fluid into or withdrawing fluid from the flow system, the illustrated IV set 10 includes one or more access devices 18 in accordance with the present disclosure. The fluid access device 18 (or additional such devices) may be provided at any convenient location within the medical fluid flow system, such as along the length of the tubing 12 or attached to container 16. For illustrative purposes, FIG. 1 generally shows one fluid access device at mid-line entry location and one disposed on the container 16. The access device 18 in FIG. 1 may take the form, for example, of the access devices shown in larger view in FIGS. 6, 9 and 11. Such access devices are commonly referred to as V-sites or Y-sites, in reference to their shape, and are typically but not exclusively used for mid-line entry points into fluid flow systems. Again, this is for purposes of illustration only. The fluid access device 18 of the present invention may be a permanent component of a fluid flow set or may be removably attached to a connector member or to a tubing branch, without departing from the present invention—which is not limited to the general form or location of the access device. As mentioned above and shown in FIG. 1, the fluid access device of the present disclosure may also be part of another structure such as a container, e.g., as a vial or bag, into which medical fluid is introduced or from which fluid is withdrawn.

Figure 2:
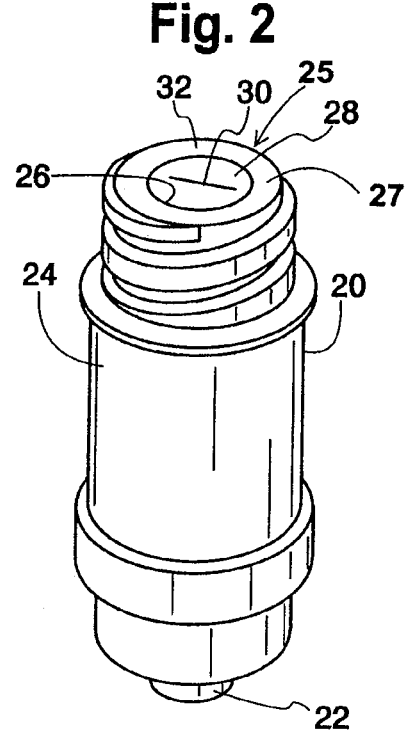
FIG. 2 is a perspective view of one embodiment of a medical fluid access device embodying the present disclosure particularly well suited for attachment to a terminal end of fluid flow tubing, such as at the end of a catheter going into a patient.
Figure 3:
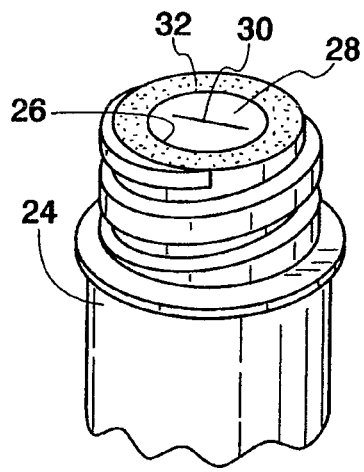
FIGS. 3-5 are a sequence of perspective views of the access device of FIG. 2.
Figure 4:
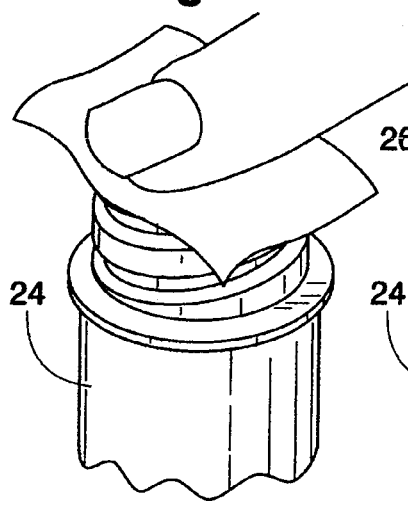

Other shapes and forms of the access device may also be used. For example, FIG. 2 shows another access device 20 in accordance with the present invention that may be located at the terminal end of tubing 22, such as at the external end of an indwelling catheter inserted into a patient's blood vessel. Of course, the access device 20 could also be located at the end of any branch tubing associated with a fluid flow system 10. The illustrated fluid access device 20 has a generally elongated rigid or semi-rigid plastic housing 24 that includes a flow path (not shown) therethrough. The housing 24 material may be constructed of a semi-rigid or rigid medical grade material, such as polycarbonate material for ease of molding and bonding to common medical grade tubing, such as PVC tubing. The housing material may also be constructed of, for example, acrylic (PMMA), acrylonitrile butadiene styrene (ABS), methyl acrylonitrile butadiene styrene (MASS), polypropylene (PP), cyclic olefin copolymer (COC), polyurethane (PU), polyvinyl chloride (PVC) or other suitable material. The housing may be connected at its bottom or distal end to tubing 22 or to an intermediate connector as part of a fluid flow set. An access site 25 for the introduction and withdrawal of fluids can be located at the top or proximal end portion of the access device 20. For example, the access site can be defined by the housing 24 and a gland or valve member 28. The housing 24 can have a generally central circular opening or aperture 26 for introduction or withdrawal of medical fluid through the housing. As noted previously, such medical fluid may include, without limitation, IV solutions, blood and blood components, medications, chemotherapeutic agents, and various other fluids used for various diagnostic, therapeutic or other procedures.

In the illustrated access device, the aperture 26 is closed by the valve member or gland or connector 28 that is preferably made of resilient/elastomeric material, such as rubber, silicone or latex. The valve member normally closes and seals the aperture 26 when it is not being accessed. As used herein, the terms "valve member" and "gland" and "connector" are intended to have broad and generic meanings directed to any member or members for normally closing or sealing the access site and which, in cooperation with an accessing member, allows for entry or access into the access site for introduction or withdrawal of medical fluid therethrough. By way of example only, the valve member or gland may include a solid or slit septum or luer accessible valve. The slit may be formed during molding of the septum or thereafter.

The valve member 28 may be mounted or carried on or in the housing in a variety of ways that are known in the medical field. For example, as noted earlier, the valve member may be a solid rubber, silicone or latex septum that spans the aperture and is pierceable by a needle, or the valve member may include a slit, which is adapted to receive or be opened by a blunt cannula, such as a male luer or specially designed cannula, for introducing or withdrawing fluid, or the valve member may be moveable between the normally closed position and an open position, such as a "luer activated valve" or "luer access device" (LAD), for introduction or withdrawal of medical fluid. This is not an exclusive listing, but merely an indication of the wide variety of valve member constructions that may be employed in an access site employing the present invention.

For purposes of illustration, FIGS. 2-5 show an access device in which the valve member 28 has an opening or slit 30 which is normally in a closed or sealed condition, but which can be forced open by penetration or compression by a blunt cannula or male luer. In this regard, the valve member is preferably of resilient material so that it can be displaced or pierced in any suitable manner to allow access and return to a closed position sealing the aperture 26 and access site 25 when the needle, cannula or luer is removed from the access site.

It will be appreciated that a fluid access device of the type described herein is, in normal usage, exposed to various contaminants or pathogens, such as airborne microorganisms, or by human contact by medical staff or patients. This may cause the surface of the access device to become contaminated with microbes such as bacteria or other harmful microorganisms. To reduce the risk of introducing such microorganisms or other pathogens into the subject, potentially resulting in infection, sickness, or even worse, good medical practice dictates that the clinician clean the access device with an antiseptic agent to kill or reduce the number of pathogens on the access site before administering fluid into or withdrawing fluid through the access site.

In accordance with the present disclosure, the access device 18 includes an antiseptic indicator located at or near the access site. The indicator provides a perceptible indication when the access device has been exposed to an antiseptic agent. The indicator (or absence of a perceptible indication) serves as a deterrent to a clinician who might otherwise fail to observe proper aseptic techniques before introducing or withdrawing fluid through the access device.

As shown in FIGS. 2-5, in one embodiment, the indicator 32 is located on the upper surface 27 at the portion or edge of housing 24 such that when the medical personnel swabs the surface of the valve member 28 the swabbing device also contacts the indicator. In the present embodiment, the indicator 32 surrounds the valve member 28. Accordingly, when the medical personnel swab the surface of the valve member or gland, the indicator is also contacted by the antiseptic agent. Upon exposure to an antiseptic agent, the indicator generates a perceptible indication to the user that such swabbing has occurred. The perceptible indication may be achieved in any suitable manner. It is preferable that the perceptible indication of exposure to the antiseptic agent be generated immediately upon disinfecting or shortly thereafter, for example, within several seconds. The perceptible indication may be a visual indication using visible or other light or may be a indication that is perceptible through the use of an accessory device, for example a bar code reader.

As illustrated in FIGS. 2-5, the visual indication is a color change. The indicator has an original color before it has been exposed to an antiseptic agent, such as blue or purple, and may change to another color, such as red or pink or become transparent from opaque, upon exposure of the indicator to an antiseptic agent, such as by contacting the indicator by swabbing with an antiseptic agent. Where the original color of the indicator is red, orange or the like, it serves as a convenient and conspicuous warning or reminder to the clinician that the surface of the access device has not been properly treated with an antiseptic agent and that the access device should not be used until proper aseptic technique has been carried out. The changed color, such as red or white or other, indicates that the access site has been swabbed with disinfectant agent.

Figure 5:
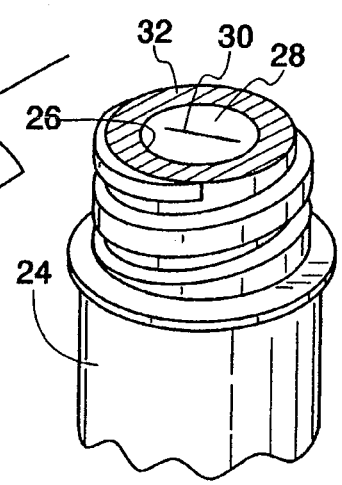
Figure 5A:
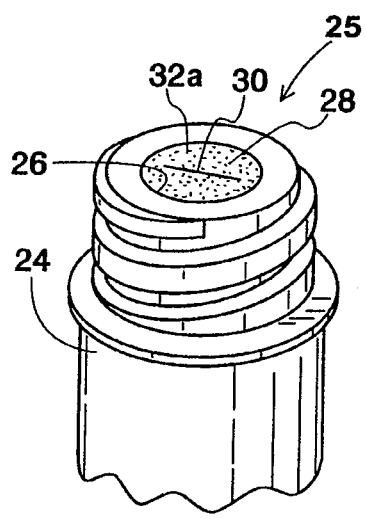
FIGS. 5a-5c are a sequence of perspective views of another embodiment of a fluid access device.
Figure 5B:
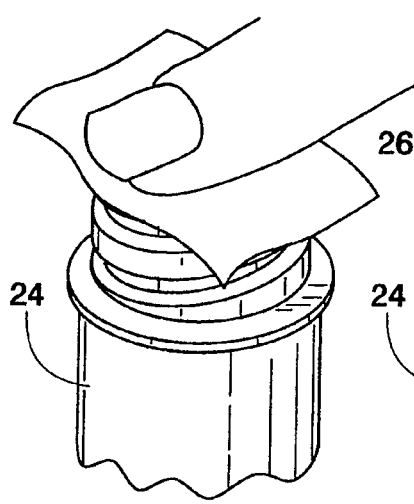
Figure 5C:
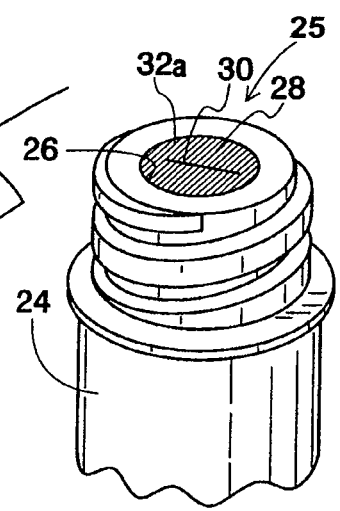

As illustrated in FIGS. 5a-5c, in an alternative embodiment, an indicator 32a can be located on the top portion of the valve member 28. Accordingly, when the medical personnel exposes access site 25 to an antiseptic agent, such as by swabbing with an IPA wipe, the indicator 32a generates a perceptible indication to the user that proper disinfecting has occurred.

Referring to FIGS. 3-5 and 5a-5c, the clinician may treat the surface of the access device with an antiseptic agent by direct contact such as spraying, wetting, wiping or swabbing the gland and surrounding housing with a disinfectant or sterilizing agent. The antiseptic agent is typically contained in a cloth, tissue, cotton swab or the like, and by swabbing. Suitable sterilizing agents may include standard rubbing alcohol (isopropyl alcohol (IPA)), a 70% IPA solution or solution of IPA and chlorohexidine or any other suitable antiseptic agents for killing bacteria or other pathogens.

A visual indication in the form of a color change may also serve as a perceptible indication to the clinician of the quality and thoroughness of the antiseptic treatment, such as proper swabbing surface coverage, proper swabbing force and/or pressure to the surface. For example, if aggressive antiseptic treating has taken place, the color change of the indicator may be of greater difference or intensity. More specifically, for example, if the indicator changes to red upon exposure to an antiseptic agent, the vividness or shade of the red color could indicate the extent of exposure. Dark or bright red could indicate that the access site has been aggressively treated with antiseptic agent or contacted with antiseptic agent over an extended period of time. A lighter or paler red might indicate a less aggressive treatment and signal the nurse or other clinician that further swabbing or wiping is necessary or would be useful.

Figure 12:
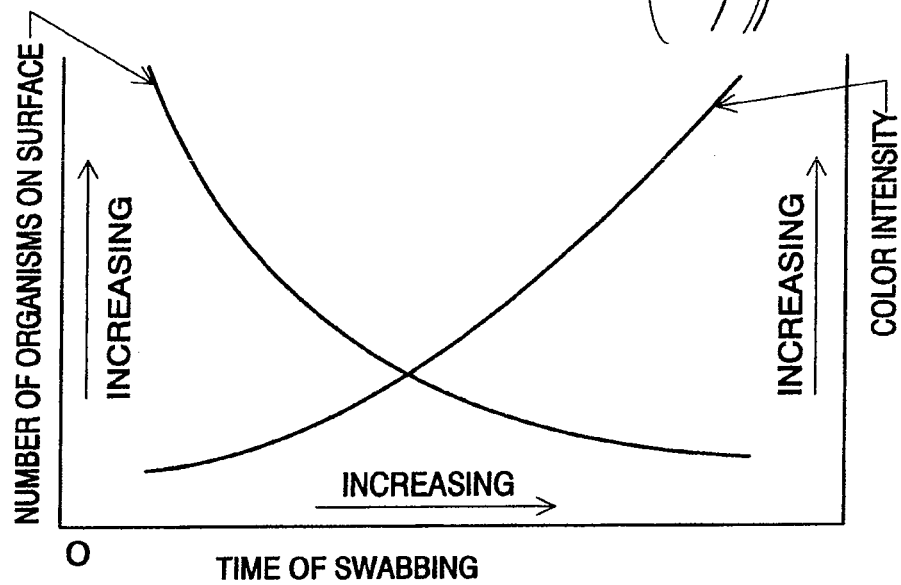
FIG. 12 is a graph generally showing a correlation between the time of swabbing the surface of an access device of the present disclosure with antiseptic agent, the reduction in the number of organisms on the surface of the access device, and the change in color intensity of a visual indicator that changes color upon exposure to an antiseptic agent.

Another factor that may affect the quality or thoroughness of antiseptic treatment is the duration of the treatment. FIG. 12 illustrates one possible correlation between the swabbing time of a surface of an access device with antiseptic agent, the reduction in the number of organisms on the surface and the change of color intensity of an antiseptic indicator. As the swabbing time increases, the number of organisms decreases and the color intensity of antiseptic indicator increases. A dark or bright color indicates that the swabbing time has been sufficient to kill or eliminate the majority of organisms on the surface. A lighter or paler color indicates that swabbing time may not have been sufficient and that further swabbing is necessary or would be useful.

It will be appreciated that the effectiveness of the antiseptic agent is only temporary, as the access device may become re-contaminated from exposure to the air or from human contact. As such, it is preferable that the perceptible indication, such as a color change, be temporary and of limited time duration, and that the access site return to its original or another color at some time after disinfecting—for example, several seconds to several minutes, such as about five seconds to 1 minutes, 1-2 minutes, 3-10 minutes or 5-10 minutes or such other time as may be desired after disinfecting. By reverting to the original condition or color, the indicator serves to remind the clinician to re-swab the access device with antiseptic agent before it is used again.

Figure 7:
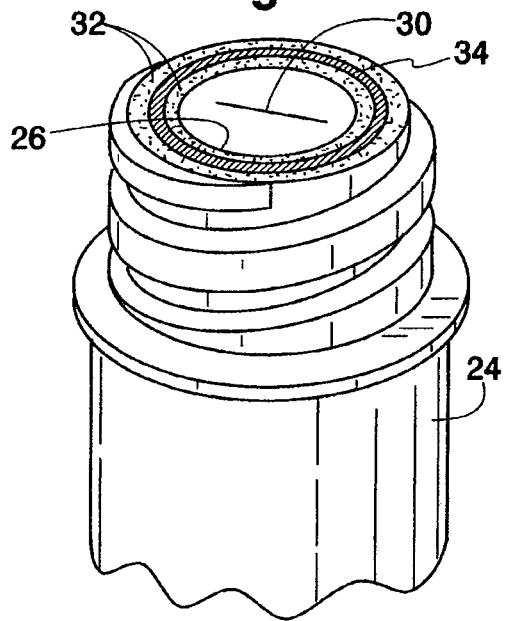
FIG. 7 is a perspective view of another embodiment of a medical fluid access device of the general type shown in FIG. 2, and comprising a ring of a fixed reference color disposed on the access device for comparison by the user to evaluate a color change of the indicator when exposed to antiseptic agent.
Figure 8:
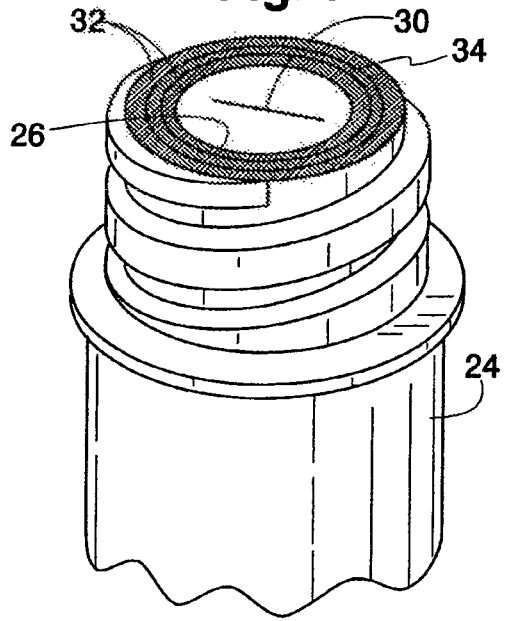
FIG. 8 is a perspective view of the access device of FIG. 7 after the access device has undergone swabbing or other contact or exposure to an antiseptic agent and after the indicator has become substantially identical in color to the fixed reference color to indicate to the user that the access site has been disinfected in accordance with proper medical practice.

As seen in FIGS. 7 and 8, which are a variation on the embodiment of FIGS. 2-5, it may also be desirable to include a fixed reference indicator, such as a color, disposed on the gland or housing or both of the access device. As shown in detail in FIG. 7, the fixed reference may be a color in the form of a ring 34 or other similar marking of color on the access device. The reference color preferably is a color that is substantially similar to the color of the indicator after exposure to an antiseptic agent. In the illustrated access device, if the indicator turns red upon exposure to an antiseptic agent, the fixed reference color may be a red ring disposed near the access site, although the reference color could be at a location elsewhere on housing 24 significantly spaced from the access site. As shown in FIGS. 7 and 8, indicator 32 is a pair of rings flanking the reference ring 34 so that the colors may be easily compared and the indicator rings will be simultaneously contacted with antiseptic agent during swabbing. Swabbing is typically directed primarily at the gland and surrounding housing portions which may be contacted by the luer, cannula or needle for adding or withdrawing fluid through the access site. Thus, when the indicator is located on the housing, it is preferably located closely adjacent to the gland so as to contact the antiseptic agent to the same general degree as the gland.

With the above arrangement, if the indicator rings are, for example, red before the access device is swabbed with antiseptic agent, and the reference ring were red, the access device would have red, red and red rings around the gland prior to swabbing, thereby alerting the user to the need to disinfect the access site. After swabbing with an antiseptic agent, the red rings would turn red and the visual indication would appear as generally a single, wide red ring around the gland—until such time as the indicator rings 34 returned to their original red color or other non-red color.

The perceptible indicator of the present invention may also include a feature or aspect that facilitates visual indication to a clinician who is color-blind or otherwise color-sight impaired. For example, if the visual indicator is a change of color, the change of color may have associated with it a pattern or arrangement that is visible to a color-impaired clinician. For example, the color change may be from a solid color to a color of having a pattern discernible to the impaired clinician, or vice versa. Alternatively, colors may be specially selected such that the color change employed by the indicator are detectable even by a person who is color-sight impaired.

The indicator of the present invention may be made in a number of different ways. In an optimal configuration, the indicator would actually be sensitive or reactive to presence of micro-organisms or other contaminants and would also generate a visual indication when the surface of the gland and surrounding housing are substantially free of contaminants or microbes. In combination with an indicator of the present disclosure, one or more of the housing, gland or indicator may also include an anti-microbial coating, or an anti-infective agent attached, coated, or impregnated therein. Alternatively, or in addition to an anti-microbial coating on the housing, chlorhexidine gluconate can be added to the antiseptic agent used in the swabbing or included in the housing or gland or membrane of the access device as an additional antiseptic precaution.

As indicated earlier, the indicator may be one or more of several types of indicators that operate on different principles. Preferably, the indicator will generate a perceptible indication in response to contact with an antiseptic agent, such as isopropyl alcohol.

Figure 6:
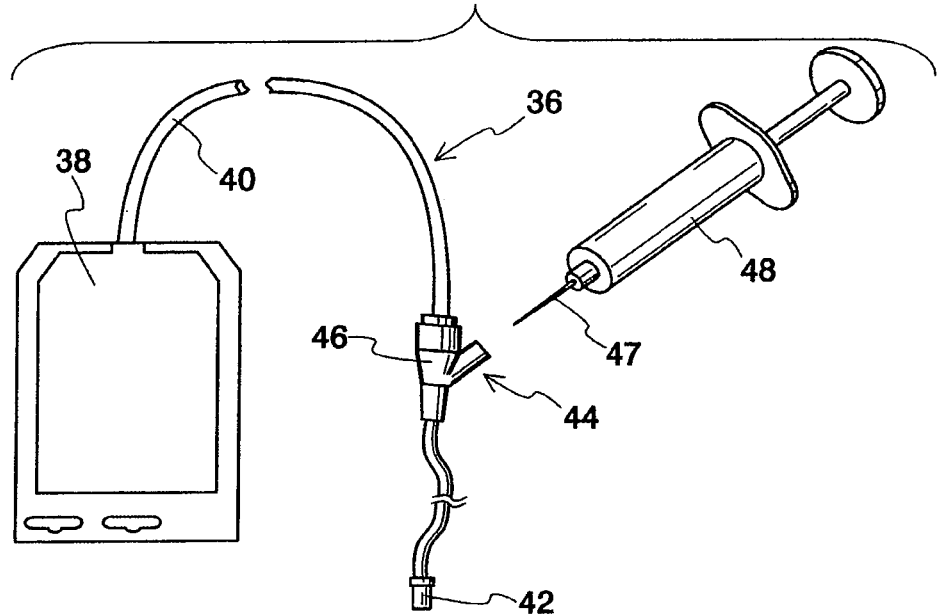
FIG. 6 is a perspective view of another embodiment of the access device of the present disclosure as part of a medical fluid flow system, with fluid about to be added to or withdrawn from the flow system through the access device by a syringe with a needle.

FIGS. 6 and 9-11 show other types of access sites in which the present invention also may be employed. FIG. 6, for example, illustrates a medical fluid flow system, generally at 36, having a medical fluid container 38 and flexible plastic tubing 40 extending between the container 38 and a terminal connector 42. The system 36 includes an access device 44 that has a housing 46 and gland (not visible) with an indicator for indicating exposure to an antiseptic agent. The access device 44 is of the type that employs a solid septum, such as rubber, latex, or silicone, that is accessed by piercing with a needle, such as needle 47 attached to syringe 48. Examples of such an access site may be seen in U.S. Pat. Nos. 4,048,995 and 4,219,912, which are hereby incorporated by reference herein. Moreover, the access device may be attached to a short length of tubing 40 connected to the container 38 and is frequently referred to as a port tube and by way of example maybe be an administration port, a medication port or a port which allows the addition and/or withdrawal of fluid from the container.

Figure 9:
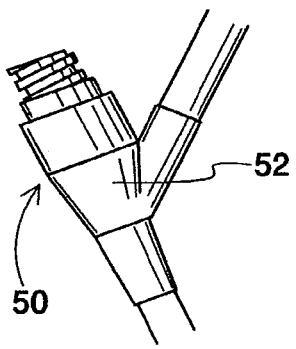
FIG. 9 is a side view of another embodiment of the access device of the present disclosure particularly suited for mounting in-line or mid-line in association with a fluid flow system.
Figure 10:
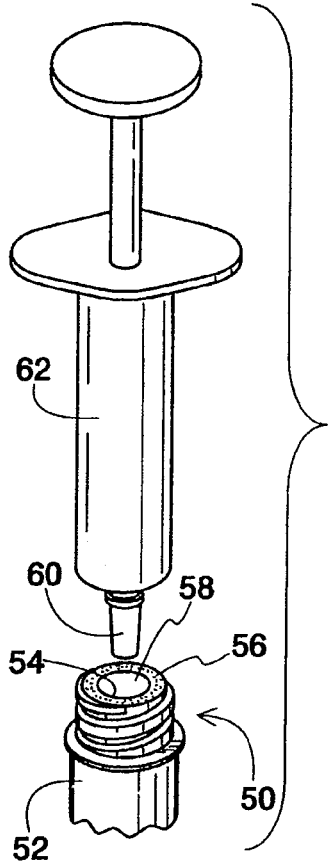
FIG. 10 is a perspective view of the access device of FIG. 9 about to receive a male luer end of a syringe for introduction or withdrawal of medical fluid.

FIGS. 9 and 10 illustrate an access device 50 having a substantially rigid housing 52 having an opening or aperture 54 defining an access site and an indicator 56 for indicating exposure to an antiseptic agent. The device may further include a gland 58 for normally closing or sealing the aperture 54. There may be certain circumstances where the access site is not closed by a gland, but in most typical applications, a gland will be employed.

The access device of FIGS. 9 and 10 is a LAD-type device, for access by a male luer, and the gland 58 is depressed by contact with a standard male luer, such as the luer 60 illustrated on syringe 62, to open the access device to flow therethrough. Examples of this type of access site may be found in U.S. Pat. Nos. 6,682,509, where depression of a seal causes it to be pierced by an internal spike; 5,360,413, where depression of a piston accesses fluid passageways for flow through the access device; and 5,782,816, where compression of the valve element causes it to cant, permitting fluid flow through the device. All of the above patents are incorporated by reference herein and are intended to demonstrate that the present invention is not limited to the particular internal design or construction of a given access device, and that it has utility across the entire spectrum of access devices that are now or may later be employed in infusion therapy and in particular in medical fluid access or flow systems.

Figure 11:
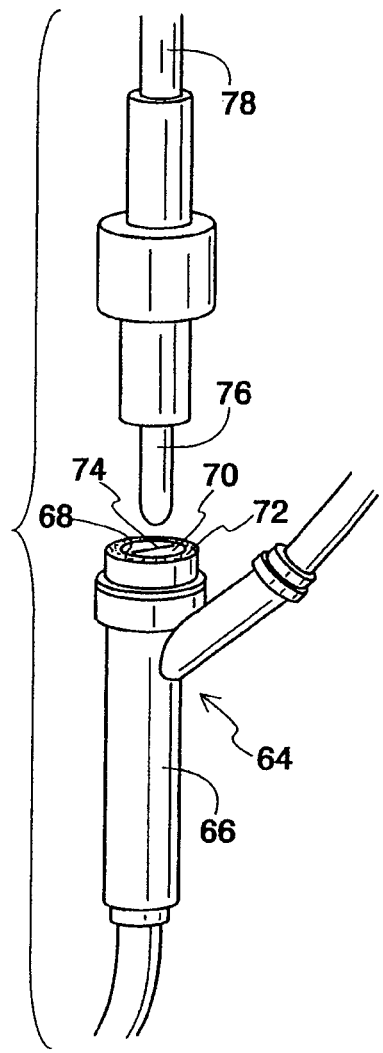
FIG. 11 is a perspective view of yet another embodiment of the fluid access device of the present disclosure located midline in a fluid flow path and adapted to receive a specially designed blunt cannula for introduction or withdrawal of medical fluid.

In this regard, FIG. 11 illustrates a fluid access device 64 in accordance with another embodiment of the present invention and including a housing 66, an aperture or opening 68 in the housing defining an access site, a gland 70, normally closing and sealing the aperture, and a visual indicator 72. This access device has a preformed but normally closed opening or slit 74 for receiving a blunt cannula 76 of a connecting fluid flow system 78. The blunt cannula may be a specially designed cannula, such as described in U.S. Pat. No. 5,135,489, incorporated by reference herein, or may be a standard male luer or other member as illustrated, for example, in U.S. Pat. No. 6,669,681, also incorporated by reference herein, Finally, it should be noted that the access device of the present invention does not need to be a separate device, and the access device housing may also be formed as part of another structure, such as in the form of the neck end of a medical fluid vial, a port on a stopcock or any other structure that defines an access opening into a container, a fluid flow system or other structure for the introduction or withdrawal of medical fluid therethrough. For example, the present invention may be particularly useful on medical vials. Such vials are commonly glass or plastic containers with an open top or neck defining an opening or access site that is generally sealed by an gland such as a rubber or silicone stopper or septum. The visual indicator of the present invention may be employed on the gland, or on a surrounding portion of the vial or closure structure, or both, so as to indicate to the user when the stopper or septum has been properly swabbed with disinfectant before the stopper or septum is punctured or otherwise accessed for withdrawal of contents from or introduction of fluid into the vial.

Color Changing Coatings

In one embodiment, as seen in FIG. 14a, the indicator may comprise a polyacrylic coating 80 or film that changes color in the presence of an antiseptic agent and is bonded, for example, by covalent or Van der Waals attraction, to the polycarbonate housing 24 of the access device. The polyacrylic coating 80 may be, for example a solvatochromic dye that reacts to the polarity of the antiseptic solution. The molecular structure of one example of an exposure indicator comprising a dye coating that may be disposed on the surface of an access device includes:

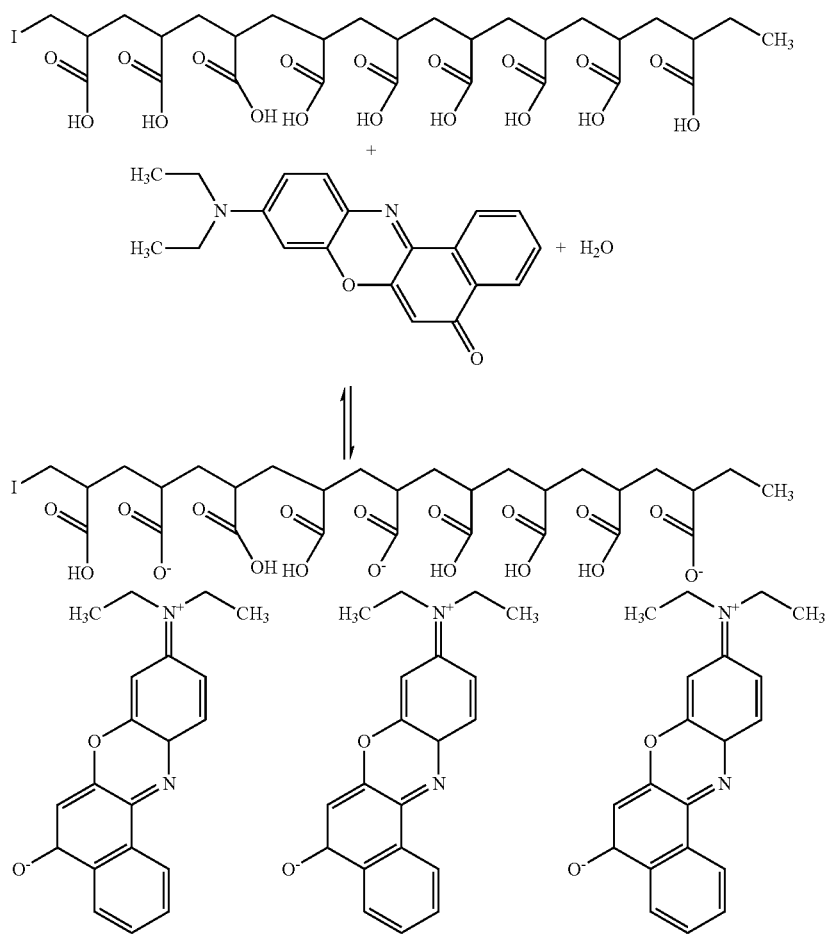

For a coating application of an exposure indicator 80 to polycarbonate substrates such as the housing of an access device 24, for example, the use of a combination of an acid and a salt such as polyacrylic acid and Nile Red and its derivatives may be incorporated in a antiseptic solvent-absorbing polymer matrix which has yielded a blue to pink color shift in the presence of a polar solvent such as isopropanol.

Alternatively, a color changing dye could actually be incorporated into at least a portion of the material that comprises the access device during manufacture. This is achieved, for example, by saturating the material that is used to construct the gland or "boot" portion of the fluid access device with dye that is reactive to exposure with an antiseptic agent. As discussed previously, the gland may be comprised of silicone, rubber, or similar elastomeric material, which is disposed within the housing of a fluid access device. The dye may be incorporated into the silicone, for example, during molding of the material, or alternatively, the silicone boot may be stained or "imbibed" with dye by placing the boot in a dye containing solution. The housing of the access device is then assembled with the dye-containing boot disposed within the housing.

To extend or control the length of time that the visual indication takes place, the dye may be incorporated in an antiseptic solvent-absorbing polymer matrix material. The antiseptic solvent-absorbing polymer matrix absorbs the antiseptic agent and prolongs contact between the agent and dye so that the visual indication may continue for a more extended time than otherwise. Binding the Nile Red and its derivatives with polyacrylic acid, helps to prevent the unintentional removal of the dye as a result of swabbing of the access site. Potential variants of this approach include the use of agents in the exposure indicator that detect a pH shift or chemical change from the antiseptic agent during swabbing to produce a color change.

Porous Structures with Dyes Therein

In another embodiment, as shown in FIG. 14b, the exposure indicator may comprise a dye encapsulated in or carried by a porous structure 82, such as a membrane. The membrane 82 may be for example, a micro-porous membrane or an ultra-filtration membrane. The pores of the membrane can absorb and retain antiseptic agent during swabbing, thus increasing the duration of contact between the antiseptic agent and the dye that is encapsulated within the membrane. Pore size, pore structure, surface tension, skin layer thickness and density are factors to control absorption, evaporation rate and retention of the antiseptic agent allowing the membrane to therefore serve as a permeable selective layer. The longer the antiseptic agent is retained within the membrane 82, the longer the duration of color or other visual change of the indicator will be maintained. In one embodiment, the pore size of the membrane is about 1 lam or less and in another embodiment, the pore size is about 0.2 µm or less. Membranes that have pores sizes of about 0.2 µm or less are IPA permeable and the small pore size assist in preventing bacteria from entering the microporous structure of the membrane. Additionally, the porosity of the membrane can be between about 10% and about 40%.

The membrane 82 may be constructed in various ways. In one embodiment, the membrane is formed separately from the manufacture of the housing of the access device. For example, a microporous polycarbonate membrane embedded with dye may be formed by a phase inversion process. In this method, the membrane is cast as a separate film or grown on a solid surface such as a glass plate or a liquid surface in several steps. First, a polymer and a dye are dispersed in a solvent. The solvent can be, for example, cyclohexane, toluene, THF, acetone, cyclohexanone, methylene chloride, NMP (N-methylpyrrolidone), ethylene chloride, and/or water. The solvent is then evaporated by various methods, including increasing the temperature of the solvent or by increasing the gradient of vapor pressure. Alternatively, the solvent can be removed by other methods, such as by employing a second solvent solution. This causes the polymer to coagulate and solidify into a substantially solid porous structure. By controlling the evaporation rate of the solvent and the coagulation rate, characteristics of the porous membrane, such as skin layer thickness and density, pore size, and pore structure can be controlled. Once the membrane 82 is formed, it can then be attached to the surface of the housing 24 (or the gland 28 if desired). Such attachment may be achieved by various means, including, for example, sonic welding or adhesive. The attachment may also be formed using decorative or insert molding techniques which include introducing the membrane 82 into the mold for the housing 24 prior to the molding of the housing.

Alternatively, the membrane may be directly formed on the housing of the access device 24. This is accomplished by preparing a membrane as described above by the phase inversion process. Dye is added to a polymer solution containing a solvent. The polymer solution is preferably made with the same polymer that is used for the construction of the housing. The housing of the access device can be contacted with the solution, such as by "dipping" into the solution, and the solvent contained in the polymer solution will dissolve the surface of the housing. The membrane with encaptured dye will thus be formed on and bonded directly on the surface of the housing.

Encapsulated Dyes

In another embodiment, as seen in FIG. 14c, the active agent in the indicator, such as a dye or other agent, can be encapsulated in another material 84 which is embedded in a membrane, or chemically cross-liked to other materials. For example, dye can be captured in an antiseptic solvent-absorbing polymer matrix during the polymerization of the antiseptic solvent-absorbing polymer matrix. For non-reactive dyes, the dye can be trapped in the antiseptic solvent-absorbing polymer matrix after the antiseptic solvent-absorbing polymer matrix is polymerized. For reactive dye, the dye structure can become part of the polymer segment itself. Potential dye containing materials include, for example, crosslinked copolymer of urethane acrylates with polyvinyl pyrolidone or dimethyl acrylamide.

Again, as described above, the antiseptic solvent-absorbing polymer matrix is a generally absorbent material, that can absorb and "swell" with antiseptic agent. A membrane that includes a hydrogel material will provide a longer retention of antiseptic agent. This, in turn, increases the duration of contact of the antiseptic agent with the exposure indicator, thus increasing the duration of the visual indication.

Alternatively, hydrogel beads with encaptured dye can be mixed into a polymer solution such as polycarbonate or PVDF when synthesizing a porous membrane In this way, dye-containing beads 84 can be embedded in the membrane 82 during the synthesis and formation of the membrane.

Other Variations

Other variations may include cross-linked solvent-absorbent polymers, placing the dye in an acrylic polymer, using thermal cure types of emulsion carriers for the dye, or employing lacquer carriers for the dye or employing substrates (such as silicone) to hold the dye in the substrate matrix. The dye could potentially also be suspended in a matrix of adhesive or secured by two-shot molding of film to a polycarbonate or other housing substrate of the access device.

The indicator of the present invention could also include a liquid crystal material that changes color upon a temperature change from contact with the antiseptic agent. The liquid crystal material may be suspended between layers of film, such as polyester film, to capture the material. Such material may be present in the form of micro-capsules. The film may then be attached to the access device housing, which may be of polycarbonate material, by cyanoacrylate adhesive or other bonding agent or method. Alternatively, the liquid crystal material may be suspended in an impregnated substrate or contained in a coating applied to the access device. An alternative to liquid crystal materials are thermochromic dyes, which change color due to a temperature change. Such dyes could be employed as described above. Such an indicator allows for quick color change which is also reversible back to the original color in minutes.

Yet a further variation of the indicator is the use of a pressure-sensitive material, such as liquid crystal microcapsules, which change color as a result of pressure exerted by the clinician during swabbing. The microcrystals may be suspended between layers of film, such as polyester film, to capture the material. Such microcapsules may exhibit a single color change and may not be reversible. Accordingly if reversibility of the color change is desired, other pressure sensitive materials or mechanisms may be employed.

Layered Structures

In another embodiment, as seen in FIG. 14d, a layer 86, which may be porous or permeable, may be disposed over the exposure indicator. In this embodiment, the exposure indicator may comprise a layer of dye 80 or other suitable indicator material disposed on the housing 24, including a dye-containing membrane 82 disposed on the housing 24. A permeable layer 86 or cover is then disposed over the indicator material. In one example the layer 86 could be a clear porous material such as cellulose acetate or thin polycarbonate film disposed over the exposure indicating material. The exposure indicator would therefore be "sandwiched" between the surface of the housing of the access device 24 and the permeable layer 86. Attachment of the permeable layer 86 to the layer of exposure indicator may be achieved by solvent bonding, heat, adhesive, or sonic welding.

Such a coating over the indicator may serve various purposes, such as to provide a protective layer over the indicator, control absorption and evaporation of antiseptic agent and/or provide a layer of selective permeability, without unduly interfering with a visual indication of swabbing with an antiseptic agent. In fact, a permeable membrane may actually encourage a more effective antiseptic swab technique by a clinician for the reason that the clinician may be required to swab with greater deliberate and consistent pressure across the surface of the access device so that antiseptic agent from the swab permeates the membrane and reaches the exposure indicator thereunder.

In the event that the exposure indicator layer comprises a dye-containing membrane, it may be desirable to provide a permeable layer with a pore size different than the pore size of the underlying membrane layer of exposure indicator, creating a "differential porosity" between the exposure indicator and the overlying permeable layer. For example, the pore size of the overlying permeable layer may be smaller than the pore size of the underlying layer of exposure indicator. Thus, evaporation of antiseptic agent from the exposure indicator would be slowed and the time of contact between the exposure indicator and the antiseptic agent would be increased. This will generally provide a longer duration of visual indication, for example, a change in color of the exposure indicator would be maintained for a longer period of time. This would ensure a clear and conspicuous indication of a proper antiseptic swab to the clinician. A covering membrane of substantially smaller pore size may also retard escape or extraction of dye or other material from the underlying indicator.

Transparency Changing Antiseptic Indicator

In another embodiment, the perceptible indication may comprise a visible change in transparency. For example, as seen in FIG. 14e, an exposure indicator 88 may be disposed on a portion of the housing, the gland, or both, and undergo a change in transparency upon exposure to an antiseptic agent. For example, dry (air filled) microporous structures appear white to the observer even when the strands comprising the microporous structures are transparent. It is believed that reason for this is the mismatch between the refractive index of the solid strand of material and the surrounding air. If the air is replaced by another fluid with a refractive index identical to or very close to that of the strand, the structure will appear transparent to the observer.

Additionally or alternately, the fluid that replaced the air can have a light wave guidance property that guides and bends light through the porous structure. The light wave guidance property also can assist in causing the porous structure to appear transparent. In an embodiment the microporous structure is composed of a material and is of a construction which will distinguish between an antiseptic fluid and water. For example the porous structure may be constructed of a material and include a microporous structure which is hydrophobic to resist the penetration of water into the porous structure but allows the penetration of alcohol and subsequent replacement of the air within.

Various polymeric materials can be used as an exposure indicator in which a noticeable change in transparency will occur upon wetting with an antiseptic agent. Preferably, several of such materials have a refractive index within a range approaching or approximating that of the typical antiseptic agent. For example, polymeric materials having a refractive index in the range of 1.25 to 1.6 may be particularly suited to this embodiment. Other of such materials may be hydrophobic but allow the absorption of antiseptic fluids. Materials having a refractive index in the above described range and/or hydrophobic/absorption properties include, but are not limited to: polytetrafluoroethylene, ethylene tetrafluoroethylene, polychlorotrifluoroethylene, polydimethylsiloxane, polyvinylidene fluoride, polyvinyl acetate, cellulose acetate, ethylene vinyl acetate copolymer, poly methyl methacrylate, polypropylene, polyethylene, polyacrylic acid, polyvinyl chloride, and polycarbonate.

In use, it is desired that the antiseptic fluid penetrate the structure thoroughly if it is to wet all strands. One can use this phenomenon as a visual signal of good wetting by a known fluid. For example ePTFE and 70% IPA have almost identical refractive indices. Thus, when a microporous ePTFE membrane which is white or opaque to the eye when dry, is wetted by swabbing with a 70% IPA, the membrane becomes transparent, and the underlying color or predetermined visual signal, such as a color or printed message or image, will be visually discernible. In one embodiment, the printed message or image could be printed with an invisible ink which is only visible under a particular wavelength of light, such as inks that are only visible under a blacklight. In a further embodiment, the printed message or image could be color thermal print or a holographic print.

If the user tries to swab with a fluid which does not provide effective swabbing, which by way of example may be water, blood, infusion solutions or drugs, the ePTFE membrane will not wet, and will remain white. Such fluids may interfere with the indicating properties or provide a medium for the growth of infectious agents. In this regard, the material can be inherently hydrophobic or it also may be desirable to provide a hydrophobic coating on or over the exposure indicator layer to substantially prevent a change in transparency in the presence of water. Such hydrophobicity can be described for purposes of this description as any material which is wettable by alcohol, and not wettable by water. In this way, water may be rejected or segmented out by the hydrophobic coating, while only the antiseptic agent will wet the microporous membrane.

The visual indication provided by the above-described change in transparency has particular advantages. First, it is purely physical in nature and does not rely on incorporated dyes or pigments and is not subject to extractables of any kind. Also, the swabbing fluid that includes 70% isopropyl alcohol can be used effectively to create a visual indication of swabbing with materials that have a long history of use in medical deices. Alternatively, materials which have a refractive index similar to chlorhexidine in 70% IPA which is also used as a swabbing agent.

Such a microporous structure may be carried or mounted on the gland or housing or both in any desired manner. If provided as a separate member, the microporous structure could be in the form of a membrane or other structure, with an adhesive backing 90 that may be attached to the housing or gland using ultrasound, adhesive, heat binding or other techniques. The structure may also be applied to the housing decorative molding techniques.

The microporous membrane can be a PE or ePTFE microporous membrane that is made from a process that includes stretching. The membrane can have a thickness between about 12 μm and about 0.13 mm. The membrane also can have a pore size of about 1 μm or less, and in one embodiment, the pore size is about 0.2 μm or less. A pore size 0.2 μm or less allows IPA to permeate the membrane but substantially prevents bacteria from entering the membrane. The membrane can also have a porosity of between about 10% and about 40%. In one embodiment, the membrane is a PE membrane having a thickness of about 25 μm, a porosity of 40% and a mean pore size of about 0.1 μm, such as Sulupor® 14P01E commercially available through DSM Solutech, The Netherlands In an embodiment, the microporous material is an ePTFE material having a polyester, polyethylene or polypropylene mesh support which facilitates attachment to the housing. In particular such mesh facilitates sonic welding or attachment by liquid adhesive of the material to the surface. Additional layers of polyester mesh may be used to aid in the attachment of the microporous material to the housing. Membranes having a polyester mesh support are commercially available.

The change in transparency may itself be a perceptible indication to the user, or the microporous structure may be used in combination with a perceptible signal source. When in a substantially non-transparent state, the microporous structure may serve to obscure the perceptible signal source, such as a source that is situated therebelow. Such a signal source may be, for example, a particular color, a text message, a bar code or other computer readable image, an icon, or other indicator that, when revealed, would provide an indication to the clinician that the access device has been exposed to antiseptic agent. Conversely, when the signal source is obscured by the non-transparent state of the indicator, the clinician will be alerted to the fact that the surface of the access device has not been treated with antiseptic agent. Accordingly, as the microporous structure dries, it returns to a non-transparent state, alerting the clinician to swab the access device before using it again. The reading of the signal source by a reader may then produce a signal which is fed into a medical information system or database to verify and produce a historical record of the swabbing before administration. For purposes of the present invention, it is not necessary that the refractive indexes of the antiseptic agent and the membrane be so close that complete transparency occurs (although that may be preferred). It is sufficient if the change in transparency is sufficiently noticeable to the user to permit its use as an indicator or contact with an antiseptic agent.

In a further embodiment a layer of the microporous structure may be applied to a layer of the indicating material which also displays a perceptible, visual signal when coming into contact with the swabbing fluid. Thus the outer layer becomes transparent and an intermediate layer visually indicates that the swabbing has occurred.

In a further embodiment, the degree of transparency exhibited may be controlled such that the desired degree of transparency only occurs upon a desired level of swabbing. By way of example, a visual indicator such as a bar code may not be visible with a required degree of readability without the membrane being sufficiently wetted or swabbed, this required degree being imposed by the bar code reader. One method of achieving this control is to provide two or more layers of the membrane which require the desired swabbing before the needed transparency is achieved. Another method is to select a membrane with a specific pore size which affect the degree of transparency and also may provide a sterilizing membrane by filtering out pathogens from penetrating through the membrane prior to or after use of the device.

In another embodiment, the adhesive layer 90 can be dyed or colored so as to perform the dual function of (1) adhering the exposure indicator 88 to inlet portion of the housing and (2) serving as a visual indicating material that is displayed when exposure indicator 88 changes from an opaque or substantially opaque state (i.e., a non-transparent state) to the at least partially-transparent state upon exposure to an antiseptic agent. For example, exposure indicator 88 can be any suitable transparency changing indicator, such as the microporous membranes and microporous particles as described herein. Furthermore, the adhesive layer 90 can be an adhesive that has a natural color or an adhesive that has been dyed to obtain a desired color. The adhesive/dye combination can be any suitable adhesive/dye combination for medical use and can include a variety of colors. For example, in one embodiment, the dyed adhesive includes ethylene-vinyl acetate (EVA) that is colored with an EVA based or polyethylene based dye or other suitable dye.

While in the non-transparent or opaque state, the exposure indicator 88 obscures or hides the color of adhesive layer 90 so that it is not visable to the user. As described above, upon exposure to an antiseptic agent, such as by swabbing with a 70% IPA solution, exposure indicator 88 becomes more transparent so that the color of adhesive layer 90 can be visually observed through the exposure indicator 88 thereby indicating that the device has been exposed to an antiseptic agent.

Using a colored adhesive provides many benefits. For example, the color of the visual indicating material does not depend on the color of the housing. Therefore, a greater number of different colored housings can be used, and a greater selection of colors can be used as the visual indicator. For example, a colored adhesive can be used as a visual indicator on a clear housing. Additionally, if a particular color is desired as the visual indicator, the adhesive layer can be dyed to that color.

The adhesive may also include a distributed reflective substance such as "glitter" either alone or in combination with the color additives. Upon exposure to the antiseptic agent, light is transmitted through the membrand and is then reflected back off the substance and provides a perceptible indication or contributes to the perceptible indication that the device has been exposed to an antiseptic agent.

Permeable Layers

In an alternative embodiment, as seen in FIG. 14*f*, an additional permeable layer 92 is disposed over the exposure indicator 88 shown FIG. 14*e*. In an example, layer 92 is porous or permeable and is disposed on the indicator layer 88, which can be a clear porous material such as cellulose acetate or polycarbonate film. As with the embodiment in FIG. 14*e*, exposure indicator 88 of this alternative embodiment undergoes a change in transparency upon exposure to an antiseptic agent. The structure of this embodiment generally includes four layers—the uppermost layer being the permeable layer 92, which may be disposed on the exposure indicator layer 88, which, in turn, may be disposed on a substrate layer 90, which, in turn, may be disposed on the surface of the access device 24. The substrate layer 90 and the exposure indicator 88 are therefore "sandwiched" between the surface of the housing of the access device 24 and the permeable layer 92. Attachment of the permeable layer 92 to the layer of exposure indicator 88 may be achieved by various methods such as sonic welding.

Permeable layer 92 over indicator 88 serves various purposes, such as to provide a protective layer over the indicator, control absorption and evaporation of antiseptic agent and/or provide a layer of selective permeability. For example, permeable layer 92 in one embodiment includes a polycarbonate, having a 0.20-micron pore size. The surface of the permeable layer 92 can be generally smooth in texture, so that it deters harmful microbes or bacteria from collecting on the surface of the access device near the access site.

Permeable layer 92 allows the indication of proper swabbing to be verified. The smooth surface may actually promote a more effective antiseptic swab technique by a clinician because the clinician may be required to swab the surface with greater deliberate and consistent pressure so that the antiseptic agent from the swab can permeate the permeable membrane 92 and reach the exposure indicator 88 under the membrane.

Antiseptic Indicator with Microcracked Surface

In another embodiment, an appearance changing indicator includes a microcracked surface layer, i.e., fine, small cracks on the surface. The microcracked surface has a first appearance prior to being exposed to an antiseptic agent and a second appearance upon exposure to an antiseptic agent. The appearance of the microcracked surface can change from opaque to transparent or can change from a whitish matte color to a different or non-whitish color. Furthermore, the microcracked surface layer can be a surface of the fluid access device housing or a surface of a material attached to the housing.

The microcracks or microstructures on the surface reflect and scatter light in all directions, giving the surface a white matte appearance. Upon wetting of the microcracked surface, the antiseptic agent interacts with the surface so that the scattering and reflection of light caused by the microcracks ceases and the surface changes from the white matte color to the original color of the surface material. This color change indicates that the surface has been exposed to an antiseptic agent.

Figure 15A:
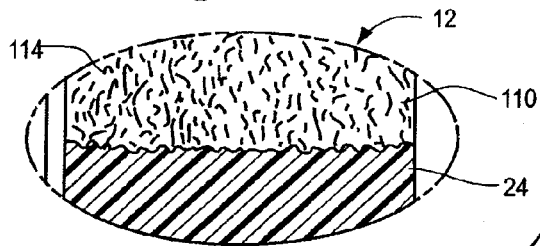
FIG. 15*a* is an enlarged perspective view taken along line A-A of FIG. 13, generally showing an alternative embodiment of an exposure indicator, such as a crazed surface of the housing inlet.

For example, as illustrated in FIG. 15a, the surface 110 of the inlet port of housing 24 includes an antiseptic indicator 112 that has microcracks 114 located in surface. The microcracks give the surface of the housing a whitish, matted or dull appearance. When surface 110 is exposed to an antiseptic indicator, such as by swabbing with EPA or a solution of 70% IPA, the IPA or water/IPA solution wets the surface and the surface appears to be the same color as the housing material.

The microcracked surface of the housing described above and other microcracked surfaces described herein can occur inherently or naturally in the surface, or the microcracks can be induced chemically or mechanically. For example, it is well known that microcracks can be created on the surface of a polymer substrate by exposing the surface to a solvent that penetrates into the polymer matrix. As the solvent penetrates into the polymer, the matrix of the polymer swells. During the evaporation of the solvent, the swelling of the polymer matrix does not recede at the same rate as the evaporating of solvent, and microcracks form in the surface as the polymer attempts to maintain its swollen volume. This process is sometimes referred to as "crazing."

In one embodiment, housing 24 is constructed from a polymeric material, such as polycarbonate, and the surface 110 of the inlet portion of the housing 24 is exposed to a solvent, such as N,N,N',N' tetramethylethylenediamine (TEMED), polyethylene glycol, silicone oil or other suitable solvent that penetrates and swells the polymer matrix of the housing. The inlet of the housing can be exposed to the solvent by dipping, spraying, rolling or brushing. The solvent is then be evaporated from the housing to form microcracks 114. Because of the above mentioned light scattering and reflecting properties, the crazed material with microcracks now appears a whitish or dull color or opaque. When the microcracks surface is exposed to an antiseptic agent, the light scattering and reflection of the crazed surface ceases and the microcracked surface gives a perceptible indication by visually appearing to returns to that of its original color.

One advantageous aspect of using a solvent to form microcracks on a surface of the housing is that no new material is added to the housing, i.e., the composition of the housing is essentially the same before and after the creation of the microcracked structure.

Figure 15B:
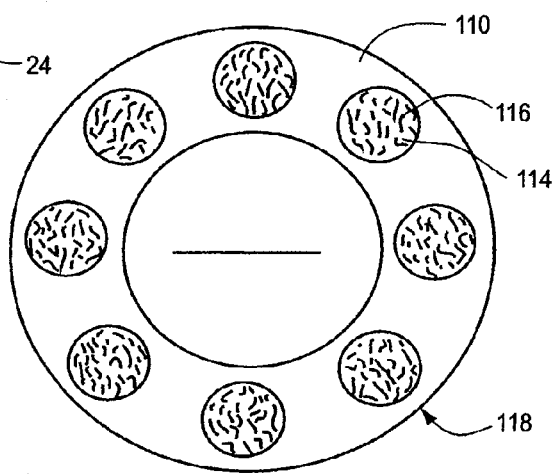
FIG. 15*b* is a plan view of another embodiment of an exposure indicator including a surface having a crazed pattern.

In another embodiment shown in FIG. 15b, the surface 110 of the housing 24 includes individual microcracked portions 116 that create a visible pattern 118. In the illustrated embodiment, the surface 110 includes individual portions 116 of microcracks 114 spaced around the inlet surface 110 of the housing to create a ring-like pattern. However, the pattern 118 can vary depending on the desired application. When the inlet surface 110 is exposed to an antiseptic agent, such as by swabbing with IPA, the antiseptic agent wets and interacts with the microcracked portions 116 of the surface, causing the microcracked portions to appear the same color as the rest of the surface. This creates a visual effect in which the pattern appears to disappear. When the antiseptic agent evaporates from the surface, the microcracked portions 116 of the surface 110 turn back to their whitish color and the pattern reappears.

In one embodiment, the pattern 118 on the surface of the housing 110 is formed by selectively applying the solvent process described above to the different portions of surface 110 of the inlet housing.

Figure 15C:
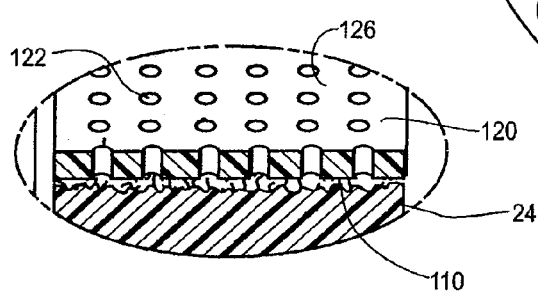
FIG. 15*c* is an enlarged perspective view taken along line A-A of FIG. 13, generally showing another embodiment of an exposure indicator, such as a crazed upper surface of the inlet housing and a permeable layer over the crazed surface.

In another embodiment, as illustrated in FIG. 15c, a permeable layer or cover 120, such as a thin porous polymeric film or a microporous IPA permeable polymer coating, is placed over the inlet surface 110 of the housing 24 to cover the microcracked surface. For example, the permeable cover can be a POREX® polycarbonate membrane (Osmonics, Minnetonka, Minn.) The permeable cover 120 can be attached to the housing 24 by an adhesive such as cyanoacrylate or can be ultrasonically welded to the housing. The cover 120 has a thickness of about 10 μm to 25 μm, pores 122 having a size of between about 0.2 μm to about 1 μm and a porosity or pore density of between about $3 \times 10^8$ pores/cm$^2$ and about $2 \times 10^7$ pores/cm$^2$. In one embodiment, the cover 120 is a polycarbonate thin film having a thickness of about 25 μm thick, a pores size of about 0.2 μm and a porosity of about $3 \times 10^8$ pores/cm$^2$.

When the upper surface 126 of the cover 120 is exposed to the antiseptic agent, such as by swabbing with IPA, the antiseptic agent enters the pores 122 of the cover 120 and is translated to the microcracks 114 on the inlet surface 110 of the housing 24. After the antiseptic agent has wetted the microcracked surface of the housing, the surface changes from its whitish color or opaque color to its original color or to a transparent or translucent appearance, giving a visual indication that antiseptic agent has been applied to the housing. The antiseptic agent then evaporates from the microcracks 114 through the pores 122 of the cover 120, and the microcracked surface returns to its whitish color or opaque appearance.

In a further embodiment, the cover is a microporous alcohol permeable acrylate coating, such as the acrylate resin coatings described herein. The acrylate coating is disposed over the crazed inlet surface 110. Upon swabbing the acrylate coating with IPA, the IPA permeates the coating and is translated to the microcracks. The IPA interacts with the microcracks and the surface changes from its whitish color to its original color, giving a visible indication that the surface has been exposed to an antiseptic agent. After a period of time, the antiseptic agent evaporates from the microcracked surface and the acrylate coating, and the microcracked surface resumes its whitish appearance.

The permeable layer or cover 120 over the microcracked surface serves various purposes, such as to provide a protective layer over the surface, control absorption and evaporation of antiseptic agent and/or provide a layer of selective permeability. The cover may encourage a more effective antiseptic swab technique by a clinician because the clinician may be required to swab the cover with greater deliberate and consistent pressure so that the antiseptic agent permeates the film and wets the microcracked surface thereunder.

Figure 15D:
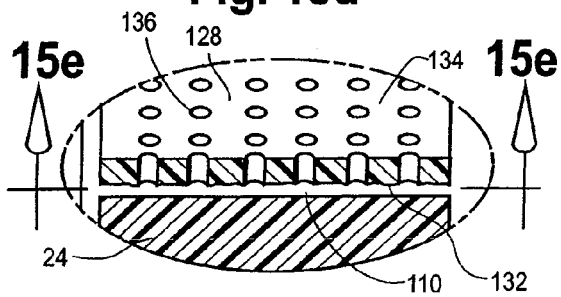
FIG. 15*d* is an enlarged perspective view taken along line A-A of FIG. 13, generally showing another embodiment of an exposure indicator, such as a permeable layer having a crazed bottom surface.
Figure 15F:
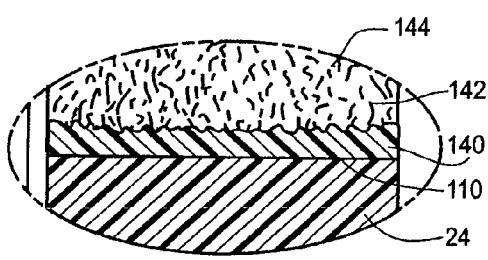
FIG. 15*f* is an enlarged perspective view taken along line A-A of FIG. 13, generally showing another embodiment of an exposure indicator such as a layer of material having a crazed surface disposed on the upper surface of the inlet housing.
Figure 15E:
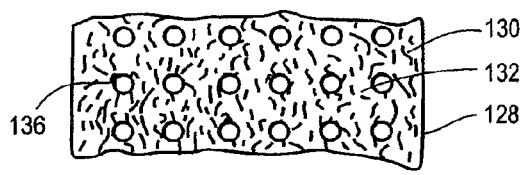
FIG. 15*e* is a plan view of the bottom surface of the permeable layer of FIG. 15*d*.

In a further embodiment, referring to FIG. 15d-15e, a transparent thin porous film 128, such as the one described above, includes microcracks 130 in a surface 132 of the film. The microcracks 130 are made in the surface 132 of the film by a similar process described above or any other suitable process. The microcracks 130 give the originally transparent film 128 a whitish or substantially opaque appearance. The thin film 128 is then attached to the housing 24, such as by an adhesive or ultrasonic welding, with the surface 132 of the film containing the microcracks 130 against the inlet surface 110 of the housing. Once attached to the housing, the film 128 in its whitish or opaque state obscures or hides the color of the housing surface 110.

When the upper surface 134 of the film 128 is exposed to an antiseptic agent, the antiseptic agent enters the pores 136 of the film and is translated to the microcracked surface 132 of the film via capillary action. When the microcracks 130 are wetted by the antiseptic agent, the whitish surface turns transparent and the color of surface 110 of the housing 24 becomes visible to indicate that the access device has been treated with an antiseptic agent. Sometime after treatment, the antiseptic agent evaporates through the pores 136 of the thin film 128 and the whitish color of the thin film returns and obscures the color of the housing.

In another embodiment, referring to FIG. 15f, an antiseptic indicator 138 includes a layer 140 of material that is disposed on the inlet surface 110 of the housing 24 and has a microcracked surface 142. In one embodiment, the layer of material 140 is a polymer coating, such as a UV curable resin that is applied to the housing and allowed to cure. The polymer coating can also be the same material as the housing. For example, if the housing is created from a polycarbonate material, the polymer coating can include polycarbonate. Additionally, the polymer coating can include other materials such as polystyrene, ABS or acrylic. After the coating is cured, the upper surface 142 of the coating is treated with a solvent to form microcracks 144 in a manner similar to that described above. Similar to the other microcracked surfaces described above, when the surface is dry, it has an opaque or whitish appearance and when the surface is wetted with an antiseptic agent, the surface becomes transparent or appears to be its original color.

Crazing the layer 140 instead of the housing allows for more control over the resultant microcracked surface. For instance, the material of the polymer coating can be specifically selected for the microcracks that can be formed upon treatment with a particular solvent.

Micropatterned Antiseptic Indication

In another embodiment, the antiseptic indicator includes a surface including a micropatterned portion that undergoes a surface light reflection change to indicate that the surface has been exposed to an antiseptic agent. For example, the surface includes micropatterned portion that has a diffraction grating which absorbs certain wavelengths or colors of light and reflects others. This reflection of the wavelengths or colors of light results in the micropattern appearing to be a shiny color or colors similar to the reflective security hologram on a credit card. In one embodiment, the diffraction grating of the micropatterned surface is created by a plurality of ridges and grooves. The groove width or groove density of the micropattern (i.e., the spacing between the grooves) determines the colors of light that are reflected by the micropattern. In one embodiment, the micropatterned surface has a groove width of about 0.1 μm to about 0.7 μm and in another embodiment, the micropattern has a groove width of about 0.5 μm. Because the color of the reflected light is directly related to the groove width or spacing, the observable color of the micropattern can be changed by varying the width of the groove. For example, in one embodiment, the groove width of the micropattern causes the surface to display a shiny rainbow-like appearance. Alternatively, in another embodiment, the groove width of the micropattern causes the surface to display a particular color or set of colors, such as green or red.

Furthermore, the micropattern can vary from extremely complex to very simple. In its simplest form, the micropattern includes a plurality of parallel ridges and grooves that are configured to display a certain color. In more complex constructions, the micropattern could be a complex pattern of ridges and grooves that displays images, such as a symbol or written messages, and a variety of colors of light. In one embodiment, the complex pattern includes groups of grooves and ridges of varying groove width and extending in various directions with respect to one another.

When the micropatterned surface is exposed to an antiseptic agent, such as by swabbing with IPA, the antiseptic agent interacts with the micropatterned surface by filling the grooves of the micropattern and creating a more normal reflective surface. The interaction between the antiseptic agent and the micropattern causes the micropattern surface to perceptibly change in appearance. Upon evaporation of the antiseptic agent, the micropatterned surface again reflects only certain colors of light and changes back to its original appearance.

Figure 16A:
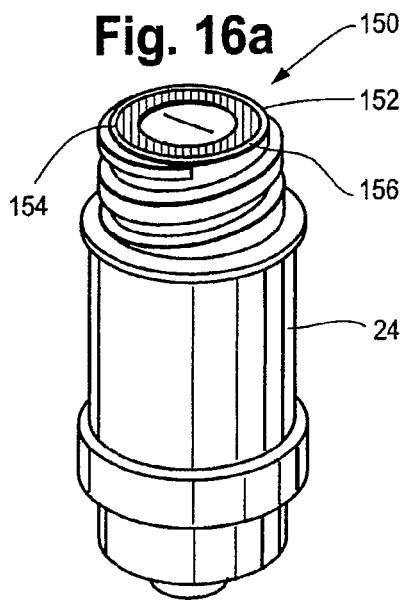
FIG. 16*a* is a perspective view of a fluid access device having one embodiment of an exposure indicator disposed on the upper surface of the inlet housing.
Figure 16B:
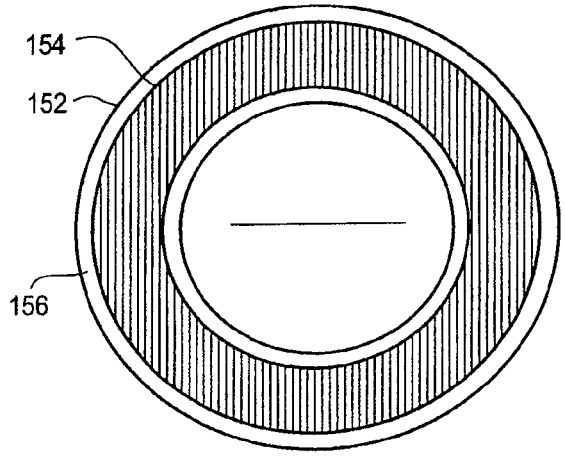
FIG. 16*b* is a plan view of the upper surface of the inlet housing of FIG. 16*a*.

For example, in FIGS. 16a and 16b, the fluid access device housing 24 includes an antiseptic indicator 150 that has a surface 152 including a micropatterned portion 154. The micropatterned portion has a diffraction grating that reflects only a certain color or set of colors of light. The diffraction grating causes the micropatterned portion to visually appear to be the color of the light that is reflected. Such reflection of light makes the micropatterned portion appear visually distinguishable from the surrounding non-patterned or smooth portions 156 of surface 152. When surface 152 is exposed to an antiseptic agent, the antiseptic agent interacts with the micropatterned portion 154, e.g., the antiseptic agent fills in the grooves of the micropattern. The interaction between the antiseptic agent and the micropattern causes the micropattern to have a more normal reflection of light, changing the appearance of the micropatterned portion. The change of appearance indicates that the surface has been exposed to an antiseptic agent. In one embodiment, the micropatterned portion 154 appears visually indistinguishable from the surrounding non-patterned or smooth portions 154 of the surface 152.

In one embodiment, the antiseptic indicator 150 includes a polymer membrane, such as membranes made from curable acrylate resins or thermoplastic polymers. The polymer membrane can be made of a porous or nonporous material. Additionally, the material of the membrane can be an IPA absorbing material. The membrane can be coated onto the housing 24 or can be attached to the housing by any suitable attachment method, such as adhesive bonding or ultrasonic welding.

Figure 16C:
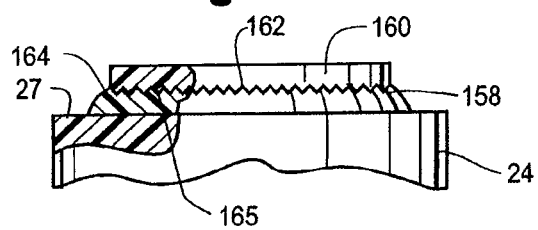
FIG. 16*c* is an elevational view showing the inlet portion of the housing during the formation of an exposure indicator.

For example, FIG. 16c depicts one embodiment of a fluid access device including a micropatterned antiseptic indicator. In this embodiment, a layer of non-cured polymer resin 158, such as a radiation curable resin, a thermally curable resin or a dual curable resin, for example a UV curable acrylate-based resin, is coated on the surface 27 of the inlet portion of the housing 24. A stamp or relief pattern 160 having the desired micropattern 162 is then placed atop the top surface 164 of the resin 158 to emboss or create a micropattern 165 into the layer of resin 158. The resin is then cured. When the resin is a UV curable resin, stamp 160 can be a polytetrafluoroethylene or nylon membrane or other type of membrane or microporous or woven layered film or fabric that is semi-transparent to UV light. After the layer of resin 158 is cured, the stamp 160 is removed from the resin layer, leaving an embossed, matted micropatterned surface 164 that has a diffraction grating which reflects only particular wavelengths of light.

In an alternative embodiment, the polymer membrane located on the housing can be a thermoplastic polymer, such as polycarbonate. In this embodiment, the thermoplastic polymer membrane is heated to soften the polymer material. The stamp is then placed in contact with a surface of the thermoplastic polymer membrane to emboss the micropattern into the membrane. The membrane is cooled, resulting in a thermoplastic polymer membrane having a micropatterned surface.

In a further embodiment, when the housing of the fluid access device is made of a thermoplastic polymer material, a surface of the housing is heated to soften the surface. The stamp is then placed into contact with the softened surface of the housing to emboss the micropattern into the surface of the housing. The surface is then allowed to cool, resulting in a fluid access device having a micropatterned antiseptic indicator embossed in the surface of the housing.

Figure 16D:
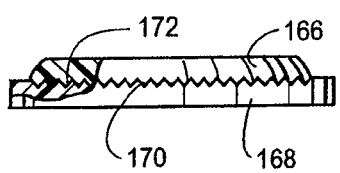
FIG. 16*d* is an elevational view showing one embodiment of a stamp that can be used to form an exposure indicator.

Referring to FIG. 16d, another method of forming a medical access device having a micropatterned indicator is depicted. A polymer resin 166, such as a radiation curable resin, a thermally curable resin or a dual curable resin, for example a UV curable acrylate-based resin, is deposited onto a stamp or a relief pattern 168 having a desired micropattern 170. In one embodiment, the stamp is a 0.5 µm grating mask (0.5 µm clear×0.5 µm dark) electron-beam etched on 2.0 µm chromium-sputtered optically flat quartz silica surface having the desired pattern. Resin 166 is then cured to form a thin film having a micropattern on the surface 172 of film. Cured resin 166 is then lifted off the stamp 168 and attached to the inlet end of the housing by a suitable method, such as by using an adhesive or by ultrasonic welding.

In another embodiment, the polymer coating and the micropattern thereon are configured so that the micropatterned area changes color(s) upon exposure to an antiseptic agent. For example, in one embodiment, the polymer coating includes a micropatterned surface that displays a first color or set of colors. The polymer coating also is a coating that absorbs IPA and swells upon absorption of the IPA. When IPA is applied to the surface of the polymer coating, the polymer absorbs the IPA and swells. As the polymer swells, the groove width of the micropattern changes. This change in groove width causes the micropatterned surface to display a second different color or set of colors. Upon evaporation of the IPA, the polymer shrinks and the groove width of the micropattern returns to its original state to substantially display its original color.

Figure 16E:
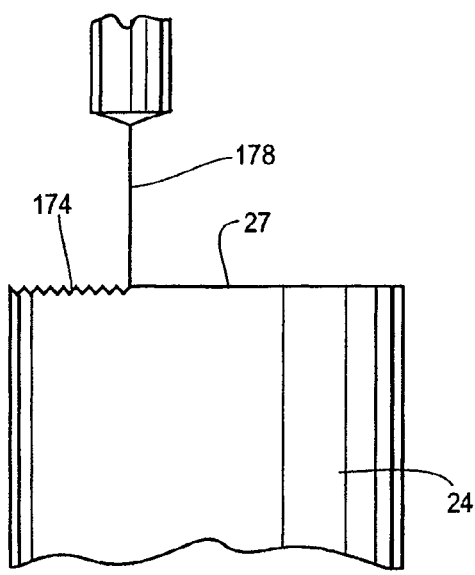
FIG. 16*e* is a schematic illustration showing one embodiment for forming an exposure indicator on the fluid access device.
Figure 16F:
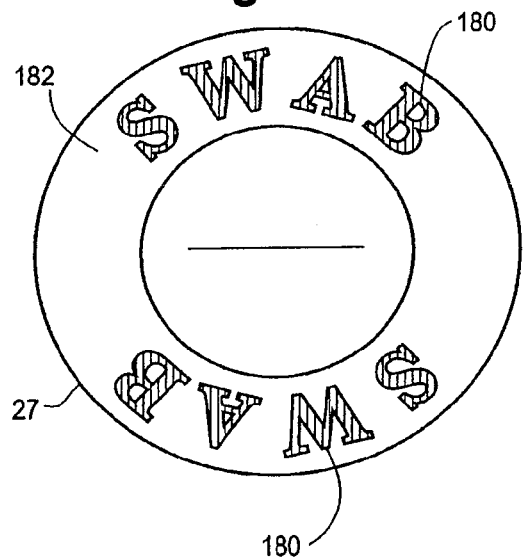
FIG. 16*f* is a plan view of one embodiment of an exposure indicator.

In a further embodiment, the micropattern is located in the surface of the fluid access device housing, instead of on a material disposed on the housing surface. Referring to FIG. 16e, in another method of creating a micropattern 174 on the surface 27 of the housing 24, a laser beam 178 is passed over the surface of the housing to ablate the surface and form the micropattern 174. The groove density of the micropattern can be between about 0.1 µm to about 0.7 µm. Furthermore, as illustrated in FIG. 16f, the laser beam 178 can be used to make customize and complex patterns to produce images 180, such as words or logos, on the surface of the inlet housing. In one embodiment, when the surface is exposed to an antiseptic agent, the agent interacts with the micropattern 180 so that the micropatterned surface is visually indistinguishable from the non-patterned surface 182, thereby appearing as if the pattern has disappeared. The disappearance of the pattern indicates that proper disinfecting has occurred.

Luminescent Antiseptic Indicator

In certain situations, medical personal are required to perform medical procedures in dark or lowlight environments. In these lowlight situations, it can be difficult for the medical personal to observe the antiseptic indicator and any visual indication associated therewith. In order to assist medical personal in observing the antiseptic indicator in a lowlight environment, the antiseptic indicator can include a luminescent characteristic, e.g., glows in the dark or under conditions of very low light.

Figure 17A:
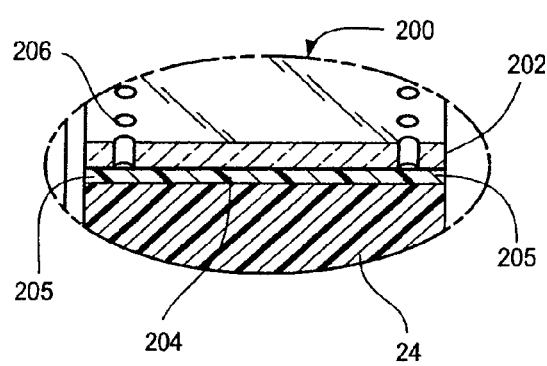
FIGS. 17*a* and 17*b* are enlarged perspective views taken along line A-A of FIG. 13, showing one embodiment of an exposure indicator having a transparency changing layer and a luminescent layer.

Referring to FIG. 17a, an antiseptic indicator 200 is disposed on the housing 24 of a fluid access device. The antiseptic indicator 200 includes a transparency changing layer 202, such as the microporous membranes or microporous particles described herein or other suitable transparency-changing layer, and a luminescent layer 204 that includes a luminescent material, such as a photoluminescent or chemiluminescent compound or mixture of compounds.

Figure 17B:
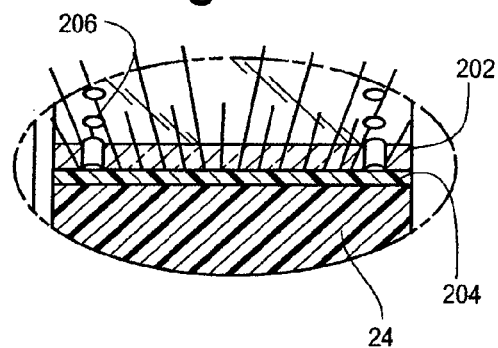

In a substantially non-transparent or opaque state, the transparency-changing layer 202 serves to substantially obscure the light emitted from the luminescent layer 204, so that such light cannot be observed. Referring to FIG. 17b, when the transparency-changing layer 202 is exposed to an antiseptic agent, such as swabbing with an IPA wipe, the transparency-changing layer 202 changes into a substantially transparent state so that the light emitted from the luminescent layer 204 is visible to the user. The visible light indicates to the use that the fluid access device has been exposed to an antiseptic agent.

Furthermore, most photoluminescent materials typically require exposure to light energy before use. In one embodiment, the sides 205 of the of the photoluminescent layer of material 204 are uncovered so that the sides are exposed to light and the photoluminescent material can absorb light energy through the sides. Alternatively or in conjunction with the uncovered sides 205, the transparency changing layer 202 can include one or more openings 206 therethrough to allow the photoluminescent materials to be exposed to light. In a further embodiment, the housing is a clear or transparent housing that allows the photoluminescent layer to be exposed to light.

A variety of photoluminescent chemicals can be employed in the antiseptic indicator to produce various colors of light. For example, the photoluminescent compounds may contain camphor, dibutyl phthalate, ethyl acetate, IPA, n-butyl acetate, nitrocellulose or acrylic based solution or powder, in combination with $Al_2O_3$, $SrCO_2$, $Eu_2O_3$, $Dy_2O_3$, $Tio_2$, $SiO_2$, CaO or $SrAl_2O_4$. Additionally, the luminescence of the antiseptic indicator can be created with the use of luminescent particles, such as quantum dots that contain CdSe, ZnS or CdSe.

The photoluminescent chemicals and luminescent particles can be attached to the device by a variety of different techniques and processes. For example, in one embodiment, the luminescent layer is an adhesive layer that has photoluminescent compounds blended therewith. The adhesive/photoluminescent mixture attaches the transparency layer to the housing and emits the indicating light. Alternatively, the photoluminescent compound is deposited on a surface of the device or a surface of the transparency changing layer by, for example, solution casting, immobilization processes, adhesive bonding, dispersion or by other suitable depositing processes. Additionally, in one embodiment, the photoluminescent chemical or the luminescent particles are added to the base resin of a polymer that forms the housing or the valve member.

Figure 17C:
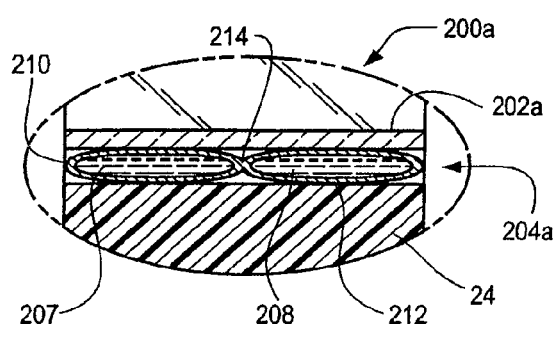
FIGS. 17*c* and 17*d* are enlarged perspective views taken along line A-A of FIG. 13, showing another embodiment of an exposure indicator having a transparency changing layer and a luminescent layer.

In another embodiment, the luminescent layer 204 includes a layer of chemiluminescent solutions that react with each other to emit the indicating light. Referring to FIG. 17c, the antiseptic indicator 200a includes a transparency-changing layer 202a, such as a microporous membrane or a layer of microporous particles or other suitable transparency changing layer. Under the transparency-changing layer 202a is a luminescent layer 204a that includes a first solution 207 and a second solution 208, which when mixed, emit light. For example, in one embodiment, the first solution 207 is a solution of hydrogen peroxide and a fluorescent dye, such as 1,6,7,12-tetra-phenoxy-N—N'-bis(2,6-diisopropylphenyl)-3,4,9,10-perylene dicarboximide, and the second solution 208 is an oxalate such as bis(2,4,5-trichloro-6-carbopentoxy-lphenyl)oxalate. Such compounds and chemical reactions are generally described in U.S. Pat. No. 5,122,306, which is incorporated herein by reference.

Figure 17D:
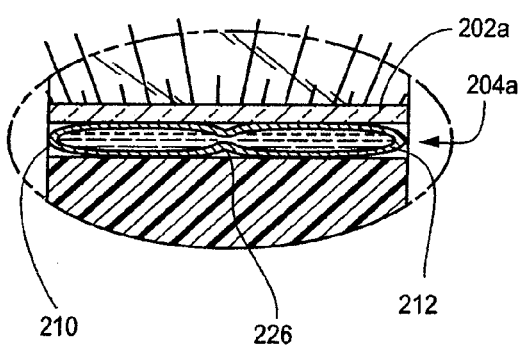

The first solution 207 and the second solution 208 are each contained within separate containers 210, 212. A breakable seal 214, such as frangible seal, is located between the containers 210, 210. The seal 214 should have sufficient strength to resist breaking prior to use, but should also be sufficiently weak so as to be broken upon pressure caused by swabbing. As shown in FIG. 17d, when the seal 214 is broken, the solutions 207, 208 mix to form a solution 216 that emits light. Upon swabbing, the transparency changing layer 202a changes from opaque to transparent. Additionally, the pressure from swabbing causes the seal 214 between the solutions to break. When the solutions 207, 208 mix, the luminescent layer 204a emits light. The emitted light is observed through the transparency-changing layer 202a, thereby indicating that the fluid access device has been exposed to an antiseptic agent. After the antiseptic agent evaporates, the transparency layer returns to its non-transparent state and obscures the emitted light.

In another embodiment, the fluid access device housing itself is made of a polymer material that includes a photoluminescent additive which causes the housing to emitted light or glow in the dark. Such light emitting polymer materials are commercially available through RTP, Co., Winona, Minn. In this embodiment, a substantially opaque transparency changing layer, such as the microporous membranes or microporous particles described herein or any other suitable transparency changing layer, is attached to the top surface of the housing made of a resin material including a photoluminescent additive. Prior to exposure to an antiseptic agent, the substantially opaque transparency changing layer obscures the light emitted from the top surface of the housing. When the transparency changing layer is exposed to an antiseptic agent, the transparency changing layer becomes transparent and light emitted from the top surface of the housing is visible to the user. The visible light emitted from the top surface of the housing indicates that the housing has been exposed to an antiseptic agent. After a period of time, the antiseptic agent evaporates and the transparency changing layer returns to its opaque state, once again obscuring the light emitted form the top surface of the housing.

Antiseptic Indicator Including a Microporous Membrane with a Particle Morphology and Method of Making the Same As described above with respect to FIG. 14e, microporous membranes that appear white or opaque when dry and transparent when wetted by an antiseptic agent can be used as antiseptic indicators. When such membranes are used as antiseptic indicators, it is preferable for the function and structure of the membranes to be such that membranes are sufficiently wetted with antiseptic agent during the accepted medical disinfecting procedure. Furthermore, because the medical devices will most likely be exposed to blood, it is also preferable for the microporous membrane to be resistant to blood staining.

The present disclosure encompasses a process for manufacturing membranes that have a morphology including a particle-like structure. The membrane has good wetability in regard to antiseptic agents, such as IPA or 70% IPA, and is substantially resistant to blood staining.

The process generally involves the steps of:

(1) Mixing a polymer with a solvent that requires heat to dissolve the polymer and then heating the polymer/solvent mixture to form a homogenous solution. Optionally, a pore former, such as a glycerol, can be added during this step.

(2) The solution is cast on a flat surface, for example, a glass plate.

(3) The cast is then submerged into a coagulation bath of a liquid that does not dissolve or slightly dissolves the polymer. For example, the coagulation bath can be a cold bath of water, methanol, a methanol/water mixture or a water/acetone mixture or any other suitable liquid or mixture of liquids that only slightly dissolve or do not dissolve the polymer. The methanol/water mixture can be 90% methanol and 10% water, and the water/acetone mixture can be 90% water and 10% acetone or less. Submerging the cast into the coagulation bath induces a liquid/liquid phase separation which forms a colloidal phase of a polymer rich phase and a polymer poor phase.

(4) After the emulsion has undergone gelation, the coagulation bath non-solvent and water are evaporated to form the porous membrane.

In one embodiment, a polymer is mixed with a solvent that requires heating to dissolve the polymer. The polymer can be, for example, polyvinylidene fluoride (PVDF), polycarbonate (PC), polyethylene, polypropylene, nylon, or polyacrylonitrile. Additionally the polymer can be between about 1% to about 30% by weight of the mixture and the solvent can be between about 70% to about 99% by weight of the mixture. The solvents can include for example, triethylphosphate (TEP), acetone, toluene, methylene chloride, cyclohexanone, DMSO, DMF, DMAc, NMP, choloroform, xylene, dioxane or any other suitable solvent that requires heat to dissolve the polymer. Additionally, if desired, a pore former, such as glycerol, salt or alcohol, could also be added at this time. The pore former can be about 2% to 10% by weight of the mixture or can be at about a 1:2 to about 1:5 ratio to the polymer.

The polymer/solvent mixture is then heated to a temperature that is sufficient for the solvent to dissolve the polymer and form a homogeneous solution. The solution is cast on a flat surface, such as a glass plate, and submerged into coagulation bath that has a temperature that is lower than the temperature of the solution. In one embodiment, the coagulation bath has a temperature of about 0° C. to about 22° C. As the solution cools and mixes with the coagulation bath, a liquid/liquid phase separation is induced. The phase separation is between a polymer rich phase (solvent and polymer) and a polymer poor phase (water and polymer). Shortly after the phase separation takes place, the polymer molecules began to nucleate and a colloidal phase is formed including the polymer-rich phase and the polymer-poor phase. As the polymer molecules nucleate, they form micelle-like or particle-like structures. After gelation occurs, the solvent and the liquids of the coagulation bath are evaporated off, for instance by air drying, and a microporous membrane having a morphology including a particle-like structure is form.

The number and size of the particle-like structures that are formed and the size of the pores that are formed can vary depending on the molecular weight and the molecular weight distribution of the polymer used, the temperature to which the solution is cooled to induce phase separation and the time it takes for the solution to cool and phase separate. In one embodiment, the particle-like structures have a size from about 0.5 μm to about 20 μm, and the pores size is about 0.005 μm to about 2 μm.

EXAMPLES

The following examples are given to show microporous materials that have been made in accordance with the present disclosure. However, it will be understood that the following examples are exemplary only, and are not intended to be comprehensive of the many different microporous materials which may be made in accordance with the present disclosure.

Example 1

In example 1, PVDF powder or KYNAR® (commercially available through Arkema, Inc. Philadelphia, Pa., USA) was mixed with 98% pure TEP at a ratio of 20% PVDF powder to 80% TEP, which formed a whitish mixture. The mixture was then heated to a temperature of 68° C. to form a homogenous solution. After the color of the solution changed from off-white to transparent, the solution was cast on a glass plate and submerged into a bath of water having a temperature of about 22° C. to induce a liquid/liquid phase separation. The mixture was maintained in the 22° C. bath during coagulation. After coagulation, the membrane that was formed was soaked in a water bath for 10 minutes and then dried a room temperature to evaporate off the water and TEP. The result was a microporous PVDF membrane that was substantially opaque in appearance and had a morphology including particle-like structures. The membrane was resistant to blood staining and could be sufficiently wetted by IPA to change the transparency of the membrane.

Example 2

In example 2, the same above process of Example 1 was applied, except that the cast was submerged into a bath of water having a temperature of about 8° C. The result was a microporous PVDF membrane that was substantially opaque in appearance and had a morphology including particle-like structures. The membrane was resistant to blood staining and could be sufficiently wetted by IPA to change the transparency of the membrane.

Example 3

In example 3, the same above process of Example 1 was applied, except that the PVDF/TEP mixture was heated to 54° C. and the cast was submerged into a bath of water having a temperature of about 12° C. The result was a microporous PVDF membrane that was substantially opaque in appearance and had a morphology including particle-like structures. The membrane was resistant to blood staining and could be sufficiently wetted by TA to change the transparency of the membrane.

Example 4

In example 4, the same above process of Example 1 was applied, except that the PVDF/TEP mixture was heated to 54° C. and the cast was submerged into a bath of water having a temperature of about 15° C. The result was a microporous PVDF membrane that was substantially opaque in appearance and had a morphology including particle-like structures. The membrane was resistant to blood staining and could be sufficiently wetted by IPA to change the transparency of the membrane.

Figure 18:
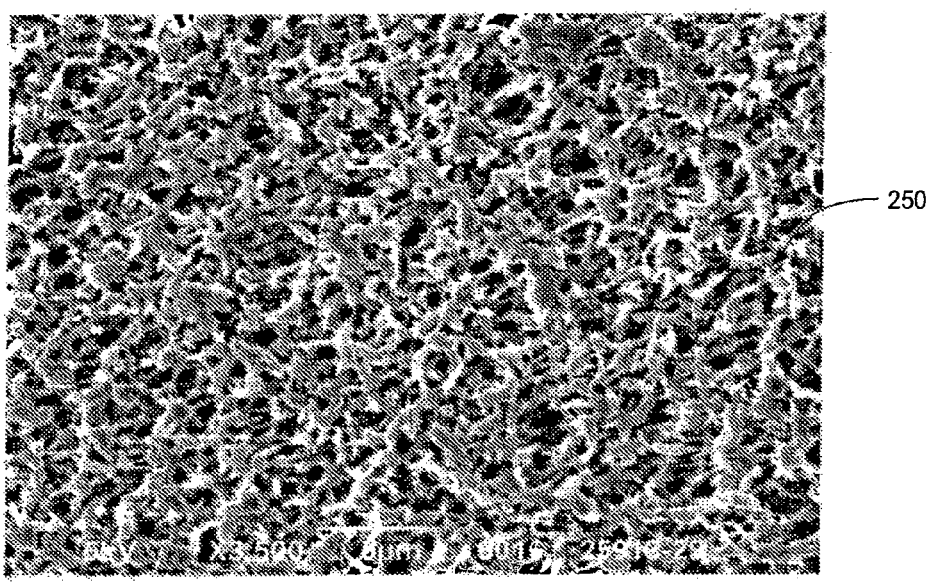
FIG. 18 is a scanning electron micrograph of the surface of a commercially available microporous PVDF polymer membrane.
Figure 19:
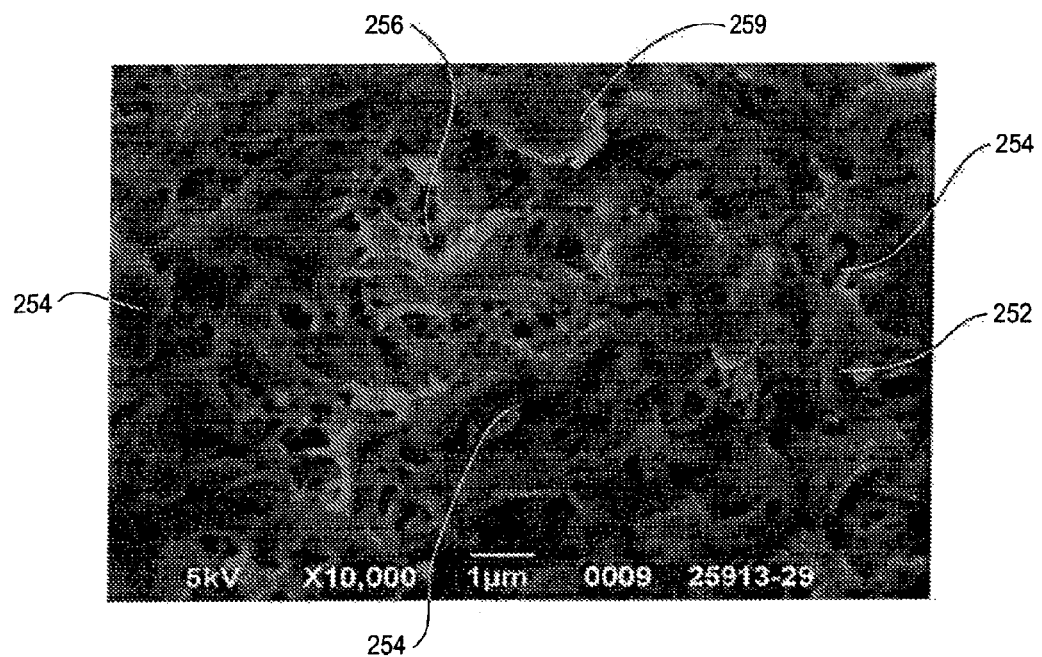
FIG. 19 is a scanning electron micrograph of a microporous PVDF polymer membrane made by a process of the present disclosure.

FIGS. 18 and 19 illustrate a side-by-side comparison of the morphology of a commercially available medical grade PVDF microporous membrane and a microporous membrane made by the above described process. FIG. 18 is a scanning electron micrograph of the surface 250 of a commercially available medical grade PVDF sold under the name Millipore V-180 (commercially available through Millipore Corporation, Bedford, Mass., USA). As can be seen, the morphology of the membrane is a sponge-like matrix. When the membrane is exposed to blood, this sponge-like matrix absorbs the blood into the matrix, which causes undesired blood staining.

Referring now to FIG. 19, there is shown a scanning electron micrograph of the surface 252 of a membrane that has been made by the process outlined in Example 3 above. As can be seen, the morphology of the membrane is very different from that of the commercially available membrane shown in FIG. 18. For example, instead of a uniform sponge-like surface, the membrane has a denser irregularly shaped surface 252 with particle-like structures 254. These particle-like structures 254 partly cover or close off the pores 256 in the surface. Without being bound to any particular theory, it is believed the particle-like structures partially cover the pores in such a fashion as to block blood from entering the pores, while allowing IPA to enter the pores. Thus, it is believed that the particle-like structures provide assistance in resisting staining caused by contact with blood.

Alteration of OEM Membrane

In another embodiment of the present disclosure, the morphology, i.e., the physical characteristic of the porous structure and the surface structure, of the polymer membrane, such as an OEM (original equipment manufactures) PVDF membrane, is optimized to include the desired characteristics of an antiseptic indicator, e.g., resistance to blood staining and the desired wettability. Such an optimization processes to achieve resistance to blood staining and/or the desired wettability include thermal and thermal compress processes, annealing, solvent treatments and stretching, etching, swelling or shrinking processes.

For example, in one embodiment, the morphology of the surface of a membrane is changed by applying a thermal or a thermal compress process. The process includes heating the surface of one or both sides of the membrane, with or without compression, and then allowing the surface to cool. While heating, the surface of the membrane melts, creating heterogeneous nuclei. Upon cooling, the heterogeneous nuclei reform on the surface, changing the morphology of the membrane and resulting in dense particle-like formations on the surface. Similar to those discussed above in the pervious section, the surfaces containing particle-like structures have an increased blood stain resistance.

In another method, the morphology or crystallite size of the polymer is changed by annealing the membrane. In the annealing process, the temperature of the polymer membrane is increased to near the melting point of the polymer. At the annealing temperature, the polymer reforms into a denser structure that has an increased resistance to blood staining.

In other methods, the morphology of the membrane is optimized by treating the membrane with solvent or stretching, etching, swelling or shrinking the membrane or by any combination of these processes. These processes can be applied to both sides of the membrane in order to alter the pore size, pore opening or pore structure, to make the surface more or less dense, or to form particle-like formations on the surface. For example, in one embodiment, a solvent is applied to the surface of a polymer membrane to dissolve the surface. As the solvent evaporates, the surface polymer chains rearrange, changing the structure of the membrane surface.

Method of Forming a Microporous Indicator on a Surface of a Medical Device

In another embodiment, a microporous indicator that appears whitish or opaque prior to exposure to an antiseptic agent and appears to be colored or transparent after exposure to an antiseptic agent can be formed on the surface of a medical device by a spinodal-induced phase separation process.

In general, the method includes dipping a medical device made of a polymer material into a solvent that dissolves the polymer. The solvent can be a solvent which readily dissolves the polymer or a solvent that requires heat to dissolve the polymer. The medical device is maintained in the solvent for a time period sufficient to form a homogenous solution, but not long enough to cause the medical device to become fluid or lose its shape. The medical device is then removed from the solvent and a phase separation is induced. The phase separation includes a polymer poor-phase and a polymer-rich phase. After the phase separation has occurred, the polymer begins to form a matrix that has particle-like structures interlaced within the matrix and on the surface of the polymer.

The particle-like structures on the surface of the polymer scatter and reflect light so that the surface appears a whitish matte color. When the surface is exposed to an antiseptic agent, such as IPA, the scattering and reflection of light ceases and the surface appears to be the color of the surface material.

In one embodiment, the method includes dipping a medical device made of a polymer material into a solvent that requires heat to dissolve the polymer. The solvent can be heated to the required temperature before or after the medical device has been dipped into the solvent. The medical device is maintained in the heated solvent for a time period that is sufficient to form a homogenous solution, but not long enough to cause the medical device to lose its shape. The medical device is then removed from the solvent and allowed to cool. In one embodiment, the medical device and the solvent are cool in a cold air stream at a rate of 20° C. per minute.

As the medical device and the solvent cool, a phase separation is induced. The phase separation includes a polymer-rich phase and a polymer-poor phase. As the medical device further cools, it forms a polymer matrix having particle like structures interlaced and on the surface of the polymer. After the polymer matrix is formed, the solvent can be removed from the polymer by evaporation or by dipping into a second solvent that extracts the first solvent. The size of the particle-like structures can depend on various different factors, such as the type of polymer material, the type of solvent and the rate of cooling and allowed to cool.

In another embodiment, the upper surface of a polycarbonate access device housing is dipped into a bath of solvent that may or may not require heat to dissolve the polycarbonate material. Such solvents can include 1,2 dioxane, xylene, a mixture of 75% 1,2 dioxane and 25% xylene, chloroform or a dioxane/chloroform mixture. The housing is maintained in the bath for a time period that is sufficient to form a homogenous solution, but is not long enough to cause the material of the housing to become fluid or lose its shape. After the homogenous solution is formed, the polycarbonate housing is removed from the bath. If the solvent has been heated, the housing and solvent are cooled. After the housing has been removed from the bath, a phase separation is induced between a polymer rich phase and a polymer poor phase. After the phase separation, the polymer forms a polymer matrix that has particle-like structures interlaced within the matrix and on the surface of the polymer.

As explained above, the particle-like structures cause light to scatter and the surface appears a whitish matte color. When the surface is exposed to an antiseptic agent, the scattering ceases and the surface appears to be the substantially original color of the polycarbonate material.

Methods of Attaching an Antiseptic Indicator

The above described microporous membranes, microporous particles and dyes that constitute the make-up of the above described antiseptic indicators can be attached to a surface of a fluid access device using a variety of different methods and techniques. The attachment methods and indicator formation techniques can employ adhesives, laser welding, radiant energy, and chemical reactions and bonds, or any combination of these. The following description includes examples of some of the processes and techniques that can be used to attach the antiseptic indicator and its component parts to a fluid access device. This description it is not meant to be limiting in regard to the any of the antiseptic indicators described herein.

Laser Welding and Cutting

Figure 20A:
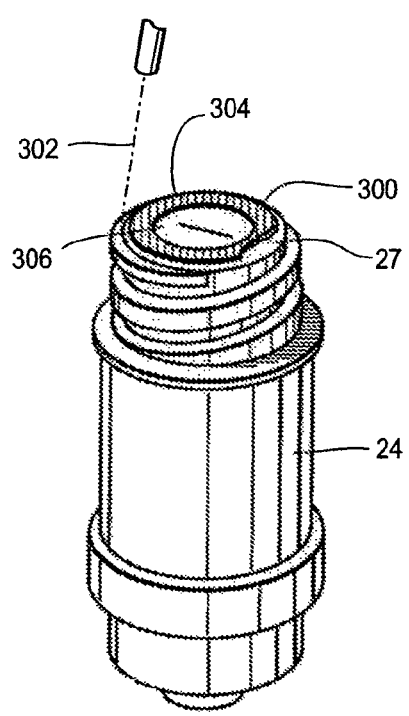
FIG. 20*a* is a schematic illustration of one embodiment of a method of attaching an exposure indicator to a fluid access device.

In one embodiment, when the antiseptic indicator includes a membrane, such as any of the antiseptic indicating membranes described herein or other suitable membrane, the membrane is attached to the housing by laser welding. For example, referring to FIG. 20a, an antiseptic indicating membrane 300, which includes a layer of hot melt adhesive, such as EVA, is bound to the housing 24 using a laser beam 302. Laser beam 302 activates the EVA to attach the membrane to the housing. Laser beam 302 also welds the inner and outer edges 304, 306 of the membrane 300 to the upper surface 27 of the housing 24. For instance, when the housing 24 is comprised of a material such as polycarbonate, acrylic (such as PMMA), acrylonitrile butadiene styrene (ABS), methyl acrylonitrile butadiene styrene (MABS), polypropylene (PP), cyclic olefin copolymer (COC), polyurethane (PU), polyvinyl chloride (PVC) or other suitable material that has a high melt affinity to laser energy, the laser beam 302 is used to heat or activate the EVA and to melt the surface 27 of the housing 24. The activation of the EVA and the melting of the surface 27 bond the membrane material 300 to housing.

When a laser beam is used to weld the edges of the membrane to the housing, a tight seal is created between the edges of the membrane and the EVA near the housing. The seal between the membrane edges and the EVA advantageously prevents wicking of liquids from the side of the membrane. Furthermore, laser welding the edges of the membrane and EVA creates a smooth, particulate free edge.

In an alternative embodiment, the membrane can be pre-attached to the housing prior to the laser welding. For example, a membrane having an EVA backing is placed against the surface of the housing. A heat compression process is applied to the membrane and housing to activate the EVA and attach the membrane to the housing. The heat compression process can include contacting a hot plate of metal or other heat conducting material to the membrane to transfer heat to the EVA and to press the membrane against the housing. After the membrane has been attached, the laser an cutting welding process described above and below can be employed to seal the edges of the membrane to the surface of the housing.

In another embodiment, the microporous polymer membrane material is provided in a sheet that has an EVA backing. The sheet is attached to a plurality of fluid access device housings by placing the EVA backing in contact with the housings and activating the EVA, such as by employing a heat compression process. The laser beam 302 is then used to simultaneously cut the membrane material to the desired size and weld the membrane to the housing during the same procedure.

For example, a sheet of microporous polymer membrane material can be coated with a hot melt adhesive by an extrusion and calendering process. In one embodiment, EVA is extruded from a hot melt adhesive extruder and coated onto a sheet of microporous PE membrane. The sheet of microporous membrane can have a thickness between about 1 mil (12 µm) and about 12 mil (0.3 mm). Such sheets of microporous polymer material are commercially available through DSM Solutech, The Netherlands. Furthermore, the adhesive backing can have a thickness of between about 1 mil (12 µm) and about 15 mil (0.38 mm). In one embodiment, the sheet of microporous membrane has a thickness of about 25 µm and the adhesive backing has a thickness of about 0.13 mm.

In the process, extruded EVA is delivered as a heated or molten extrudate to a two-roll calendar between a first and second drum, which can be heated drums. Additionally, the sheet of microporous PE membrane is fed to the two roll calendar between the first and second drum. The first and second drums compress the EVA and the sheet of microporous PE material together to form a sheet of microporous PE membrane material having an EVA backing.

A plurality of fluid access device housings are then assembled, for example in an apparatus that orients and holds multiple housings in a desired arrangement. The microporous membrane sheet is then placed in contact with the upper surfaces of the fluid access device so that the EVA backing is placed against the upper surface. Heat compression is applied to activate the EVA and to press the sheet of microporous PE membrane sheet against the housing. For example, a heated metal plate can be pressed against the sheet of material. Optionally, a sheet of release material, such as PTFE, can be placed between the hot plate and the membrane. In one embodiment, the heat compression process is operated at a temperature range between about 100° C. and about 130° C., and a compression time was between about 20 seconds to about 1.5 minutes at a constant compression distance of about 5 mil to about 15 mil. After the heat compression process is completed, the fluid access device housings are firmly attached to the microporous PE material.

Figure 20B:
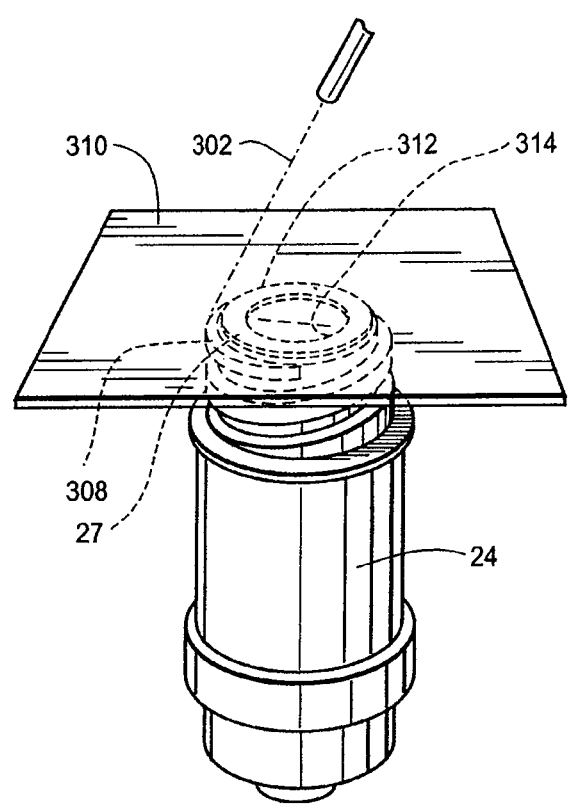
FIG. 20*b* is a schematic illustration of another embodiment of a method of attaching an exposure indicator to a fluid access device.

After the housings have been attached to the sheet of material, the laser beam 302 can be used to cut the sheet of material to form the antiseptic indicators on the top of the housing, For example, referring to FIG. 20b, the laser beam 302 cuts the sheet of membrane material 310 at cut lines 312 and 314 to form the shape of the membrane. As the laser beam 302 cuts the sheet of membrane material 310, the laser beam 302 reactivates the EVA and seals the edges of the membrane to the surface of the housing in a similar manner as described above.

Radiant Energy

In another embodiment of attaching the components of the antiseptic indicator to a fluid access device, radiant energy, such as microwaves, laser beams, e-beam, gamma radiation, UV radiation or infrared radiation, is used to attach such components to the fluid access device.

For example, radiant energy absorbing materials that produce heat or initiate chemical reactions upon exposure to radiant energy are used to bond the materials of an antiseptic indicator to a surface of a fluid access device. Using radiant energy in such a manner takes advantage of the material's natural characteristics and can increase manufacturing efficiency, i.e., reduce manufacturing steps and costs and provide a uniform bond between the indicator and the fluid access device.

Accordingly, when a component of the antiseptic indicator includes a material capable of absorbing radiant energy and converting the energy to heat, this heat-generating capability can be used in the manufacturing process to attach the component and other components to the fluid access device. Such materials that have a good radiant energy absorbing characteristic can include, for example, PVDF or ethanol.

For example, in one embodiment, an antiseptic indicator that includes a microporous antiseptic indicating PVDF membrane which absorbs radiant energy and converts the energy to heat, is positioned against a polycarbonate fluid access device housing. The housing can also be made of other materials, such polycarbonate, acrylic (PMMA), acrylonitrile butadiene styrene (ABS), methyl acrylonitrile butadiene styrene (MABS), polypropylene (PP), cyclic olefin copolymer (COC), polyurethane (PU), polyvinyl chloride (PVC). The PVDF membrane is then exposed to radiant energy, such as microwave energy. As the PVDF membrane absorbs the radiant energy, the membrane converts the radiant energy to heat and increases in temperature. When enough heat is generated by the PVDF membrane the polycarbonate housing melts to bond the membrane to the surface of the fluid access device.

In another embodiment, a hot melt adhesive having energy-absorbing compounds dispersed within or adjacent thereto is used to attach an antiseptic indicator or its components to a fluid access device. Hot melt adhesives, such as ethylene vinyl acetate (EVA), are adhesives that require heat for activation. Upon the application of heat, the adhesive becomes tacky and can be used to bond materials together. When energy-absorbing compounds are dispersed within or adjacent to the hot melt adhesive, the heat generated by such compounds can be used to activate the hot melt adhesive. Such energy absorbing compounds that are suitable for being dispersed in or adjacent to a hot melt adhesive can include, for example, PVDF, ethylene glycol, ethanol, water or polyethylene glycol.

For example, a high energy absorbing compound, such as PVDF powder, is dispersed in or placed on top of a hot melt adhesive, such as EVA. The PVDF/EVA combination is then positioned between an antiseptic indicator, such as a microporous membrane or microporous particles, and the surface of a fluid access. The PVDF/EVA combination is then exposed to radiant energy, such as microwave energy. As the PVDF powder absorbs the radiant energy, it generates heat which actives the hot melt adhesive. Upon activation, the hot melt adhesive becomes tacky and bonds the antiseptic indicator to the surface of the fluid access device.

In another embodiment, radiant energy is passed through a membrane or particles that are made from materials which have a low radiant energy absorbing characteristic or low loss tangent property (tan $\delta = \in''/\in'$, where $\in''$ is dielectric loss and $\in'$ is dielectric constant) to a layer of material that has a high radiant energy absorbing characteristic. Such materials that have a low loss tangent property characteristic can include PP, PE, PC SEBS, SES, COC, acrylic. Because of the low loss tangent of the material, radiant energy can penetrate through the material without creating any damage to the structure of the composition. Additionally, there is very little energy loss as the energy passes through the low loss tangent material, so substantially all of the energy is translated to the layer of material with the high radiant energy absorbing characteristic.

For example, a high radiant energy absorbing material, such as EVA, polyester, polyamide, EMA and PVC or an adhesive including any of these materials, is positioned against the housing of a fluid access device. An antiseptic indicator made from a material having a low loss tangent is then placed onto of the high energy absorbing material so that the high energy absorbing material is between the fluid access device and the antiseptic indicator. Radiant energy can then be passed through the low loss tangent material to the high energy absorbing material. Upon exposure of radiant energy, the high energy absorbing material heats up to form a bond between the low loss tangent material and the surface of the fluid access device. The bond formed between the low loss tangent material and the housing can be the result of melting of the high energy absorbing material or the melting of both of the low loss tangent material of the antiseptic indicator and the surface of the fluid access device.

In another embodiment, the surface of a membrane or particles of an antiseptic indicator are coated with high energy absorbing material. The coated surfaces are then placed against the surface of a fluid access device. Upon exposure to radiant energy, the coated surfaces are activated to generate heat energy which melts the materials together or the coated materials can be activated initiate a chemical reaction, such as a chemical crosslink bond between the materials. In an alternative embodiment, the surface could be coated with photoactive materials or electrically charge particles that can be activated by radiant energy to initiate to generate heat or initiate a chemical reaction.

In another embodiment of attaching a membrane of an antiseptic indicator to a surface of a fluid access device, a coating including a metal component is used to generate heat to initiate bonding between the membrane and a surface of the fluid access device. One example of a metal component is silver particles. Other examples include alumina, cooper, gold or nickel. For example, a microporous antiseptic indicating membrane of an antiseptic indicator is coated with a coating having a metal component. The microporous membrane is then placed in contact with a surface of a fluid access device. The microporous membrane is then exposed to radiant energy which is absorbed by the metal component. In one embodiment, the radiant energy can be selectively applied so as to only heat up particular portions of the coating containing the metal component. This selective heating can be accomplished by, for example, masking the portions of the microporous membrane and the fluid access device that do not require heating. As the metal component absorbs the radiant energy, it produces heat that is used in the bonding process. For example, the heat produced by the metal component melts the surface of the housing to meld the microporous membrane and surface together. Alternatively, the heat generated is used to activate an adhesive layer between the membrane and the surface of the housing.

In a further embodiment, the coating is an antimicrobial coating that includes an oligodynamic metal, such as silver or copper. In this embodiment, a portion of the coating can be covered by a mask during exposure to the radiant energy so that the portions of the coating can retain their antimicrobial properties. Silver has long been known to be an effective antimicrobial metal, and is now available in nanoparticle sizes, from companies such as Northern Nanotechnologies, Toronto, Ontario, Canada, and Purest Collids, Inc., Westampton, N.J., U.S.A. Other oligodynamic metals and compounds are also available from these companies.

Solvent Bonding

In another method of attaching a membrane of the antiseptic indicator to a surface of a fluid access device, a solvent that dissolves the surface of the access device but does not dissolve the membrane is used to initiate the bonding between the membrane and the surface of the access device. The solvent can be applied to the surface of fluid access device by, for example, dipping, wiping or otherwise dispensing the solvent onto the surface. The solvent dissolves and softens the surface of the fluid access device and then the membrane is placed on the surface. As the solvent evaporates, the surface of the housing bonds with the membrane.

For example, methylene chloride is applied to the surface of a polycarbonate fluid access device housing. Methylene chloride dissolves the polycarbonate housing and softens the surfaces. A microporous antiseptic indicating membrane, which does not dissolve in methylene chloride, is then placed on the surface of the housing. The membranes could include PVDF, PP, PE or PTFE. As the methylene chloride evaporates, the polycarbonate surface bonds to the membrane.

In another method of attaching a membrane of an antiseptic indicator to a fluid access device, an adhesive polymer, such as EVA, is dissolved in a low boiling point solvent, such as methylethylketone or toluene. The adhesive polymer/solvent mixture is then dispensed onto either the surface of the fluid access device or the surface of the membrane and the membrane and the surface are brought into contact. After the solvent evaporates, the adhesive bonds the membrane to the surface of the fluid access device.

Insert Molding

Figure 21A:
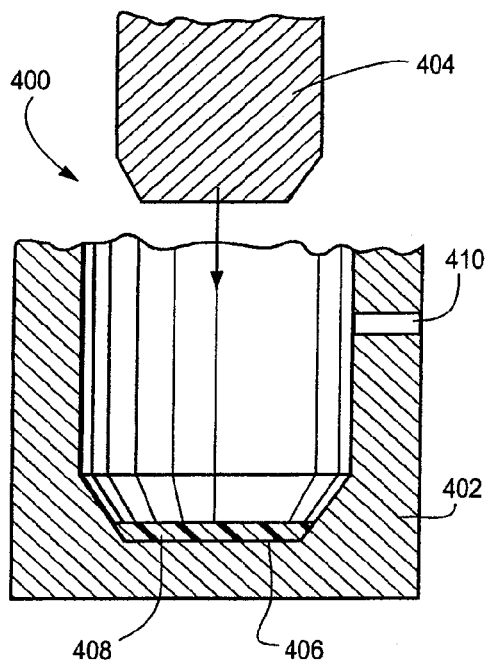
FIGS. 21*a* and 21*b* are illustrations of one embodiment of an injection molding process that can be used to attach an exposure indicator to a fluid access device.
Figure 21B:
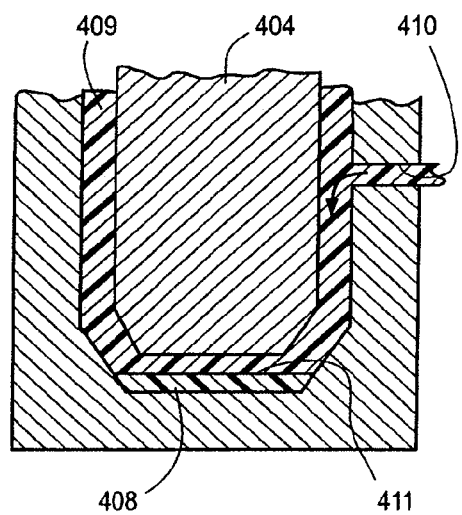

In one embodiment, membranes or microporous particles of an antiseptic indicator, such as the microporous antiseptic indicating membranes and particles described herein, are attached to a housing or a valve member of a fluid access device during an insert molding or decorative molding process. The insert molding process can be used to bond an antiseptic indicator to elastomeric, such a elastomeric gland, or thermoplastic housing materials. For example, referring to FIG. 21 a, there is shown an injection mold 400 for forming a fluid access device housing. The mold 400 includes a cavity 402 and a core 404. The surface 406 of the cavity 402 corresponds and forms the upper or inlet surface of the housing. Prior to the molding process, a microporous antiseptic indicating membrane 408 having an adhesive backing, such as an EVA backing is positioned against the surface 406 of the cavity 402. Additionally, the membrane can be made of PVDF, PE or PTFE or any other suitable microporous polymer membrane. Alternatively, a sheet of material including a plurality of microporous antiseptic indicating particles deposited thereon or dispersed therein is positioned against the surface 406. In one embodiment, the microporous particles are introduced into the sheet during an extrusion or calendaring process. Alternatively, the microporous particles are pressed into the sheet of material and can be mechanically bonded to the sheet Referring to FIG. 21b, once the microporous membrane 408 is in the desired position, it can be held in place by a vacuum line. The mold 400 is then closed and the material 410 of the housing, such polycarbonate or any other suitable polymer for forming the housing, is injected into the mold 400 to form the housing body. As the mold and the materials cool to form the body of the housing, the EVA backing firmly bonds the membrane 408 to the upper surface 411 of the housing. After the mold has sufficiently cooled, the housing with the microporous antiseptic indicator attached thereto is removed.

Two-Shot Molding

In another embodiment, antiseptic-indicating microporous particles of an antiseptic indicator are attached to a fluid access device housing by a two-shot molding process.

Figure 22A:
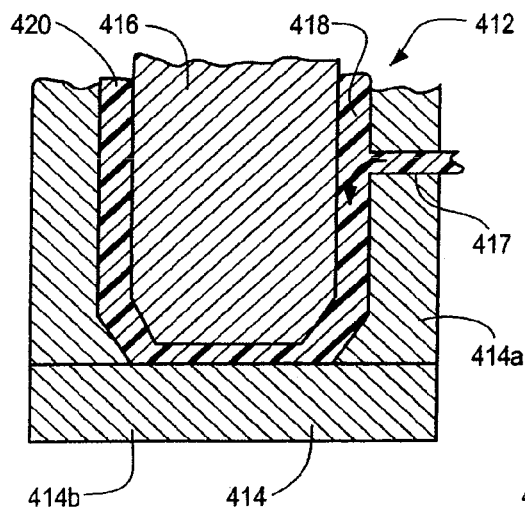
FIGS. 22*a*, 22*b* and 22*c* are illustrations of another embodiment of an injection molding process that can be used to attach an exposure indicator to a fluid access device.
Figure 22B:
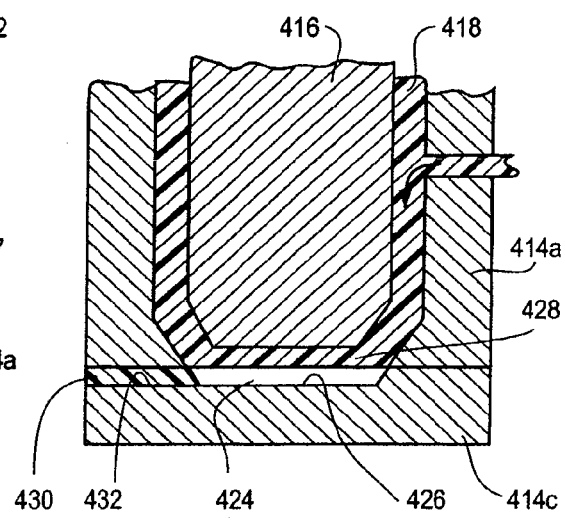

For example, referring to FIG. 22a, there is depicted a mold 412 including a cavity 414 and a core 416. The cavity 414 can include an upper cavity 414a and a lower cavity 414b. The upper cavity 414a forms the body of the housing and the lower cavity 414b forms the top surface of the housing. During the molding process, a polymer material 418, such as a thermoplastic material, for example polycarbonate, is injected through a mold runner 417 into the mold to form the housing 420 of the fluid access device. The material 418 is then allowed to partially cool. After the material 418 has cooled to the desired temperature, the lower cavity 414b is removed and replaced with a second lower cavity 414c (FIG. 22b).

Figure 22C:
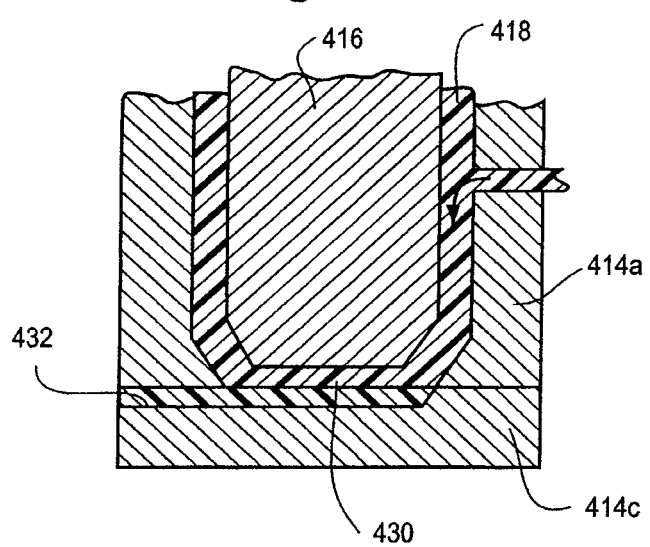

When second lower cavity 414c is in position, the cavity 414 includes a space 424 between the surface 426 of lower cavity 414c and surface 428 of material 418. The space 424 will receive a second polymer material 430 from mold runner 432. The second polymer material 430 includes antiseptic-indicating microporous particles suspended therein. The polymer material 430 can include rubber, silicone or EVA having PVDF microparticles dispersed therein. Referring to FIG. 22c, the polymer material 430 is delivered or shot through a supply conduit or mold runner 432 into the space 424 of cavity 414. As the materials 418, 430 cool, they bond together to produce a housing having antiseptic indicating microporous particles attached thereto.

Applying Coatings to the Mold

FIGS. 23a-23d illustrate an alternative molding process that can be used to apply an antiseptic indicator and/or an antimicrobial coating to the housing of a fluid access device during the molding process. The molding process can be applied to form thermoplastic or elastomeric elements. FIG. 23a illustrates a mold 450 that can be used in the present molding process. The mold 450 includes cavity 452, a first side core 454 and a second side core 456. The first side core 454 includes a surface 458 that corresponds to and forms the top surface of the inlet portion of housing, and the second side core 456 includes a surface 460 that forms the bottom surface the outlet portion of the housing. Additionally, the first and second side cores 454, 456 each include a side core pin 462, 464 that mate with each other when the mold is closed (FIG. 23b). The mated side core pins 462, 464 form the fluid path through the access device housing.

In one method, an antimicrobial agent is selectively applied to the surfaces of the mold that create the fluid path. During the molding process, the antimicrobial agent is transferred from the surfaces of the mold to the fluid path surfaces of the access device to provide an antimicrobial coating on the surfaces of the fluid path. For example, an antimicrobial coating 463, such as a solution of silver sulfadiazine, is applied to the core pins 462 and 464 prior to the molding process. The antimicrobial coating 463 can be applied by dipping the core pins 462, 464 into the coating or by spraying the coating onto the core pins. Furthermore, in one embodiment, the antimicrobial coating 463 includes a mold release solution so that the coating could provide the dual function of applying an antimicrobial agent and providing mold release. For example, the coating can include a silicone mold release solution or other mold release solution, such as Slide Universal Release, Slide Products, Inc., Wheeling, Ill. In one embodiment, the antimicrobial agents include oligodynamic compounds, such as silver sulfadiazine, silver nanoparticles, or any other suitable oligodynamic compound.

In one embodiment referring to FIGS. 23c and 23d, a sprayer head 466 for selectively applying a coating is used to apply a coating to the core pins. The sprayer head 466 limits or confines the coating to only the desired surface to be treated. In one embodiment, the sprayer 466 includes a base 468 having an outer cylindrical wall 470 and an inner cylindrical wall 472 extending therefrom. The outer wall and inner wall can be a shape other than cylindrically shaped and can be positioned generally coaxially. The top portions 474, 476 of the outer wall 470 and the inner wall 472 are connected and the outer and inner walls 470, 472 are spaced apart to define a space 478 therebetween. A fluid supply conduit 480 extends through the base 468 and communicates with the space 478 to supply fluid thereto. The inner wall 472 defines an inner cavity 482 that is configured to receive each of the core pins 462 and 464, as illustrated in FIG. 23d. The inner wall 472 also includes openings 484 that extend through the inner wall and communicate with the space 478.

In operation, referring to FIGS. 23c and 23d, the sprayer head 466 is positioned so that the core pin 464 is received within the cavity 482. The sprayer head 466 is then activated so that fluid 486, such as an antimicrobial fluid, flows from the fluid conduit 480 into the space 478 and out of the openings 484 onto the core pin 464. Because the sprayer head 466 covers the core pin 464 while the fluid 486 is being applied, the application of fluid is contained to or selectively applied to the core pin and does not spread to other parts of the mold. After the pin 464 has been sufficiently coated, the sprayer is removed. In one embodiment, the sprayer can be robotically controlled to apply the coating to either one or both of the core pins.

After the core pins 462, 464 have been coated with the antimicrobial agent 463, the mold is closed and the material that is to form the housing is injected into the mold. While the housing is being molded, the antimicrobial agent 463 is transferred from the core pin to the surface that defines the fluid passageway of the housing. After the materials have sufficiently cooled, they are removed from the mold and a fluid access housing including antimicrobial agents disposed on the surfaces of the fluid pathway is formed.

In a further embodiment, prior to the molding processes, an antiseptic indicator material, such as any of the microporous particles or solvatochromic dyes described herein or any other suitable indicator material, are suspended in a coating solution that is selectively applied to the surface 458 of the side core 454 that forms the upper surface of the inlet housing. During the molding process, the microporous particles are transferred from the surface 458 and bonded to the upper surface of the inlet housing, thereby creating an antiseptic indicator. In a further embodiment, the microporous particles are dispersed within a mold release solution so that the mixture provides the dual purpose of attaching the antiseptic indicator to the housing and provides a mold release characteristic. For example, the coating can include a silicone mold release solution or other mold release solution, such as Slide Universal Release, Slide Products, Inc. Wheeling, Ill. and an indicator material.

Protective Member

During the manufacturing, packing and shipping of the fluid access device, the antiseptic device can be exposed to environments and materials, such as lubricants, antimicrobial agents and different forms of energy, that can cause damage to the antiseptic indicator and affect its operability. For example, during the manufacturing of a fluid access device, lubricants are commonly applied to the valve member to enhance and ensure the performance of the valve member. For instance, when the fluid access device includes a pre-slit septum, silicone will oftentimes be applied to the slit after it has been cut to prevent the slit from closing-up and reknitting. If the silicone is dripped onto or otherwise migrates to an antiseptic indicator that includes a microporous material which changes transparency when wetted, the silicone will wet the microporous material, keeping the material in its transparent state. Thus, the operability of the microporous material would be impaired by the silicone oil.

In order to protect the antiseptic indicator from such damage, in one embodiment, the fluid access device includes a protective member that protects the antiseptic indicator. The protective member provides a physical barrier that prevents contaminants from coming into physical contact with the antiseptic indicator. In one embodiment, the protective member also provides a shield that shields the antiseptic indicator from heat and other energies. Furthermore, the protective member can completely protect the antiseptic indictor or it can selectively protect portions of the antiseptic indicator.

Figure 24A:
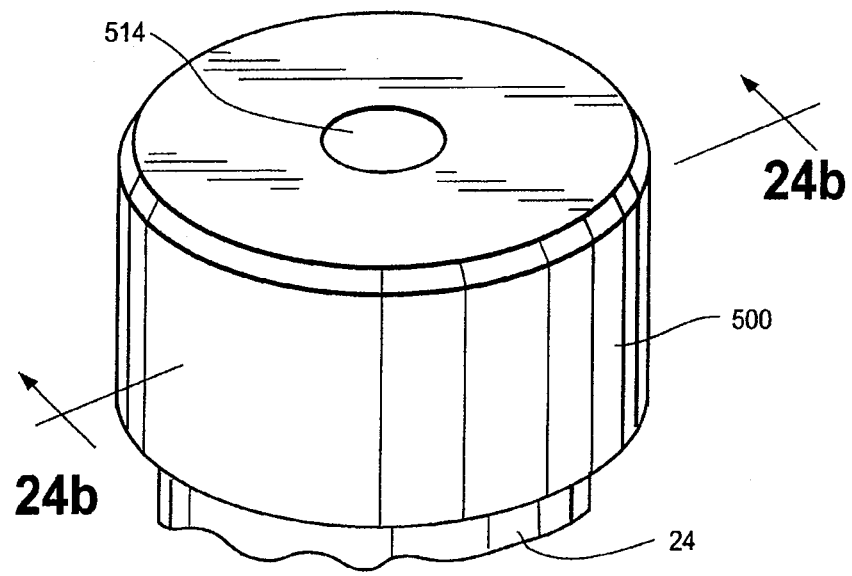
FIG. 24a is a perspective view of one embodiment of a protective member of a fluid access device.
Figure 24B:
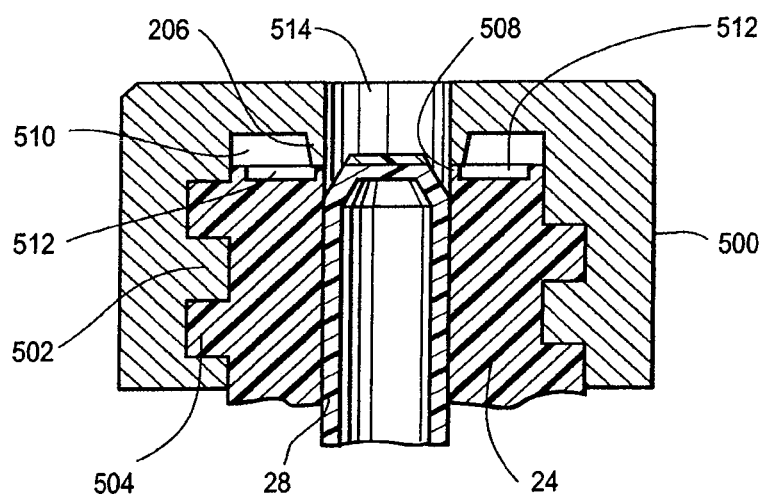
FIG. 24b is a cross-sectional view of the protective member of FIG. 24a, shown disposed on a fluid access device.

Referring to FIG. 24a-24b, in one embodiment, the protective member includes a cap 500 that is removably attachable to the housing 24 of a fluid access device. The cap 500 can be removably attached to the housing by a variety of methods, such as by an interference fit or by a releasable adhesive. In the embodiment shown, the cap 500 includes a threaded portion 502 that mates with the threaded portion 504 of the inlet of the housing 24. In an alternative embodiment, the cap 500 is snap-fitted onto the housing. Additionally, the cap can be removed at any time during the manufacturing, packing or shipping process or by the end user.

The cap 500 also includes a circumferential barrier portion 206 that extends downward and contacts the surface 508 of the inlet housing to form a protective cavity 510 and a barrier seal that prevents containments from coming into contact with the antiseptic indicator 512. Optionally, the cap 500 can also include a central opening 514 therethrough that allows access to the valve member 28. Furthermore, in one embodiment, the cap 500 is made of a material the shields the antiseptic indicator form heat and other energies.

In an alternative embodiment, referring to FIGS. 25a and 25b, the protective member is a releasable protective liner 518 that is disposed on the antiseptic indicator 520. The protective liner 518 is attached to the antiseptic indicator 520 by, for example, a releasable pressure sensitive adhesive that has a greater affinity to the release liner 518 than to the antiseptic indicator 520 so that the adhesive releases from the antiseptic indicator and remains with the release liner when release liner is removed. In the illustrated embodiment, the release liner 518 has a tab 522 that allows for easy grasping and pulling to facilitate removal of the release liner. The release liner 518 can be removed prior to packaging or by the end user.

In an alternative embodiment, the protective member can be employed to protect the surface of the housing from contaminants prior to the attachment of the antiseptic indicator to the surface of the housing. For example, the protective member could be attached to the housing to protect the surface of the inlet during the application of the antimicrobial agents to the housing. If an antimicrobial agent is located on the surface of the inlet housing, the antimicrobial agent can affect the attachment of the indicator material to the surface. After the antimicrobial agent has been applied to the housing, the protective member is removed. The indicator material is then attached to the surface.

FIGS. 25c-25e illustrate one method of manufacturing an antiseptic indicator with a releasable protective liner. Referring to FIG. 25c, there is shown a substrate 525 that is used to manufacture an antiseptic indicator with a protective release liner. The substrate 525 includes a releasable liner 526, a releasable adhesive layer 528, an antiseptic indicating microporous material 530 and a permanent adhesive layer 532. The releasable adhesive layer 528 releasably attaches the release liner to the microporous material and the permanent adhesive layer 532 can be used to attach the antiseptic indicator to a surface of a medical device after the indicator has been formed.

Turning to FIG. 25d, in one method of manufacturing an antiseptic indicator from substrate 525, a center hole is punched through all of the layers 526-532 of the substrate along dotted line 534. After the center hole has been punched, a ring is cut along cut line 536 through the top adhesive layer 532 and the microporous membrane layer 530 to form the shape of the microporous membrane and the top adhesive layer. A cut is then made along cut-line 538 through all of the layers to form the shape of the release liner and the pull tab. To cut the shape of the release liner, the cut made along cut line 528, can be partially co-extensive with previous cut line 536.

Figure 25F:
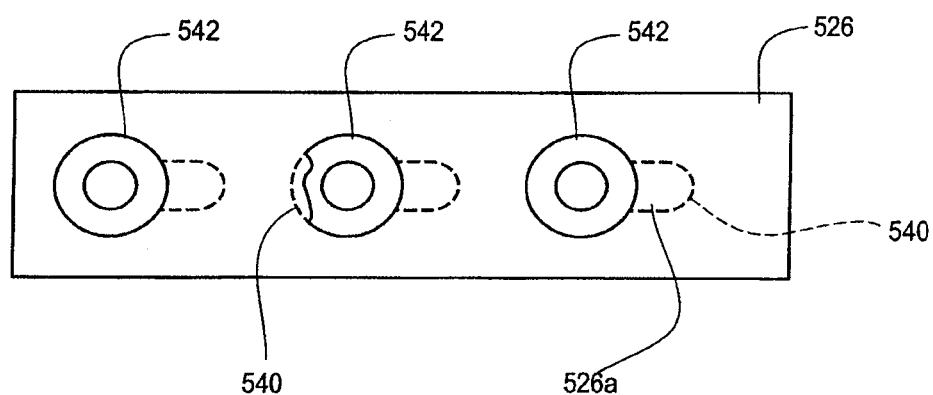
FIG. 25f is a plan view of one embodiment of a sheet of release liner material having a plurality of antiseptic indicators attached thereto.

In an alternative embodiment, a continuous cut is made through the layers 532, 530 and 528 along cut-line 538 Then a perforated or non-continuous cut is made in release layer 526 along cut-line 538 to create a frangible perforation 540 between the release liner layer 526 and the now formed releasable protective member 526a. (FIG. 25f) The material of layers 532, 530 and 528 surrounding the cut-out indicator is then removed. Referring to FIG. 25f, the antiseptic indicators 542 are attached to the sheet 526 by the frangible perforation 540. To remove the individual antiseptic indicators 542 from the sheet of release liner 526, the perforation 540 is broken. In one embodiment, a sheet of release liner material 526 containing a plurality of antiseptic indicators 542 attached to the sheet by perforations 540 is placed over a plurality of fluid access device housings. The fluid access device housings are arranged and orientated so that each housing is aligned with an antiseptic indicator. During or after attachment of the antiseptic indicator to the housing, by for example, a heat compression process, the frangible perforation is broken to remove the antiseptic indicator from the sheet of release liner. The result is a fluid access device housing including an antiseptic indicator with a release liner.

Referring to FIG. 25e, when the cutting process is finished, an antiseptic indicator 540 with a protective release liner 526a is formed. In addition to the release liner 526a, the antiseptic indicator also includes a releasable adhesive layer 528a removably attaching the release liner 526a to the microporous membrane layer 530a. As explained above the releasable adhesive layer 528a should have a releasable characteristic as to the microporous membrane 530a so that the adhesive 528a releases from the membrane and remains with the releasable liner 526a when the liner is removed. Additionally, the antiseptic indicator 540 includes a permanent adhesive layer 532a for attaching the indicator to the surface of a medical device.

Optionally, if the antiseptic indicator 540 is not going to be attached to the housing for some time, the adhesive layer 532a may include a release liner (not shown) attached thereto. The release liner protects adhesive layer 532a prior to assembly with the fluid access device. The liner is peeled off prior to attachment of the adhesive to the housing. The release liner can be attached to the adhesive layer 532/532a before or after the cutting process. Additionally, a release liner on the layer adhesive layer 532/532a could be used regardless of whether the antiseptic indicator includes a protective member.

Solvatochromatic Dyes in the Surfaces

Solvatochromic dyes may be incorporated into the surfaces of the device or may be attached via a membrane or a coating. Such a coating is adherent to the Luer Access Device (LAD) or other medical device, and also allows small amounts of liquid or vapor to penetrate its surface. Included in these coatings are acrylic coatings, such as those made from products available from Sartomer Co., Philadelphia, Pa., U.S.A. The sodium salt of Reichardt's dye was incorporated into the acrylic coatings whose recipes appear below in a very small amount, about 0.1%.

TABLE 1

Acrylic Radiation Curable Compositions

| Chemical | Formula and amount, grams MB1 | MB2 | MB3 | MB4 | MB5 | MB6 |
|---|---|---|---|---|---|---|
| Irgacure 651* | 1.25 | 1.25 | 1.25 | 1.25 | 1.25 | 1.25 |
| SR 285 | 4.9 | 5.01 | 5.0 | 2.56 | — | 2.54 |
| SR 351 | 3.79 | 3.72 | 3.75 | 3.79 | — | 2.5 |
| SR 339 | | | | | | 3.72 |
| CD 9038 | 4.94 | 5.01 | 7.5 | 5.0 | 10.0 | 10.04 |
| DMA** | | 2.49 | | | | |
| NVP** | 2.49 | | | 2.53 | 2.5 | 2.51 |
| SR259 | 7.56 | 7.5 | 7.56 | 7.57 | 2.5 | 2.53 |

*Irgacure 651 is a photoinitiator available from Ciba.
**DMA is dimethylacrylamide and NVP is N-vinyl-pyrolidone, both available from Aldrich.
The remainder of the ingredients are from the Sartomer Co.

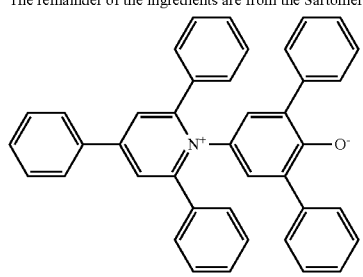

Reichardt's Dye Structure:

Each formula listed above was formulated and a thin coating was spread onto polycarbonate, the coatings about 0.003 to 0.006 inches thick. The coating was then exposed to 0.5 J/cm$^2$ to 1.8 J/cm$^2$ of irradiation from a lamp at 350 nm (wavelength). Cure was monitored by the disappearance of the acrylated unsaturated bond at 810 cm$^{-1}$. Each of these formulas produced a firm coating that was adherent to polycarbonate. The adhesion of each was tested and was sufficiently adherent that it was difficult to remove them by mechanical scraping. In repeated testing, a swab of isopropyl alcohol was rubbed onto the surface of the coating. The dye repeatedly changed from green color to dark blue color. The dye then returned to green color after a few minutes. In addition, these formulations were also tested on surfaces or housings made of materials such as acrylic, ABS, nylon, and PET. The acrylic coating is permeable to IPA and IPA/water solutions, or to other antiseptic solutions.

In addition to permeable acrylic coatings, a number of other polymer families may be used to provide a surface coating for luer access device housings. For instance, a number of elastomers, at least latex rubber, isoprene, styrene-butadiene rubber (SBR) and chloroprene rubber (neoprene), are well known to be permeable to IPA and 70% IPA/water mixtures. Other polymer systems include epoxies, such as the systems similar to the Mastertop 1710, 1730 and 1740 vapour permeable epoxy overlay systems available from BASF Corporation. Urethanes also form tough, adherent coatings that can encapsulate the dyes discussed above, and are permeable to isopropyl alcohol or other solvents. See U.S. Pat. No. 5,024,875, which is hereby incorporated by reference in its entirety. In addition, a number of polyesters and vinyl ester systems, such as those available from Dow Chemical Co., Midland Mich., U.S.A., may also be used.

It is possible to incorporate the dye into a coating, preferably a permeable coating, that may be applied to luer access device (LAD) housings. LAD housings are typically made from polycarbonate (PC), but they may also be made from acrylic (PMMA), acrylonitrile butadiene styrene (ABS), methyl acrylonitrile butadiene styrene (MABS), polypropylene (PP), cyclic olefin copolymer (COC), polyurethane (PU), polyvinyl chloride (PVC), nylon, and polyester including polyethyleneterephthalate (PET). There are many coatings that will firmly adhere to the above mentioned plastics, including epoxies, polyesters, and acrylics. An example is seen in FIG. 14c, in which housing 24 includes top permeable membrane 82 with an encapsulated dye 84.

Solvatochromic Dyes

There are many solvatochromic dyes that may be used as color indicators in embodiments. Examples includes, Reichardt's dye, discussed above, the chloride salt of 1-acryloyl-4,6-dichloro-2-[2-(1-acrylamidohexyl-4-pyridinio)vinyl] phenolate (structure 10 below), the basic salts of 4,6-dichloro-2-[2-(6-acrylamidohexyl-4-pyridinio)vinyl] phenolate (structure 11 below), and the basic salts of 4,6-dichloro-2-[2-(6-amino-hexyl-4-pyridinio)vinyl]phenolate (structure 12 below).

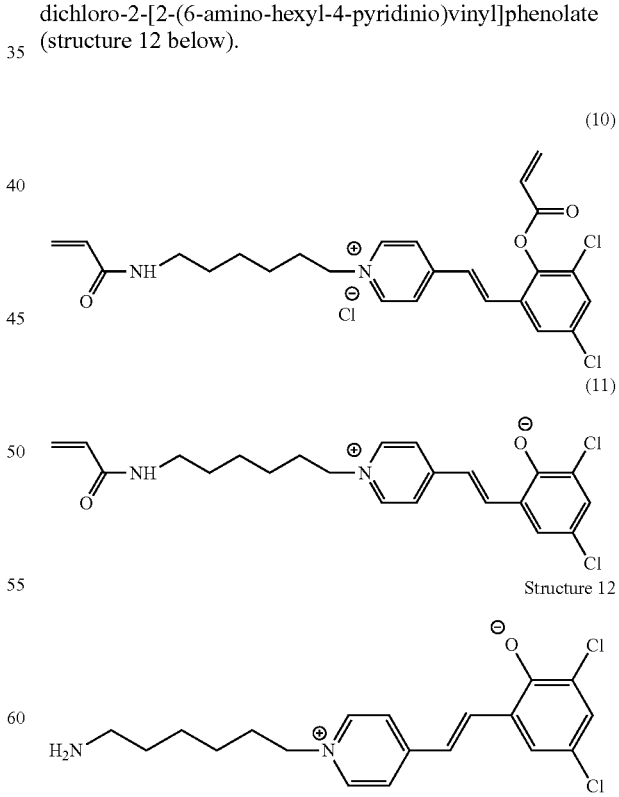

A general structure for a solvatochromic dye that has been found useful in the present embodiments appears in structure 13 below. In this structure, R1 may be amine or acrylamido, R2 is C4 to C20 aliphatic, R3 is ethene, butadiene, or hexatriene, R4 and R6 are as discussed below, and R5 may be one of hydrogen and O and R7 may be the other of hydrogen and O. Either or both of the chlorides at R4, R6, may be replaced by iodide, bromide, or fluoride. The O group in the 1-position could instead be placed in the 5-position between the chlorides. It is possible that nitrate, —NO$_2$, alkoxy, such as methoxy, ethoxy, may also yield a solvatochromic dye. Note that a number of substations on the benzene ring are readily available. For example, several salicylaldehyde compounds with halogen atoms in the 3, 5 positions are readily available from manufactures, such as Sigma-Aldrich, St. Louis, Mo., USA. When the salicylaldehyde molecule reacts with its aldehyde functionality to the pyridine ring on structure 5, the 3, 5 positions on the salicylaldehyde molecule become the 4, 6 positions on the phenol/phenolate product formed.

Compound 13

(13)

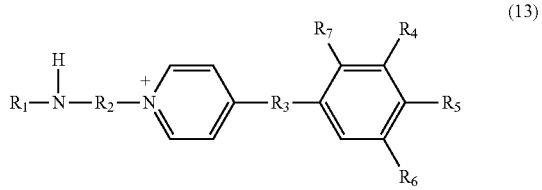

These are only a few of many examples of useful solvatochromic dyes that may be used in these applications. There are many other solvatochromic dyes that could be used. As noted above, the principal requirements are the ability to reversibly change color when swabbed, e.g., with IPA. Without being bound to any particular theory, it is believed that the conjugation between the pyridine ring and the benzene ring, with the intermediary double bond, whether one, two, or three, that accounts for the solvatochromic activity in the new structures. Since these structural features are present in merocyanine dyes, it is believed that a number of these dyes would also be effective as indicators for swabbing, whether incorporated into a coating, as the acrylics described above, or used as part of a surface treatment. Of course, merocyanine dyes typically have a phenoxide ring, rather than a substituted benzene ring. The phenoxide ring functions as the aromatic donor and the pyridine or pyridinium ring functions as the acceptor. Of course, in the new structures, the benzene ring is the donor and the pyridine ring is the acceptor. Thus, it is believed that merocyanine dyes, structure 14 below, with conjugated pyridinium-phenoxide rings (having resonance with a pyridine-benzene structure)

(14)

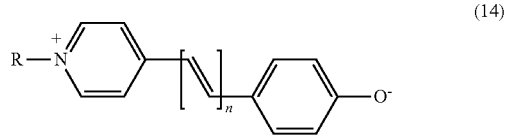

are also suitable. Examples include 1-methyl-4-(4'-hydroxybutyl)pyridinium betaine and Brooker's merocyanine dye, 4'-hydroxy-1-methylstilbaxolium betaine.

Other solvatochromic dyes may also be used, such as an abundance of previously-known dyes, and for which the small change from their normal environment to a slightly acidic environment, such as the 6-7 pH range of IPA, will produce a color change. The table below lists a number of these dyes and their colors before and after. Note that the "before" environment of the coating or LAD housing material may be altered, such as by making it basic, by simple adjustments during the formation of the coating, the method of treating the surface, or the species used for attaching the dye. A few examples of solvatochromic dyes are presented in Table 1 below.

TABLE 1

Solvatochromic Dyes

| Dye | First state pH | Color | Second state, pH | Color |
|---|---|---|---|---|
| Bromocresol purple | 6.8 | blue | 5.2 | yellow |
| Bromothymol blue | 7.6 | blue | 6.0 | yellow |
| Phenol red | 6.8 | yellow | 8.2 | red |
| Cresol red | 7.2 | red | 8.8 | Red/purple |
| Methyl red | 4.2 | pink | 6.2 | yellow |
| Reichardt's Dye | Unknown | green | 6-7 | dark blue |
| Morin hydrate | 6.8 | red | 8.0 | yellow |
| Disperse orange 25 | 5.0 | yellow | 6.8 | pink |
| Nile red | Unknown | blue/purple | 6-7 | bright pink |

These and many other solvatochromic and merocyanine dyes many be used in applications according to this application. Other solvatochromic dyes include, but are not limited to, pyrene, 4-dicyanmethylene-2-methyl-6-(pdimethylaminostyryl)-4H-pyran; 6-propionyl-2-(dimethylamino)naphthalene; 9-(diethylamino)-5H-benzo[a]phenoxazin-5-one; phenol blue; stilbazolium dyes; coumarin dyes; ketocyanine dyes, Reichardt's dyes; thymol blue, congo red, methyl orange, bromocresol green, methyl red, bromocresol purple, bromothymol blue, cresol red, phenolphthalein, seminaphthofluorescein (SNARL) dyes, seminaphtharhodafluor (SNARF) dyes, 8-hydroxypyrene-1,3,6-trisulfonic acid, fluorescein and its derivatives, oregon green, and a variety of dyes mostly used as laser dyes including rhodamine dyes, styryl dyes, cyanine dyes, and a large variety of other dyes. Still other solvatochromic dyes may include indigo, 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl)julolidine (DCVJ); phenol blue; stilbazolium dyes; coumarin dyes; ketocyanine dyes; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Other suitable dyes that may be used in the present disclosure include, but are not limited to, 4-[2-N-(substituted-1,4-hydropyridin-4-ylidine)ethylidene]cyclohexa-2,5-di-en-1-one, red pyrazolone dyes, azomethine dyes, indoaniline dyes, and mixtures thereof.

Other merocyanine dyes include, but are not limited to, Merocyanine dyes (e.g., mono-, di-, and tri-merocyanines) are one example of a type of solvatochromic dye that may be employed in the present disclosure. Merocyanine dyes, such as merocyanine 540, fall within the donor—simple acceptor chromogen classification of Griffiths as discussed in "Colour and Constitution of Organic Molecules" Academic Press, London (1976). More specifically, merocyanine dyes have a basic nucleus and acidic nucleus separated by a conjugated chain having an even number of methine carbons. Such dyes possess a carbonyl group that acts as an electron acceptor moiety. The electron acceptor is conjugated to an electron donating group, such as a hydroxyl or amino group. The merocyanine dyes may be cyclic or acyclic (e.g., vinyl analogs of amides of cyclic merocyanine dyes). For example, cyclic merocyanine dyes generally have the following structure 15, in association with structure 14 above:

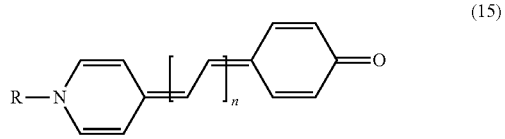

(15)

wherein, n is an integer, including 0. As indicated above by the general structures 14 and 15, merocyanine dyes typically have a charge separated (i.e., "zwitterionic") resonance form. Zwitterionic dyes are those that contain both positive and negative charges and are net neutral, but highly charged. Without intending to be limited by theory, it is believed that the zwitterionic form contributes significantly to the ground state of the dye. The color produced by such dyes thus depends on the molecular polarity difference between the ground and excited state of the dye. One particular example of a merocyanine dye that has a ground state more polar than the excited state is set forth above as structures 14 and 15. The charge-separated left hand canonical 14 is a major contributor to the ground state, whereas the right hand canonical 15 is a major contributor to the first excited state. Still other examples of suitable merocyanine dyes are included in the related application concerning immobilization of dyes which is being filed on the same day as the present application, and which is incorporated by reference herein.

Radiation (or Thermally) Curable Resin Containing Opaque Dispersed Phase

As noted herein, the solvatochromic dye embodiments of the present invention may be incorporated into a housing or into a coating for application to the housing. It has also been discovered that the dye may be incorporated into the housing a dispersed phase of the dye, incorporating the dye into a mixture with a resin, infiltrating the dye and resin into the surface of the housing by crazing or other methods, and then curing the resin. The surface of the housing, e.g., a polycarbonate housing, is crazed, i.e., a multitude of fine, tiny cracks are introduced into the surface, usually by wiping the surface with a solvent. The appearance is a matte finish, i.e., a rather dull, opaque, and not shiny surface. An example is given in FIG. 15f, in which housing 24 includes an upper surface 110 with an antiseptic indicator 138. Antiseptic indicator 138 includes a bottom layer 140, a radiation curable coating having an upper crazed portion 142 with a plurality of microcracks 144. If the solvent forms pores, the coating may appear as FIG. 15e, a film 128 with a surface 132 having microcracks 130 and pores 136.

Many solvents are effective in creating surfaces that indicate whether swabbing with alcohol has recently taken place. Without being bound to any particular theory, it is believed that this is because the solvents dissolve the surface of the membrane or polymer, causing swelling or distortion, or even dissolving the polymer and redepositing it on the surface. Either process results in voids in the surface, making the polymer porous and permeable to the isopropyl alcohol wipe that is administered. In general, after treatment, the surface appears to be crazed and to be opaque, i.e., it is not possible to see through the polymer disc or membrane. Without being bound to any particular theory, it is believed that the mixture of polymer and air appears to be opaque because the two have different indices of refraction, with air having an index of refraction of about 1, and the polymer surface having an index of refraction from about 1.25 to about 1.6. In some instances, the dye itself is not needed, merely a treatment to induce the two phases.

One theory is that light incident on the surface is refracted in one direction by the air and in another by the polymer. A uniform surface with a uniform index of refraction bends light and transmits it, allowing the user to see the surface as transparent or translucent. Instead, the expanded or swelled surface has at least two indices, one for air that bends light one way, and another for a very nonuniform polymeric surface. Thus, even though both phases may be transparent or translucent, an observer sees the surface as opaque. However, when a liquid penetrates the surface, such as when the surface is wiped, the air is displaced. The surface then takes on a transparent look, at least until the liquid evaporates or is otherwise displaced.

For example, 2-octanone or a 20/80 mixture of acetone/p-xylene may be eye-dropped or spun-coated onto a test specimen or a disc (or onto a housing). In one example, polycarbonate discs were obtained from the same material used to make luer access device housings. Spin coating was accomplished by using an eye-dropper to place a drop or two of solvent onto a disc or a housing. The disc or housing was then placed into a spinner. The 2-inch diameter disc was then spun up to about 4000 rpm, for about 15-20 seconds. This creates a crazed area, an area with a plurality of fine, tiny cracks. These solvents preferentially dissolve the polycarbonate and re-deposit the dissolved carbonate as globules on the surfaces, where the small globules act as a powder. The surface may then be used as desired or may be sealed with a UV-curable coating or other coating as desired. The UV coating may be MB-6 or may be another acrylate coating. Other coatings may also be used, such as melamines and methacrylics. A UV lamp that irradiates at 320-350 nm (wavelength) is suitable. Xenon, mercury, hydrogen, or tungsten type lamps may be used. Lamps from Fusion UV Systems, Inc., Gaithersburg, Md., U.S.A., and Phillips, Inc., Eindhoven, the Netherlands. Other radiation sources may be used. Additionally, the surface may be sealed with a microporous thin polymer film, such as the microporous film discussed above with respect to FIG. 15c.

In some experiments, a crazed area was created on a dog-bone-type polycarbonate tensile specimen, from the same material described above for discs, by applying the solvent with an eyedropper, and waiting for evaporation. The polycarbonate surfaces tested had a bluish tint from the color included in the polycarbonate resin. The surfaces were crazed by applying a solvent, or were exposed for a longer period of time to the solvent, to create not only a crazed surface, but one with redeposition of the dissolved polymer. The crazes appeared, forming a bluish-white, powder-like residue on the surface. A thin coating of the MB-6 acrylic formula above, estimated at 2-3 mils maximum thick, was then applied as a sealant, to preserve the crazes and the fine white powder. The crazed surface of the specimen was opaque white. Upon swiping with IPA, the surface turned a bluish-white, and became clear after 15 seconds to 15 minutes. With MB-6, the time should be 15 minutes. With no coating, the time for recovery of appearance can be 30-60 seconds.

Using MB-6, or other acrylic or methacrylic coatings, the time for recovery may be tailored from about 30-60 seconds to about 15 minutes or more. The tailoring is accomplished by carrying the cross-link density of the polymer system. A higher degree of cross linking yields a polymer coating that is less permeable and thus takes longer for IPA/water to penetrate, and also from which to evaporate. A lesser degree of cross linking makes it easier for the wiping solvent to penetrate, and also makes it easier for the solvent to escape. Thus, in a system such as MB-6, with a higher degree of cross-linking, the appearance changes takes longer. As can be seen from Table 2, below, the octanone and the 20/80 acetone/p-xylene solvents worked well, and the resulting crazing was durable, meaning that it did not smear and was able to hold up for at least 100 wipings and insertions/removals. The surface appeared to be a matte surface, not shiny.

TABLE 2

Solvents and Polycarbonate Discs

| Description | Conc., % | Pattern Color Upon Solvent Treatment | Color Change After IPA Contact | Durability | Behavior |
|---|---|---|---|---|---|
| 1,2-Dichlorethane | 100% | NA | NA | NA | Dissolves surface but forms circular trace |
| 2-Octanone, 98% | 100% | Whitish blue | Clear | Durable | Spreads out |
| Acetone/p-xylene | 20%/80% | White/Blue | Clear | Durable | Solution Spreads out on tensile bone |
| Benzyl Alcohol, anhydrous 99.8% | 100% | Powdery blue | Almost wipes clear | Scratchable | Not a uniform shape, spreads out |
| Benzyl Alcohol/p-xylene | 10%/90% | Whitish blue | Light blue | Durable | NA/Applied on leur part only |
| Calcium Stearate/p-xylene | 1%/99% | Bright white | Clear | Rubs off | Circular but spreads out. Cracks form as solution dries |
| Chlorobenzene | 100% | Light blue | Somewhat clear | Durable | Circular, some pores visible |
| Chloroform | 100% | NA | NA | NA | Evaporates but reappears/smears when acetone is applied |
| Cumene, 98% | 100% | White/blue | Clear | Scratchable | circular |
| Cumene, 98%/p-xylene | 5%/95% | White | Clear | Durable | circular |
| Cyclohexanone | 100% | White-blue | Doesn't really change | Sturdy/durable | Uniform circle |
| Cyclohexanone/p-xylene | 20%/80% | Blue | Doesn't really change | Durable | Uniform circle |
| Cycloexanone/p-xylene | 50%/50% | White | Clear | Rubs off | Spreads out |
| Dichloro-Methane | 100% | NA | NA | NA | Dissolves surface |
| Dimethyl Sulfoxide/p-xylene | 5-10%, bal. p-xylene | White-blue | Light blue | Durable | Circular, pores visible |
| Dimethyl Sulfoxide/p-Xylene | 20%/80% | White-blue | Light blue | Durable | Circular than branches out. Visible pores and cracks |
| Dimethyl Sulfoxide/p-Xylene | 30%/70% | White blue | Doesn't really change | Durable | Circular, pores visible |
| Dimethyl Sulfoxide/p-xylene | 50%/50% | White blue | Doesn't really change | Durable | Circular, pores visible, formation not uniform |
| Ethyl Acetate, 99.5% | 100% | White | Light blue | Scratchable | Not uniform, spreads out |
| Ethyl Acetate, 99.5%/p-xylene | 20%/80% | White | Light blue | Scratchable | Not uniform, spreads out |
| Ethyl Ether | 100% | NA | NA | NA | Evaporates |
| Ethyl Ether/p-Xylene | 20%/80% | White | Light blue | Somewhat durable | Not uniform, spreads out, cracks formed |
| Hexane | 100% | NA | NA | NA | Evaporates but reappears/smears when acetone is applied |
| Methanol | 100% | NA | NA | NA | Evaporates |
| Methanol/p-xylene | 20%/80% | White | Clear | Rubs off | Spread out a little bit |
| Methyl Ethyl Ketone (MEK) | 100% | White-blue | Light blue | Scratchable | Circular |
| MEK/Dimethyl Sulfoxide/p-xylene | 20%/20%/60% | White-blue | Blue | Durable | Circular, visible pores |

TABLE 2-continued

Solvents and Polycarbonate Discs

| Description | Conc., % | Pattern Color Upon Solvent Treatment | Color Change After IPA Contact | Durability | Behavior |
|---|---|---|---|---|---|
| MEK/p-xylene | 20%/80% | White | Bluish clear | Scratchable | Forms blob shape |
| MEK/p-xylene | 50%/50% | White | Light blue | Scratchable | Not uniform, spreads out |
| MEK/p-xylene | 70%/30% | Light blue | Darker lighter blue (just looks wet) | Scratchable | Forms blob shape |
| MEK/p-xylene | 30%/70% | White | Light blue | Durable | Circular |
| Methyl Pyrrolidone | 100% | Blue with white Rim | Doesn't really change | Durable | Circular |
| Methyl Pyrrolidone/p-xylene | 20%/80% | Bluish | Doesn't really change | Durable | Circular |
| Methyl Sulfoxide | 100% | White | Doesn't change | Scratchable | Globular form |
| Methylene Chloride | 100% | NA | NA | NA | Dissolves surface |
| N,N-dimethyl Formamide | 100% | NA | NA | NA | Dissolves surface |
| N,N-dimethyl Formamide/p-xylene | 20%/80% | Blue | Clear | Durable | Dissolves surface |
| N,N-dimethyl Formamide/p-xylene | 50%/150% | Blue | Doesn't really change | Durable | Circular, pores visible |
| N,N-dimethyl Formamide/p-xylene | 80%/20% | Blue | Doesn't really change | Durable | Circular/partially dissolved surface |
| N-Heptane/p-xylene | 20%/80% | White | Clearish blue | Scratchable | Spreads out |
| Octanone, 98% p-xylene | 10%/90% | Whitish blue | Light blue | Durable | NA/applied on leur part only |
| Parafin oil/p-xylene | 20%/80% | NA | NA | NA | Smears |
| Poly(dimethyl Siloxane) p-xylene | 20%/80% | Dingy white | Clear | Scratchable | Not uniform, spreads out |
| Propylene Carbonate, 99% | 100% | Mostly blue/little white | Clear | Durable | Not a uniform circle |
| THF | 100% | White | Almost clear | Durable | Partially dissolved surface |
| THF/p-xylene | 5%/95% | White | Clear | Durable | Circular |
| Toluene | 100% | Blue | Clear | Durable | Oval/circular |

A number of solvents were also used on membranes made of polycarbonate, obtained from Nuclepore Corp., Pleasanton, Calif., U.S.A., membrane part no 113508, pore size 0.6 µm, and a thickness of 10 micrometer. As shown in Table 3 below, one particularly suitable solvent was a mixture of 20/80 N,N-dimethylformamide (DMF)/p-xylene. The membrane achieved the goal of changing from opaque to transparent without tearing or ripping the membrane.

TABLE 3

Solvents and Polycarbonate Membranes

| Solvent(s) | Concentration (%) | Result |
|---|---|---|
| Cyclohexane/p-xylene | 50/50 | No effect |
| Dimethylsulfoxide/p-xylene | 10/90 | Transparent on edges only |
| Methylethylketone/p-xylene | 20/80 | Transparent on edges only |
| Methylethylketone/p-xylene | 30/70 | No effect |
| DMF/p-xylene | 50/50 | Tore the membrane |
| DMF/p-xylene | 20/80 | Turned transparent, no rips |
| p-xylene | 100% | Transparent on edges only |

It is thus appreciated that surfaces may be made sensitive to selected wipes by surface treatments that allow limited penetration and expulsion of selected solvents. The surface appearance, and the change in surface appearance, allows users to determine whether a surface has been recently wiped with that solvent. The above data also demonstrate that the performance of a particular solvent is dependent on the individual substrate or polymer obtained. The Nuclepore polycarbonate membranes and the above-mentioned polycarbonate differ in one respect in the performance of the surface of the polycarbonate in response to different solutions of DMF/p-xylene. The dispersion on the polymer surface can be optimized or enhanced to obtain the desired optical properties. In addition to the work with polycarbonate surfaces, dispersions were made of various powders in solvents, and attempts made to apply them to the surface of an access device. The powders included PTFE, Cat. No. CAS90002-84-0 (Scientific Polymer Products, Ontario, N.Y., U.S.A., methylcellulose (Scientific Polymer Products, Cat. No. CAS9004-67-4, and carboxyl-modified polyacrylamide membranes, Scientific Polymer Products, Cat. No. CAT376. Dispersions made of vinyl alcohol/vinyl butyral with an 80% granular content, Scientific Polymer Products, Cat. No. CAS27360-07-2, were also tried. The dispersions were formulated as acrylates in the above-mentioned MB-6 formulation and were applied to the surfaces of LAD housings. These coatings prevented abrasions of the particulates in a powdery layer.

Incorporating Particles and Beads into Membrane Applications for Swab Sensing As noted above, color or appearance changes for swabbing with an alcohol wipe may be incorporated into membranes or surfaces not only by incorporating the dyes into the housing itself or the composition of a coating, as with the acrylic coatings, but may also be accomplished with surface treatment of the membrane or housing. In these coatings, there is no dye. Instead, a color change is accomplished by modifying the surface or adding a coating to the surface. The membrane is porous to a swabbing compound, such as IPA. The administration of the IPA changes the transparency sufficiently to change the color reflected back to an observer. In some of the embodiments described below, the housing and membrane covering it appear opaque, or may have an opaque-appearing color, but become transparent or translucent swabbed or wetted with IPA or other disinfecting liquid. It is believed that the change in transparency may arise from a relatively close match between the refractive index of the modified surface and the swabbing compound.

For example, as seen in FIG. 14e, an exposure indicator 88 may be mounted to an access device housing 24 with an adhesive 90, and undergo a change in transparency upon exposure to an antiseptic agent. In another example, FIGS. 15d-15e depict a housing 24 with an upper surface 110. Atop this surface, there are microcracks 130 in the bottom surface 132 of film 128 with pores 136. As seen in FIG. 15e, film 128 includes both pores 136 and microcracks 130. Dry (air filled) microporous structures appear white to the observer even when the strands comprising the microporous structures are transparent. The reason for this may be the mismatch between the refractive index of the solid strand of material and the surrounding air. If the air is replaced by another fluid with a refractive index identical to or very close to that of the strand, the structure will appear transparent to the observer. Various polymeric materials can be used as an exposure indicator in which a noticeable change in transparency occurs upon wetting with an antiseptic agent. Such materials can have a refractive index within a range approaching or approximating that of the typical antiseptic agent. For example, polymeric materials having a refractive index in the range of 1.25 to 1.60 may be particularly suited to this embodiment. Materials having a refractive index in this range include, but are not limited to: materials or particles of polydimethylsiloxane (n=1.43), polytetrafluoroethylene (PTFE) (n=1.35 to 1.38), polyethylene (1.51-1.54), polychlorotrifluoroethylene, polyvinylidene fluoride, polyvinyl acetate, cellulose acetate (n=1.46 to 1.50), ethylene vinyl acetate copolymer, poly methyl methacrylate (n=1.49), polypropylene (n=1.49), polyacrylic acid, polyethylene-terephthalate (PET) (n=1.57), polyvinyl chloride, and polycarbonate (n=1.58).

In use, it is desired that the antiseptic fluid penetrate the structure thoroughly if it is to wet thoroughly. One can use this phenomenon as a visual signal of good wetting by a known fluid. For example, ePTFE (expanded PTFE) and 70% IPA have almost identical refractive indices. Thus, when a microporous ePTFE membrane, which is white or opaque to the eye when dry, is wetted by swabbing with a 70% IPA, the membrane becomes transparent, and the underlying color or predetermined visual signal, such as a color or printed message, will be visually discernible. If the user tries to swab with a fluid which does not provide effective swabbing, which by way of example may be water, blood, infusion solutions or drugs, the ePTFE membrane will not wet, and will remain white. Such fluids may interfere with the indicating properties or provide a medium for the growth of infectious agents. In this regard, it also may be desirable to provide a hydrophobic coating on or over the exposure indicator layer to substantially prevent a change in transparency in the presence of water. Such hydrophobicity can be described for purposes of this description as any material that is wettable by alcohol, and not wettable by water. In this way, water may be rejected or segmented out by the hydrophobic coating, while only the antiseptic agent will wet the microporous membrane.

In an embodiment, the wetting and subsequent change in transparency maybe accomplished by the replacement of the air in the membrane by a fluid which may have a similar refractive index. The membrane itself may have the hydrophobicity as described above. With the replacement of the air the discernible transparency of the membrane changes.

The visual indication provided by the above-described change in transparency has particular advantages. First, it is purely physical in nature and does not rely on incorporated dyes or pigments and is not subject to extractables of any kind. Also, the swabbing fluid that includes 70% isopropyl alcohol can be used effectively to create a visual indication of swabbing with materials that have a long history of use in medical deices. Alternatively, materials which have a refractive index similar to chlorhexidine in 70% IPA or allow absorption of such a fluid can also be used and conversely such a fluid may be used as a swabbing agent.

Such a microporous structure may be carried or mounted on the gland or housing or both in any desired manner. If provided as a separate member, the microporous structure could be in the form of a membrane or other structure, with a plurality of holes or pores, and with an adhesive backing 90 attached to the housing or gland using ultrasound, adhesive, heat binding or other techniques. The structure may also be applied to the housing decorative molding techniques.

In an embodiment, the microporous material may be an ePTFE material having a polyester, polyethylene or polypropylene mesh support which facilitates attachment to the housing. In particular such mesh facilitates sonic welding or attachment by liquid adhesive of the material to the surface. Additional layers of polyester mesh may be used to aid in the attachment of the microporous material to the housing. Membranes having a polyester mesh support are commercially available.

The change in transparency may itself be a visual indication to the user, or the microporous structure may be used in combination with a signal source. When in a substantially non-transparent state, the microporous structure may serve to obscure the signal source, such as a source that is situated therebelow. Such a signal source may be, for example, a particular color, a text message, a bar code or other computer readable image, an icon, or other indicator that, when revealed, would provide an indication to the clinician that the access device has been exposed to antiseptic agent. Conversely, when the signal source is obscured by the non-transparent state of the indicator, the clinician will be alerted to the fact that the surface of the access device has not been treated with antiseptic agent. Accordingly, as the microporous structure dries, it returns to a non-transparent state, alerting the clinician to swab the access device before using it again. The reading of the signal source by a accessory device such as reader may then produce a signal which is fed into a medical information system or database to verify and produce a historical record of the swabbing before administration. It is not necessary that the refractive indices of the antiseptic agent and the membrane be so close that complete transparency occurs (although that may be preferred). It is sufficient if the change in transparency is sufficiently noticeable to the user to permit its use as an indicator or contact with an antiseptic agent.

In a further embodiment a layer of the microporous structure may be applied to a layer of the indicating material which also displays a perceptible signal when contacting the swabbing fluid. Thus the outer layer becomes transparent and in and example, an intermediate layer visually indicates that the swabbing has occurred.

In a further embodiment, the degree of transparency exhibited may be controlled such that the desired degree of transparency only occurs upon a desired level of swabbing. By way of example, an indicator such as a bar code may not be perceptible to the required degree of readability by a bar code reader unless the membrane is sufficiently wetted or swabbed. One method of achieving this control is to provide two or more layers of the membrane which require the desired swabbing before the needed transparency is achieved. Another method is to select a membrane with a pore size sufficient to affect the degree of transparency and to filter out pathogens, preventing pathogens from penetrating through the membrane prior to or after use of the device.

In a series of experiments, polymeric resins or elastomeric formulae were mixed with previously-cured powders or beads and tested for their ability to change color when wetted with IPA, simulating the situation in which a medical professional swabs an access device in preparation for administering a drug or other substance to a patient. Epoxy formulations were tested, as were numerous other thermoset and thermoplastic matrices. Silicone rubber matrices were tested.

In another series of experiments, a quantity of PVDF powder was mixed with a solution of 15% polycarbonate/85% cyclohexanone. The cyclohexanone was obtained from J. T. Baker, Phillipsburg, N.J., U.S.A., the polycarbonate was Makrolon RX 1805-118 from Bayer Material Science, Pittsburgh, Pa., U.S.A. A few drops of this solution were then applied to the ring of a blue Flolink™ device using a 26 ga. Needle. The device was placed in water to precipitate solution onto the surface of the Flolink™ device. The result was a white coating on the Flolink™ device. The color changed from white to blue. After several more minutes, the color changed back to white.

Another series of experiments involved polyethylene (PE) membranes obtained from DSM, SOLUPOR® brand, sold as 1 to 4 mils thick, and made by a process that includes stretching the membrane. No powder was used. The membranes had pore sizes of 0.1 μm. In these experiments, a first PE membrane was cut with a ⅝" die cutter and placed into a tool. Dow Corning RTV-J base and curing agent were mixed in the proper proportions and poured into the mold. The rubber covered the membrane as it was poured into the center of the mold and covered the PE membrane. This procedure prevents wrinkling of the membrane. The mold was closed and heated to 230° F. for 5 minutes. The mold was removed from the tool and cooled to room temperature. The rubber/membrane composite was then removed from the tool. The composite and tested for color change with 70% IPA. The composite turned from white to transparent instantaneously, and changed back again within 1 minute. A similar experiment was tried with 8 mil PTFE membranes from Donaldson (Cat. No. AX06-145). The results were similar.

Another series of experiments involved application of cured elastomeric powder (PVDF) to form an indicator. A spatula-full of cured PVDF powder was placed into a tool and the Dow Corning RTV-J mixture described above was poured into the tool. The tool was closed and placed into a hot press at 230° F. for 5 minutes. The tool was then removed from the press and cooled to room temperature. The cured rubber with molded in PVDF particles was then removed from the tool and cooled. The membrane was tested. The dry color of the membrane was white. When wetted with a mixture of 70% IPA and 30% water, the surface turned transparent, revealing the color of the underlying RTV.

Another series of experiments used colored silicone rubber. GE silicone base LIM 6071 part A, 5.01 g., was mixed with silicone cure, part B, 5.00 g., forming a clear, colorless, very viscous mixture The mixture was stirred and 0.02 g. Silcopas Red 346, Gayson Silicone Dispersions, Inc., Barberton, Ohio U.S.A., was added to the mixture. Another sample was prepared using 0.02 g. Silcopas Blue with GE silicone LIM mixture. Several types of membranes were prepared and cut into ⅝" diameter circles. Each membrane was placed in the bottom portion of the tool and the silicone mixture was placed in the top. The two were brought together and the tool was closed, and pressed in a hot press at 230° F. for five minutes. Table 4 below summarizes the results. By varying the viscosity of the silicone, mold temperature and molding time, it is possible to optimize the appearance change of the membrane, from light red to red, upon wetting with 70% IPA.

TABLE 4

Membranes and GE LIM Silicone

| Sample No. | Membrane thickness and material, mils | Index of refraction, n = | Rubber matrix | Color change dry/wet | Recovery time, seconds |
|---|---|---|---|---|---|
| 1 | PE, 1 mil | 1.5 | LIM 6071, red | light red/red | <60 s |
| 2 | PE, 3 mil | 1.5 | LIM 6071, red | very white/light red | <60 s |
| 3 | PTFE, 8 mil | 1.35 ' | LIM 6071, red | light red/red | <60 s |
| 4 | PE, 1 mil | 1.5 | LIM 6071, blue | Light blue/blu | <60 s |

The above samples did not show a great deal of contrast between the dry and wet states. Accordingly, another series of samples was prepared. In this series, 10.02 g. Dow Silastic MDX-4210 part A was mixed with 1.03 g. curing agent (at a 10 to 1 ratio). 0.25 g. Silcopas red was added to the mix. This silicone mix was much less viscous than the LIM materials above. Precut membranes as described above were placed into the bottom portion of the tool and the silicone rubber mix was poured over the membrane, beginning from the center. The lid was then added to the tool, which was placed in the hot press and cured at 230° F. for 5 minutes. The tool was removed from the press Sand cooled to room temperature, and the membrane was removed from the tool. In test #8, PVDF powder was placed in the mold instead of a membrane and the powder was evenly spread over the bottom of the mold. The red Dow Silastic mix was poured over the PVDF powder. The composition was then processed in a manner similar to the other specimens. The results are shown in Table 5 below.

TABLE 5

Membranes and Dow Silastic Material

| Sample No. | Membrane thickness and material, mils | Index of Refraction, N = | Rubber matrix | Color change dry/wet | Recovery time, seconds |
|---|---|---|---|---|---|
| 5 | PE, 1 mil | 1.5 | MDX 4210, red | white/red | <60 s |
| 6 | PE, 3 mil | 1.5 | MDX 4120, red | white/light red | <60 s |
| 7 | PTFE, 8 mil | 1.35 | MDX 4210, red | white/red | <60 s |
| 8 | PVDF powder | 1.42 | MDX 4210, red | white/red | >60 s |

These experiments show that membranes made with several materials and with a refractive index of about 1.25 to about 1.6 readily transform from one appearance to another, e.g., from opaque to transparent, or from a first color to a second color.

It should be understood that the perceptible indication may include a perceptible change in appearance using visible or non-visible light or a combination of thereof. Moreover, the perceptible change may be visibly discernible or may be discernible through the use of an accessory device or a combination thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid access device comprising:

a housing and a valve member defining a fluid access site for introduction and withdrawal of fluids; and a polymeric porous indicator including a color changing dye, wherein the polymeric porous indicator is disposed at the access site, wherein upon exposure to an antiseptic solution the color changing dye changes from a first color to a second color, and wherein the dye resumes the first color after a period of time.

2. The access device of claim 1, wherein the color changing dye is a solvatochromic dye.

3. The access device of claim 2, wherein the color changing dye is a merocyanine dye or a salt or derivative thereof, or Reichardt's dye or a salt or derivative thereof.

4. The access device of claim 1, wherein the color changing dye comprises a compound having the structure:

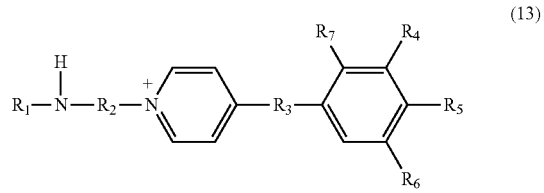

(13)

and derivatives and salts thereof, and wherein R1 is acryloyl, methacryloyl, or hydrogen, R2 is C4 to C10 alkyl, R3 is ethene, R4 and R6 are bromide, chloride, fluoride, iodide, and mixtures thereof, R5 is one of hydrogen or O$^-$, and R7 is the other of hydrogen and O$^-$.

5. The access device of claim 4, wherein if R1 is acryloyl, the derivatives comprise ammonium hydroxide, alkali and alkaline earth salts, and mixtures thereof, and if R1 is hydrogen, the derivatives comprise a hydrobromide, hydrochloride, hydrofluoride, phosphate, sulfate, and mixtures thereof.

6. The access device of claim 4, wherein R1 is hydrogen, R2 is n-hexyl, R4 and R6 are chloride, R5 is hydrogen, and R7 is O$^-$.

7. The access device of claim 1, wherein the indicator is alcohol permeable and the polymer from which the indicator is made has an index of refraction from about 1.25 to about 1.6.

8. The access device of claim 1, wherein the indicator further comprises a solvatochromic dye or a salt or a derivative thereof in an amount from about 0.1% to about 0.5% of the weight of the material.

9. The access device of claim 1, wherein the polymer is at least one of acrylic, COC, nylon, methacrylic, elastomer, polycarbonate, polyurethane, epoxy, polyester, and vinylester.

10. The access device of claim 1, wherein the porous polymeric indicator comprises a membrane made from a polymer having an index of refraction from about 1.25 to about 1.6, and further comprising a coating containing the color changing dye.

11. The access device of claim 1, wherein the color changing dye is chemically bonded to the access site.

* * * * *